United States Patent
Freskos et al.

(10) Patent No.: US 7,297,793 B2
(45) Date of Patent: *Nov. 20, 2007

(54) BIS-SULFONAMIDE HYDROXYETHYLAMINO RETROVIRAL PROTEASE INHIBITORS

(75) Inventors: John N. Freskos, Clayton, MO (US); Daniel P. Getman, Chesterfield, MO (US); John J. Talley, Brentwood, MO (US); James A. Sikorski, Des Peres, MO (US)

(73) Assignee: G.D. Searle, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/349,352

(22) Filed: Feb. 8, 2006

(65) Prior Publication Data

US 2006/0199822 A1 Sep. 7, 2006

Related U.S. Application Data

(63) Continuation of application No. 10/417,340, filed on Apr. 17, 2003, now Pat. No. 7,091,219, which is a continuation of application No. 10/076,607, filed on Feb. 19, 2002, now Pat. No. 6,569,882, which is a continuation of application No. 09/635,896, filed on Aug. 11, 2000, now Pat. No. 6,384,036, which is a continuation of application No. 08/875,025, filed as application No. PCT/US96/00607 on Jan. 18, 1996, now Pat. No. 6,143,747, which is a continuation-in-part of application No. 08/376,337, filed on Jan. 20, 1995, now abandoned.

(51) Int. Cl.
C07D 295/26 (2006.01)
C07D 413/12 (2006.01)
C07D 401/14 (2006.01)
C07D 401/12 (2006.01)

(52) U.S. Cl. .............. 544/160; 544/360; 544/383; 546/247

(58) Field of Classification Search .......... 544/160, 544/383, 360; 546/247
See application file for complete search history.

(56) References Cited

U.S. PATENT DOCUMENTS

| | | | |
|---|---|---|---|
| 4,477,441 A | 10/1984 | Boger et al. |
| 4,514,391 A | 4/1985 | Gordon et al. |
| 4,548,926 A | 10/1985 | Matsueda et al. |
| 4,599,198 A | 7/1986 | Hoover |
| 4,616,088 A | 10/1986 | Ryono et al. |
| 4,668,769 A | 5/1987 | Hoover |
| 4,668,770 A | 5/1987 | Boger et al. |
| 4,757,050 A | 7/1988 | Natarajan et al. |
| 4,880,938 A | 11/1989 | Freidinger |
| H725 H | 1/1990 | Gordon |
| 4,963,530 A | 10/1990 | Hemmi et al. |
| 4,977,277 A | 12/1990 | Rosenberg et al. |
| 5,157,041 A | 10/1992 | Handa et al. |
| 5,508,294 A | 4/1996 | Vazquez et al. |
| 5,521,219 A | 5/1996 | Vazquez et al. |
| 5,639,769 A | 6/1997 | Vazquez et al. |
| 5,760,064 A | 6/1998 | Vazquez et al. |
| 6,143,747 A | 11/2000 | Freskos et al. |
| 6,384,036 B1 | 5/2002 | Freskos et al. |
| 6,569,882 B2 | 5/2003 | Freskos et al. |

FOREIGN PATENT DOCUMENTS

| | | |
|---|---|---|
| EP | 0 104 041 | 3/1984 |
| EP | 0 114 993 | 8/1984 |
| EP | 0 172 347 | 2/1986 |
| EP | 0 223 437 | 5/1987 |
| EP | 0 264 795 | 4/1988 |
| EP | 0 337 714 | 10/1989 |
| EP | 0 342 541 | 11/1989 |
| EP | 0 346 847 | 12/1989 |
| EP | 0 356 223 | 2/1990 |
| EP | 0 389 898 A2 | 10/1990 |
| EP | 0 389 898 A3 | 10/1990 |
| EP | 0 393 445 | 10/1990 |
| EP | 0 393 457 | 10/1990 |
| EP | 0 402 646 | 12/1990 |
| EP | 0 468 641 | 1/1992 |

(Continued)

OTHER PUBLICATIONS

Thomber, Chemical Society Reviews, vol. 8, No. 1, 1979, pp. 563-580 (1979).
Rich et al., Peptide Inhibitors of Proteases, 511-520, 1983.
Rosenberg et al., J. Med. Chem. 30, 1224-1228 (1987).
Roberts et al., "Rational design of Peptide-Based Proteinase Inhibitors," Science, 248, 358 (1990).

(Continued)

*Primary Examiner*—Laura L. Stockton
(74) *Attorney, Agent, or Firm*—Banner & Witcoff Ltd.

(57) ABSTRACT

Bis-sulfonamido hydroxyethylamino compounds are effective as retroviral protease inhibitors, and in particular as inhibitors of HIV protease. The present invention relates to retroviral protease inhibiting compounds of the formula:

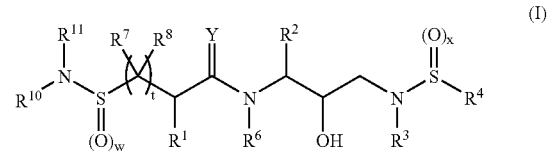

or a pharmaceutically acceptable salt, prodrug or ester thereof, wherein the variables are as defined herein.

20 Claims, No Drawings

FOREIGN PATENT DOCUMENTS

| | | |
|---|---|---|
| GB | 2184730 | 7/1987 |
| GB | 2200115 | 7/1988 |
| GB | 2209752 | 5/1989 |
| WO | WO 84/03044 | 8/1984 |
| WO | WO 92/00750 | 1/1992 |
| WO | WO 93/10134 | 5/1993 |
| WO | WO 93/10136 | 5/1993 |
| WO | WO 93/23368 | 11/1993 |
| WO | WO 93/23379 | 11/1993 |
| WO | WO 94/04491 | 3/1994 |
| WO | WO 94/04492 | 3/1994 |
| WO | WO 94/04493 | 3/1994 |
| WO | WO 94/05639 | 3/1994 |

OTHER PUBLICATIONS

Erickson et al., "Design activity and 2.8Å Crystal Structure of a $C_2$ Symmetric Inhibitor Complexed to HIV-1 Protease," Science, 249, 527 (1990).

Pearl et al., "Sequence Specificity of Retroviral Proteases" Nature, 328 (1987).

Martin, Drugs of the Future, 16(3), 210-212 (1991).

Meek et al., Letter to Nature, 343, 90-92 (1990).

McQuade et al., Science, 247, 454-456, 1990.

BIS-SULFONAMIDE HYDROXYETHYLAMINO RETROVIRAL PROTEASE INHIBITORS

CROSS-REFERENCE TO RELATED APPLICATIONS

This application is a continuation of U.S. patent application Ser. No. 10/417,340, filed Apr. 17, 2003, now U.S. Pat. No. 7,091,219, which is a continuation of U.S. patent application Ser. No. 10/076,607, filed Feb. 19, 2002, now U.S. Pat. No. 6,569,882, which is a continuation of U.S. patent application Ser. No. 09/635,896 filed on Aug. 11, 2000, now U.S. Pat. No. 6,384,036, which is a continuation of U.S. patent application Ser. No. 08/875,025, filed Feb. 26, 1998, now U.S. Pat. No. 6,143,747, which is the U.S. national phase of International Application No. PCT/US96/00607, filed Jan. 18, 1996, which is a continuation-in-part application of U.S. patent application Ser. No. 08/376,337, filed Jan. 20, 1995, now abandoned.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to bis-sulfonamide-containing hydroxyethylamine protease inhibitor compounds, a composition and method for inhibiting retroviral proteases such as human immunodeficiency virus (HIV) protease and for treating a retroviral infection, e.g., an HIV infection. The subject invention also relates to processes for making such compounds as well as to intermediates useful in such processes.

2. Related Art

During the replication cycle of retroviruses, gag and gag-pol gene transcription products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease active site that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit specific processing of structural proteins and the release of retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EP O 346 847; EP O 342,541; Roberts et al, "Rational Design of Peptide-Based Proteinase Inhibitors, "Science, 248, 358 (1990); and Erickson et al, "Design Activity, and 2.8 Å Crystal Structure of a $C_2$ Symmetric Inhibitor Complexed to HIV-1 Protease," Science, 249, 527 (1990). Sulfonamide-containing, aminosulfonamide-containing and urea-containing hydroxyethylamine compounds and intermediates useful as retroviral protease inhibitors have been disclosed in WO94/05639, WO94/10136, WO94/10134, WO94/04493, WO94/04492, WO 93/23368, and WO93/23379.

Several classes of compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.B. 2,200,115, GB 2,209,752, EP O 264,795, U.S. SIR H725 and U.S. Pat. No. 4,599,198 disclose urea-containing hydroxyethylamine renin inhibitors. EP 468 641 discloses renin inhibitors and intermediates for the preparation of the inhibitors, which include sulfonamide-containing hydroxyethylamine compounds, such as 3-(t-butoxycarbonyl)amino-cyclohexyl-1-(phenylsulfonyl)amino-2(5)-butanol. G.B. 2,200,115 also discloses sulfamoyl-containing hydroxyethylamine renin inhibitors, and EP 0264 795 discloses certain sulfonamide-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as bis-sulfonamide-containing hydroxyethylamine inhibitor compounds.

DETAILED DESCRIPTION OF THE INVENTION

In accordance with the present invention, there is provided a retroviral protease inhibiting compound of the formula:

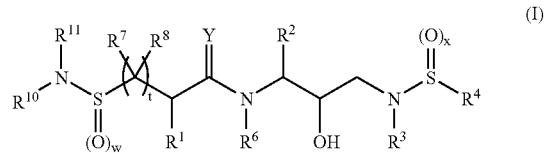

(I)

or a pharmaceutically acceptable salt, prodrug or ester thereof, wherein $R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2$ (SH), —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl cycloalkyl, cycloalkvlalkyl, heterocyclo, heterocycloalkyl, aminosulfonylalkyl, N-alkylaminosulfonylalkyl, N,N-di-alkylaminosulfonylalkyl, aryl, aralkyl, heteroaryl or heteroaralkyl radicals, an amino acid side chain of asparagine, lysine, aspartic acid, aspartic acid methyl ester, methionine or the sulfoxide (SO) or sulfone ($SO_2$) derivatives thereof, S-methyl cysteine or the sulfoxide (SO) or sulfone ($SO_2$) derivatives thereof, isoleucine, allo-isoleucine, alanine, leucine, tert-leucine, phenylalanine, ornithine, histidine, norleucine, glutamine, threonine, allo-threonine, serine, O-alkyl serine, beta-cyano alanine or valine;

$R^2$ represents alkyl, aryl, cycloalkyl, cycloalkylalkyl, aralkyl, heteroaryl or heteroaralkyl radicals, which radicals are optionally substituted with one or more alkyl, halogen, —$NO_2$, —CN, —$CF_3$, —$OR^9$ or —$SR^9$ radicals, wherein $R^9$ represents hydrogen, alkyl, aryl, heteroaryl, cycloalkyl or heterocyclo radicals;

$R^3$ represents hydrogen, alkyl, haloalkyl, alkenyl, alkynyl, hydroxyalkyl, alkoxyalkyl, cycloalkyl, cycloalkylalkyl, heterocyclo, heteroaryl, heterocycloalkyl, aryl, aralkyl, heteroaralkyl, thioalkyl, alkylthioalkyl or arylthioalkyl radicals or the corresponding sulfone or sulfoxide derivatives thereof, aminoalkyl or N-mono- or N,N-disubstituted aminoalkyl radicals, wherein said substituents are alkyl, aryl, aralkyl, cycloalkyl, cycloalkylalkyl, heteroaryl, heteroaralkyl, heterocyclo, or heterocycloalkyl radicals;

$R^4$ represents alkyl, haloalkyl, alkenyl, alkynyl, hydroxyalkyl, alkoxyalkyl, cycloalkyl, cycloalkylalkyl, heterocyclo, heteroaryl, heterocycloalkyl, arvl, aralkyl, aralkenyl, heteroaralkyl, alkoxycarbonylaminoheteroaryl, thioalkyl, alkylthioalkyl or arylthioalkyl radicals or the corresponding sulfone or sulfoxide derivatives thereof, aminoalkyl or N-mono- or N,N-disubstituted aminoalkyl radicals, wherein said substituents are alkyl, aryl, aralkyl, cycloalkyl, cycloalkylalkyl, heteroaryl, heteroaralkyl, heterocyclo, or heterocycloalkyl radicals, thioalkyl, alkylthioalkyl or arylthioalkyl radicals or the corresponding sulfone or sulfoxide derivatives thereof;

$R^6$ represents hydrogen or alkyl radicals;

each $R^7$ independently represents carboxy, amidino or N-alkylamidino radicals, or radicals as defined for $R^1$; or $R^7$ together with $R^1$ and the carbon atoms to which $R^1$ and $R^7$ are attached, represent cycloalkyl or heterocyclo radicals;

each $R^8$ independently represents hydrogen or alkyl radicals;

$R^{10}$ and $R^{11}$ each independently represent hydrogen, alkyl, hydroxyalkyl, alkoxyalkyl, cycloalkyl, cycloalkylalkyl, heterocyclo, heterocycloalkyl, aryl, aralkyl, heteroaryl, heteroaralkyl, heteroarylcarbonylalkyl, arylcarbonylalkyl, thioalkyl, alkylthioalkyl or arylthioalkyl radicals or the corresponding sulfone or sulfoxide derivatives thereof, aminoalkyl or N-mono- or N,N-disubstituted aminoalkyl radicals, wherein said substituents are alkyl, aryl, aralkyl, cycloalkyl, cycloalkylalkyl, heteroaryl, heteroaralkyl, heterocyclo or heterocycloalkyl radicals; or $R^{10}$ and $R^{11}$ together with the nitrogen to which they are attached represent heterocyclo, heteroaryl, aralkylheteroaryl, aralkylheterocyclo, heteroaralkylheteroaryl or heteroaralkylheterocyclo radicals;

x and w each represent 0, 1 or 2;

t represents 0-6; and

Y represents O, S or NH

A family of compounds of particular interest within Formula I are compounds embraced by Formula II:

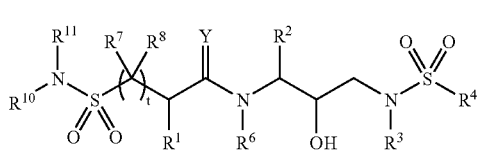

(II)

wherein $R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl, cycloalkyl, cycloalkylalkyl, aminosulfonylalkyl, N-alkylaminosulfonylalkyl, N,N-dialkylaminosulfonylalkyl or heteroaralkyl radicals, or an amino acid side chain of asparagine, lysine, aspartic acid, aspartic acid methyl ester, methionine or the sulfoxide (SO) or sulfone ($SO_2$) derivatives thereof, S-methyl cysteine or the sulfoxide (SO) or sulfone ($SO_2$) derivatives thereof, ornithine, leucine, isoleucine, norleucine, allo-isoleucine, alanine, phenylalanine, histidine, tert-leucine, glutamine, threonine, allo-threonine, serine, O-alkyl serine, beta-cyano alanine or valine;

$R^2$ represents alkyl, cycloalkyl, cycloalkylalkyl, aryl, aralkyl, heteroaryl or heteroaralkyl radicals, which radicals are optionally substituted with one or more alkyl, halogen, —$NO_2$, —CN, —$CF_3$, —$OR^9$ or —$SR^9$ radials, wherein $R^9$ represents hydrogen, alkyl, aryl, heteroaryl, cycloalkyl or heterocyclo radicals;

$R^3$ represents hydroqen, alkyl, alkenyl, alkynyl, haloalkyl, hydroxyalkyl, alkoxyalkyl, cycloalkyl, cycloalkylalkyl, heterocyclo, heterocycloalkyl, aryl, aralkyl, heteroaryl, heteroaralkyl, thioalkyl, alkylthioalkyl or arylthioalkyl radicals or the corresponding sulfone or sulfoxide derivatives thereof, aminoalkyl or N-mono- or N,N-disubstituted aminoalkyl radicals, wherein said substituents are alkyl, aryl, aralkyl, cycloalkyl, cycloalkylalkyl, heteroaryl, heteroaralkyl, heterocyclo or heterocycloalkyl radicals;

$R^4$ represents alkyl, alkenyl, alkynyl, haloalkyl, hydroxyalkyl, alkoxyalkyl, cycloalkyl, cycloalkylalkyl, heterocyclo, heterocycloalkyl, heteroaryl, heteroaralkyl, alkoxycarbonylaminoheteroaryl, aryl, aralkyl, aralkenyl, thioalkyl, alkylthioalkyl or arylthioalkyl radicals or the corresponding sulfone or sulfoxide derivatives thereof, aminoalkyl or N-mono- or N,N-disubstituted aminoalkyl radicals, wherein said substituents are alkyl, aryl, aralkyl, cycloalkyl, cycloalkylalkyl, heteroaryl, heteroaralkyl, heterocyclo or heterocycloalkyl radicals, thioalkyl, alkylthioalkyl or arylthioalkyl radicals or the corresponding sulfone or sulfoxide derivatives thereof;

$R^6$ represents hydrogen or alkyl radicals;

each $R^7$ independently represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, carboxy, amidino, N-alkylamidino, alkyl, aryl or aralkyl radicals; or $R^7$ together with $R^1$ and the carbon atoms to which $R^1$ and $R^7$ are attached, represent cycloalkyl or heterocyclo radicals;

each $R^8$ independently represents hydrogen or alkyl radicals;

$R^{10}$ represents hydrogen, alkyl, aryl, aralkyl, heterocyclo, heterocycloalkyl, heteroaryl or heteroaralkyl radicals;

$R^{11}$ represents hydrogen, alkyl, hydroxyalkyl, alkoxyalkyl, cycloalkyl, cycloalkylalkyl, heterocyclo, heterocycloalkyl, aryl, aralkyl, heteroaryl, heteroaralkyl, heteroarylcarbonylalkyl, arylcarbonylalkyl, thioalkyl, alkylthioalkyl or arylthioalkyl radicals or the corresponding sulfone or sulfoxide derivatives thereof, aminoalkyl or N-mono- or N,N-disubstituted aminoalkyl radicals, wherein said substituents are alkyl, aryl, aralkyl, cycloalkyl, cycloalkylalkyl, heteroaryl, heteroaralkyl, heterocyclo or heterocycloalkyl radicals; or $R^{10}$ and $R^{11}$ together with the nitrogen to which they are attached represent heterocyclo, heteroaryl, aralkylheteroaryl, aralkylheterocyclo, heteroaralkylheteroaryl or heteroaralkylheterocyclo radicals;

t represents 0-4; and

Y represents O, S or NH.

A more preferred family of compounds within Formula II consistes of compounds wherein:

$R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl, cycloalkyl, cycloalkylalkyl, aminosulfonylalkyl, N-alkylaminosulfonylalkyl, N,N-dialkylaminosulfonylalkyl or heteroaralkyl radicals, or an amino acid side chain of asparagine, lysine, aspartic acid, aspartic acid methyl ester, methionine or the sulfoxide (SO) or sulfone ($SO_2$) derivatives thereof, S-methyl cysteine or the sulfoxide (SO) or sulfone ($SO_2$) derivatives thereof, ornithine, leucine, isoleucine, norleucine, allo-isoleucine, alanine, phenylalanine, histidine, tert-leucine, glutamine, threonine, allo-threonine, serine, O-alkyl serine, beta-cyano alanine or valine;

$R^2$ represents alkyl, cycloalkyl, cycloalkylalkyl, aryl, aralkyl or heteroaralkyl radicals, which radicals are optionally substituted with one or more alkyl, halogen, —$NO_2$, —CN, —$CF_3$, —$OR^9$ or —$SR^9$ radicals, wherein $R^9$ represents hydrogen, alkyl, aryl, heteroaryl, cycloalkyl or heterocyclo radicals;

$R^3$ represents alkyl, alkenyl, alkynyl, haloalkyl, hydroxyalkyl, alkoxyalkyl, aminoalkyl, N-alkylaminoalkyl, N,N-dialkylaminoalkyl, cycloalkyl, cycloalkylalkyl, heterocyclo, heterocycloalkyl, aryl, aralkyl, heteroaryl, heteroaralkyl, thioalkyl, alkylthioalkyl or arylthioalkyl radicals or the corresponding sulfone or sulfoxide derivatives thereof;

$R^4$ represents alkyl, alkenyl, alkynyl, haloalkyl, hydroxyalkyl, alkoxyalkyl, cycloalkyl, cycloalkylalkyl, heterocyclo, heterocycloalkyl, heteroaryl, heteroaralkyl, alkoxycarbonylaminoheteroaryl, aryl, aralkyl or aralkenyl radicals;

$R^6$ represents hydrogen or alkyl radicals;

each $R^7$ independently represents hydrogen, —$CO_2CH_3$, —$CONH_2$, carboxy, amidino, N-alkylamidino, alkyl, aryl or aralkyl radicals; or $R^7$ together with $R^1$ and the carbon atoms to which $R^1$ and $R^7$ are attached, represent cycloalkyl or heterocyclo radicals;

each $R^5$ independently represents hydrogen or alkyl radicals;

$R^{10}$ represents hydrogen, alkyl, aralkyl or heteroaralkyl radicals;

$R^{11}$ represents hydrogen, alkyl, hydroxyalkyl, alkoxyalkyl, aminoalkyl, N-alkylaminoalkyl, N,N-dialkylaminoaikyl, cycloalkyl, cycloalkylalkyl, heterocyclo, heterocycloalkyl, aryl, aralkyl, heteroaryl, heteroaralkyl, heteroarylcarbonylalkyl or arylcarbonylalkyl radicals; or $R^{10}$ and $R^{11}$ together with the nitrogen to which they are attached represent heterocyclo, heteroaryl, aralkylheteroaryl, aralkylheterocyclo, heteroaralkylheteroaryl or heteroaralkylheterocyclo radicals;

t represents 0-4; and

Y represents O or S.

Of higest interest are compounds within Formula II wherein $R^1$ represents hydrogen, —$CH_2C(O)NHCH_3$, —$C(CH_3)_2(SCH_3)$, $C(CH_3)_2(S[O]CH_3)$, —$C(CH_3)_2(S[O]_2CH_3)$, methyl, ethyl, isopropyl, iso-butyl, sec-butyl, tert-butyl, propenyl or propargyl radicals, or an amino acid side chain of asparagine, S-methyl cysteine, isoleucine, allo-isoleucine, alanine, tert-leucine or valine;

$R^2$ represents $CH_3SCH_2CH_2$—, iso-butyl, n-butyl, benzyl, fluorobenzyl, naphthylmethyl, cyclohexylmethyl, phenylthiomethyl or naphthylthiomethyl radicals;

$R^3$ represents isoamyl, iso-butyl, propyl, n-butyl, cyclohexyl, cycloheptyl, cyclohexylmethyl, cyclopentylmethyl, cyclopropylmethyl, pyridylmethyl or benzyl radicals;

$R^4$ represents methyl, phenyl, pyridyl, furyl, imidazolyl, methylenedioxyphen-4-yl, methylenedioxyphen-5-yl, ethylenedioxyphenyl, benzothiazolyl, benzopyranyl, benzimidazolyl, benzofuryl, 2,3-dihydrobenzofuryl, benzoxazolyl, oxazolyl, thiazolyl or thiophenyl radicals, optionally substituted with one or more methyl, methoxy, fluoro, chloro, hydroxy, amino, nitro or methoxycarbonylamino radicals;

$R^6$ represents hydrogen or methyl radicals;

each $R^7$ independently represents hydrogen, —$CO_2CH_3$, —$CONH_2$ or methyl radicals; or $R^7$ together with $R^1$ and the carbon atoms to which $R^1$ and $R^7$ are attached represent cyclopropyl, cyclobutyl, cyclopentyl or cyclohexyl radicals;

each $R^8$ independently represents hydrogen or methyl radicals;

$R^{10}$ and $R^{11}$ each independently represent hydrogen, methyl, ethyl, propyl, isopropyl, butyl, isobutyl, tert-butyl, pyrolylethyl,-piperidinylethyl, pyrrolidinylethyl, morpholinylethyl, thiomorpholinylethyl, pyridylmethyl, methylaminoethyl, dimethylaminoethyl, phenyl, benzyl or diphenylmethyl radicals; or $R^{10}$ and $R^{11}$ together with the nitrogen to which they are attached represent piperidinyl, morpholinyl, thiomorpholinyl or sulfone or sulfoxide derivatives thereof, piperazinyl, pyrrolidinyl or pyrrolyl radicals, or N-(alkyl)piperazinyl, N-(aralkyl)piperazinyl, N-(heteroaralkyl)piperazinyl or N-(heterocycloalkyl) piperazinyl radicals, such as N-methylpiperazinyl, N-ethylpiperazinyl, N-benzylpiperazinyl, N-(pyridylmethyl)piperazinyl, N-(tetrahydrothienylmethyl) piperazinyl, N-(thiazolylmethyl)piperazinyl, N-(furylmethyl)piperazinyl, N-(benzoxazolylmethyl) piperazinyl, N-(piperidinylethyl)piperazinyl, N-(morpholinoethyl)piperazinyl and the like;

t represents 0 or 1; and

Y represents O or S.

The absolute stereochemistry of the carbon atom of —CH(OH)— group is preferably (R). The absolute stereochemistry of the carbon atom of —CH($R^1$)— group is preferably (S). The absolute stereochemistry of the carbon atom of —CH($R^2$)— groups is preferably (S).

As utilized herein, the term "alkyl", alone or in combination, means a straight-chain or branched-chain alkyl radical containing preferably from 1 to 10 carbon atoms, more preferably from 1 to 8 carbon atoms, most preferably 1-5 carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "thioalkyl" means an alkyl radical as defined above which is substituted by at least one —SH group. "Alkylthioalkyl" and "arylthioalkyl" means an alkyl radical as defined above which is substituted by at least one alkyl-S and aryl-S—, respectively, where alkyl and aryl are as defined herein. Examples of thioalkyl, alkylthioalkyl and arylthioalkyl are —$CH_2SCH_2CH_3$, —$CH_2CH_2SH$, —$C(CH_3)_2SH$, —$C(CH_3)_2SCH_3$, —$(CH_2)_2SCH_3$, —$CH_2S$-phenyl and the like. The corresponding sulfoxide and sulfone of such thioalkyls are —$CH_2S(O)CH_2CH_3$, —$C(CH_3)_2S(O)CH_3$, —$C(CH_3)_2S(O)CH_3$, —$CH_2S(O)_2CH_2CH_3$, —$C(CH_3)_2S$ (O)₂CH₃, —CH₂S(0)phenyl, —CH₂—S(O)₂phenyl, —C(CH₃)₂S(O)₂CH₃ and the like. The term "alkenyl", alone or in combination, means a straight-chain or branched-chain hydrocarbon radial having one or more double bonds and containing preferably from 2 to 10 carbon atoms, more preferably from 2 to 8 carbon atoms, most preferably from 2 to 5 carbon atoms. Examples of suitable alkenyl radicals include ethenyl, propenyl, 2-methylpropenyl, 1,4-butadienyl and the like. The term "alkynyl", alone or in combination, means a straight-chain or branched chain hydrocarbon radical having one or more triple bonds and containing preferably from 2 to 10 carbon atoms, more preferably from 2 to 5 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains preferably from 3 to 8 carbon atom ring members, more preferably from 3 to 7 carbon atom ring members, most preferably from 5 to 6 carbon atom ring members, and which may optionally be a benzo fused ring system which is optionally substituted as defined herein with respect to the definition of aryl. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as naphthyl and β-carbolinyl, and substituted ring systems, such as biphenyl, phenylpyridyl, naphthyl and diphenylpiperazinyl. The term "cycloalkylalkyl" means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like. The term "aryl", alone or in combination, means a phenyl or naphthyl radical which is optionally substituted with one or more substituents selected from alkyl, alkoxy, halogen, hydroxy, amino, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl and the like. Examples of aryl radicals are phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like. The terms "aralkyl" and "aralkoxy", alone or in combination, means an alkyl or alkoxy radical as defined above in which at least one hydrogen atom is replaced by an aryl radical as defined above, such as benzyl, benzyloxy, 2-phenylethyl, dibenzylmethyl, hydroxyphenylmethyl, methylphenylmethyl, diphenylmethyl, diphenylmethoxy, 4-methoxyphenylmethoxy and the like. The term "aralkoxycarbonyl", alone or in combination, means a radical of the formula aralkyl-O—C(O)— in which the term "aralkyl" has the significance given above. Examples of an aralkoxycarbonyl radical are benzyloxycarbonyl and 4-methoxyphenylmethoxycarbonyl. The term "aryloxy" means a radical of the formula aryl-O— in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl radical of the formula cycloalkyl-C(O)— in which the term "cycloalkyl" has the significance give above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl and the like. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" means an acyl radical derived from an arylcarboxylic acid, "aryl" having the meaning given above. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The terms "heterocyclo," alone or in combination, means a saturated or partially unsaturated monocyclic, bicyclic or tricyclic heterocycle radical containing at least one nitrogen, oxygen or sulfur atom ring member; preferably, 1-4 nitrogen, oxygen or sulfur atom ring member; more preferably, 0-4 nitrogen, 0-2 oxygen and 0-2 sulfur atom ring member, but at least one such heteroatom; and having preferably 3 to 8 ring members in each ring, more preferably 3 to 7 ring members in each ring and most preferably 5 to 6 ring members in each ring. "Heterocyclo" is intended to include sulfones, sulfoxides, N-oxides of tertiary nitrogen ring members, and carbocyclic fused and benzo fused ring systems. Such heterocyclo radicals may be optionally substituted on one or more carbon atoms by halogen, alkyl, alkoxy, hydroxy, oxo, aryl, aralkyl, heteroaryl, heteroaralkyl, amidino, N-alkylamidino, alkoxycarbonylamino, alkylsulfonylamino and the like, and/or on a secondary nitrogen atom (i.e., —NH—) by hydroxy, alkyl, aralkoxycarbonyl, alkanoyl, heteroaralkyl, phenyl or phenylalkyl and/or on a tertiary nitrogen atom (i.e., =N—) by oxido. "Heterocycloalkyl" means an alkyl radical as defined above in which at least one hydrogen atom is replaced by a heterocyclo radical as defined above, such as pyrrolidinylmethyl, tetrahydrothienylmethyl, pyridylmethyl and the like. The term "heteroaryl", alone or in combination, means an aromatic heterocyclo radical as defined above, which is optionally substituted as defined above with respect to the definitions of aryl and heterocyclo. Examples of such heterocyclo and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, (e.g., 2-(1-piperidinyl)pyridyl and 2-(4-benzyl piperazin-1-yl-1-pyridinyl, etc.), pyrazinyl, pyrimidinyl, furyl, tetrahydrofuryl, thienyl, tetrahydrothienyl and its sulfoxide and sulfone derivatives, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-, 2-, 4- or 5-benzimidazolyl, methylenedioxyphen-4-yl, methylenedioxyphen-5-yl, ethylenedioxyphenyl, benzothiazolyl, benzopyranyl, benzofuryl, 2,3-dihydrobenzofuryl, benzoxazolyl, thiophenyl and the like. The term "heteroatom" means a nitrogen, oxygen or sulfur atom. The term "cycloalkylalkoxycarbonyl" means an acyl group derived from a cycloalkylalkoxycarboxylic acid of the formula cycloalkylalkyl-O—COOH wherein cycloalkylalkyl has the meaning given above. The term "aryloxyalkanoyl" means an acyl radical of the formula aryl-O-alkanoyl wherein aryl and alkanoyl have the meaning given above. The term "heterocycloalkoxycarbonyl" means an acyl group derived from heterocycloalkyl-O—COOH wherein heterocycloalkyl is as defined above. The term "heterocycloalkanoyl" is an acyl radical derived from a heterocycloalkylcarboxylic acid wherein heterocyclo has the meaning given above. The term "heterocycloalkoxycarbonyl" means an acyl radical derived from a heterocycloalkyl-O—COOH wherein heterocyclo has the meaning given above. The term "heteroaryloxycarbonyl" means an acyl radical derived from a carboxylic acid represented by heteroaryl-O—COOH wherein heteroaryl has the meaning given above. The term "aminocarbonyl" alone or in combination, means an amino-substituted carbonyl (carbamoyl) group wherein the amino group can be a primary, secondary or tertiary amino group containing substituents selected from alkyl, aryl, aralkyl, cycloalkyl, cycloalkylalkyl radicals and the like. The term "aminoalkanoyl" means an acyl group derived from an amino-substituted alkylcarboxylic acid wherein the amino group can be a primary, secondary or tertiary amino group containing substituents selected from alkyl, aryl, aralkyl, cycloalkyl, cycloalkylalkyl radicals and the like. The term "halogen" means fluorine, chlorine, bromine or iodine. The term "haloalkyl" means an alkyl radical having the meaning as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term "leaving group" (L) generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate. The term "amino acid side chain" means the side chain group, including the stereochemistry of the carbon to which it is attached, attached to the naturally occurring amino acid which distinguishes the amino acid from glycine. For example, the amino acid side chain of alanine is methyl, of histidine is imidazolylmethyl and phenylalanine is benzyl, and the attachment of such side chains to the compound of this invention retain the naturally occurring stereochemistry of the carbon to which it is attached. The following example illustrates the definition:

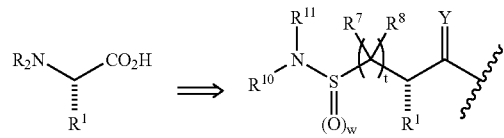

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R). However, such procedures are generally applicable to those compounds of opposite configuration, e.g., where the stereochemistry about the hydroxyl group is (S). In addition, the compounds having the (R) stereochemistry of the hydroxyl group can be utilized to produce those having the (S) stereochemistry. A compound having the (R) stereochemistry of the hydroxyl group can be inverted to the (S) stereochemistry using well-known methods. For example, the hydroxy group can be converted into a leaving group such as a mesylate or tosylate and reacting the leaving group with an oxide anion such as hydroxide, benzyloxide (followed by debenzylation) and the like, to produce an hydroxyl group with an (S) stereochemistry.

Preparation of Compounds of Formula I

The compounds of the present invention represented by Formula I above can be prepared utilizing the following general procedure. This procedure is schematically shown in the following Schemes I-III:

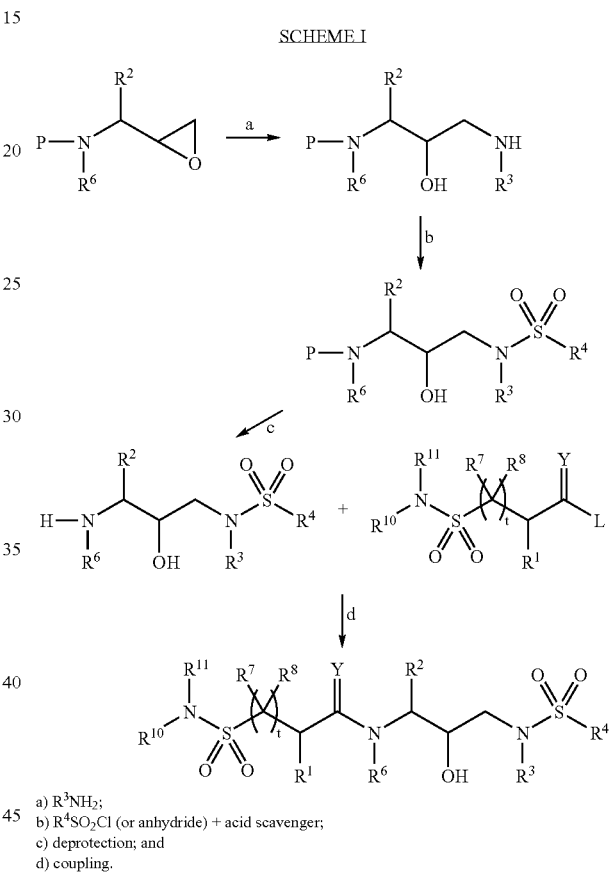

a) $R^3NH_2$;
b) $R^4SO_2Cl$ (or anhydride) + acid scavenger;
c) deprotection; and
d) coupling.

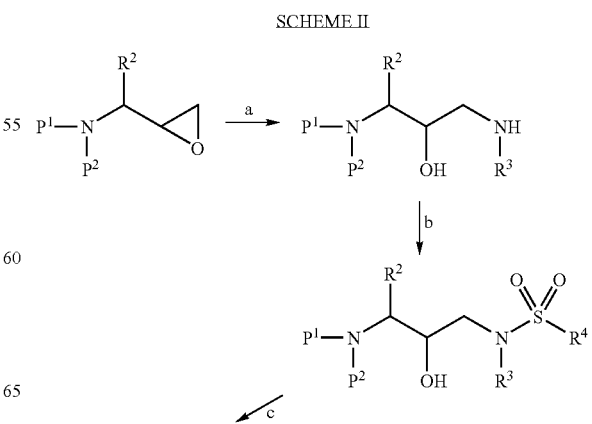

-continued

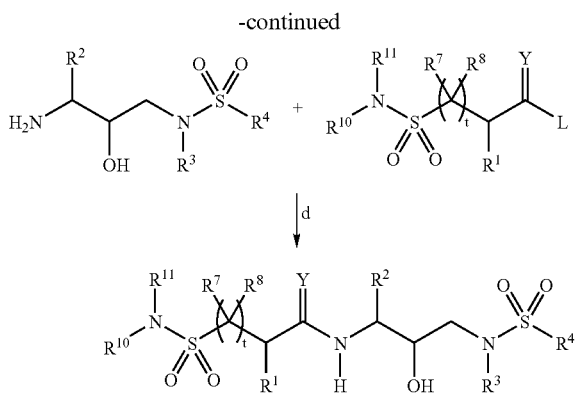

a) R³NH₂;
b) R⁴SO₂Cl (or anhydride) + acid scavenger;
c) deprotection; and
d) coupling.

SCHEME III

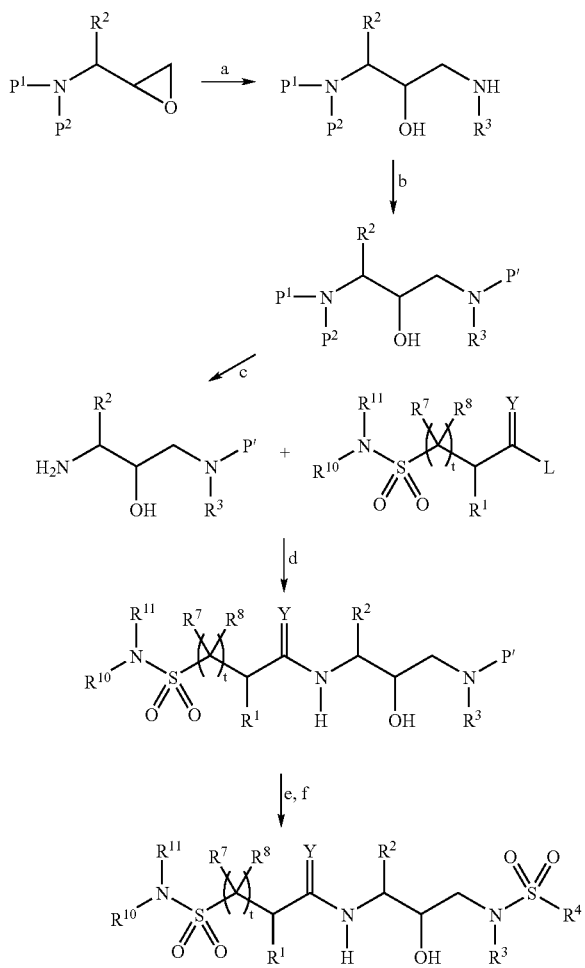

a) R³NH₂;
b) protection;
c) deprotection;
d) coupling;
e) deprotection; and
f) R⁴SO₂Cl (or anhydride).

An N-protected chloroketone derivative of an amino acid having the formula:

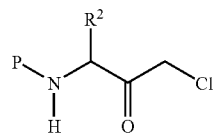

wherein P represents an amino protecting group, and $R^2$ is as defined above, is reduced to the corresponding alcohol utilizing an appropriate reducing agent. Suitable amino protecting groups are well known in the art and include carbobenzoxy, t-butoxycarbonyl, and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. Alternatively, the corresponding N-protected bromoketone can also be used and is especially useful for producing some chiral alcohols. The N-protected chloroketones are commercially available, e.g., such as from Bachem, Inc., Torrance, Calif. Alternatively, the chloroketones can be prepared by the procedure set forth in S. J. Fittkau, *J. Prakt. Chem.*, 315, 1037 (1973), and subsequently N-protected utilizing procedures which are well known in the art.

The halo alcohol can be utilized directly, as described below, or, preferably, is then reacted, preferably at room temperature, with a suitable base in a suitable solvent system to produce an N-protected amino epoxide of the formula:

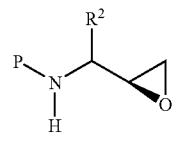

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared, such as in co-owned and co-pending PCT Patent Application Ser. No. PCT/US93/04804 which is incorporated herein by reference, starting with an L-amino acid which is reacted with a suitable amino-protecting group in a suitable solvent to produce an amino-protected L-amino acid ester of the formula:

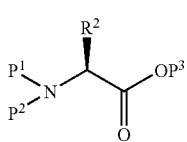

wherein P³ represents carboxyl-protecting group, e.g., methyl, ethyl, benzyl, tertiary-butyl and the like; R² is as defined above; and P¹ and P² independently are selected from amine protecting groups, including but not limited to, arylalkyl, substituted arylalkyl, cycloalkenylalkyl and substituted cycloalkenylalkyl, allyl, substituted allyl, acyl, alkoxycarbonyl, aralkoxycarbonyl and silyl. Examples of arylalkyl include, but are not limited to benzyl, ortho-methylbenzyl, trityl and benzhydryl, which can be optionally substituted with halogen, alkyl of $C_1$-$C_8$, alkoxy, hydroxy, nitro, alkylene, amino, alkylamino, acylamino and acyl, or their salts, such as phosphonium and ammonium salts. Examples of aryl groups include phenyl, naphthalenyl, indanyl, anthracenyl, durenyl, 9-(9-phenylfluorenyl) and phenanthrenyl, cycloalkenylalkyl or substituted cycloalkenylalkyl radicals containing cycloalkyls of $C_6$-$C_{10}$. Suitable acyl groups include carbobenzoxy, t-butoxycarbonyl, iso-butoxycarbonyl, benzoyl, substituted benzoyl, butyryl, acetyl, tri-fluoroacetyl, tri-chloroacetyl, phthaloyl and the like.

Additionally, the p¹ and/or p² protecting groups can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl. The term silyl refers to a silicon atom optionally substituted by one or more alkyl, aryl and aralkyl groups.

Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of the amine functions to provide mono- or bis-disilylamine can provide derivatives of the aminoalcohol, amino acid, amino acid esters and amino acid amide. In the case of amino acids, amino acid esters and amino acid amides, reduction of the carbonyl function provides the required mono- or bis-silyl aminoalcohol. Silylation of the aminoalcohol can lead to the N,N,O-tri-silyl derivative. Removal of the silyl function from the silyl ether function is readily accomplished by treatment with, for example, a mtal hydroxide or ammonium flouride reagent, either as a discrete reaction step or in situ during the preparation of the amino aldehyde reagent. Suitable silylating agents are, for example, trimethylsilyl chloride, tert-buty-dimethylsilyl chloride, phenyldimethylsilyl chloride, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Preferably P¹ and P² are independently selected from aralkyl and substituted aralkyl. More preferably, each of P¹ and P² is benzyl. As illustrated in the Examples below, P, P¹ and P² may serve as a nitrogen protecting group which is later removed in the preparation of compounds of this invention or may form a part of the final inhibitor structure. For example, benzoyl, benzyloxycarbonyl, t-butoxycarbonyl, pyridylmethoxycarbonyl, tetrahydrofuryloxycarbonyl, tetrahydrothiophene-S,S-dioxideoxycarbonyl, pyridylcarbonyl and the like can be used to both protect a nitrogen from undergoing an undesired reaction and also be part of the structure of an active enzyme inhibitor.

The amino-protected L-amino acid ester is then reduced, to the corresponding alcohol. For example, the amino-protected L-amino acid ester can be reduced with diisobutylaluminum hydride at −78° C. in a suitable solvent such as toluene. Preferred reducing agents include lithium aluminium hydride, lithium borohydride, sodium borohydride, borane, lithium tri-ter-butoxyaluminum hydride, borane/THF complex. Most preferably, the reducing agent is diisobutylaluminum hydride (DiBAL-H) in toluene. The resulting alcohol is then converted, for example, by way of a Swern oxidation, to the corresponding aldehyde of the formula:

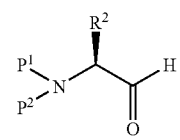

wherein P¹, P² and R² are as defined above. Thus, a dichloromethane solution of the alcohol is added to a cooled (−75 to −68° C.) solution of oxalyl chloride in dichloromethane and DMSO in dichloromethane and stirred for 35 minutes.

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydro thiophene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutyl chloroformate and DMSO. The oxidation conditions reported by Reetz et al [*Angew Chem.*, 99, p. 1186, (1987)], *Anaew Chem. Int. Ed. Engl.*, 26, p. 1141, 1987) employed oxalyl chloride and DMSO at −78° C.

The preferred oxidation method described in this invention is sulfur trioxide pyridine complex, triethylamine and DMSO at room temperature. This system provides excellent yields of the desired chiral protected amino aldehyde usable without the need for purification i.e., the need to purify kilograms of intermediates by chromatography is eliminated and large scale operations are made less hazardous. Reaction at room temperature also eliminated the need for the use of low temperature reactor which makes the process more suitable for commercial production.

The reaction may be carried out under an inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2,6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted [either P¹ or P²=H] or N,N-disubstituted aldehyde.

In addition, hydride reduction of an amide or ester derivative of the corresponding alkyl, benzyl or cycloalkenyl nitrogen protected phenylalanine, substituted phenylalanine or cycloalkyl analog of phenyalanine derivative can be carried out to provide the aldehydes. Hydride transfer is an additional method of aldehyde synthesis under conditions where aldehyde condensations are avoided, cf, Oppenauer oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −35° C. to about 45° C., and preferably from abut 5° C. to about 25° C. In the case of liquid amonia, the preferred temperature is about −33° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

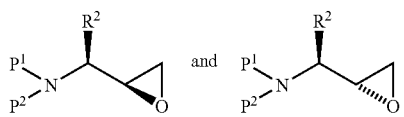

The diastereomers can be separated e.g., by chromatography, or, alternatively, once reacted in subsequent steps the diastereomeric products can be separated. For compounds having the (S) stereochemistry, a D-amino acid can be utilized in place of the L-amino acid.

The addition of chloromethylithium or bromomethylithium to a chiral amino aldehyde is highly diastereoselective. Preferably, the chloromethyllithium or bromomethylithium is generated in-situ from the reaction of the dihalomethane and n-butyllithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane, ethylene dichloride, methylene chloride can be used as pure solvents or as a mixture. Dipolar aprotic solvents such as acetonitrile, DMF, N-methylpyrrolidone are useful as solvents or as part of a solvent mixture. The reaction can be carried out under an inert atmosphere such as nitrogen or argon. For n-butyl lithium can be substituted other organometalic reagents reagents such as methyllithium, tert-butyl lithium, sec-butyl lithium, phenyllithium, phenyl sodium and the like. The reaction can be carried out at temperatures of between about −80° C. to 0° C. but preferably. between about −80° C. to −20° C. The most preferred reaction temperatures are between −40° C. to −15° C. Reagents can be added singly but multiple additions are preferred in certain conditions. The preferred pressure of the reaction is atmospheric however a positive pressure is valuable under certain conditions such as a high humidity environment.

Alternative methods of conversion to the epoxides of this invention include substitution of other charged methylenation precurser species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of this invention into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tosylate, methyl mesylate, methyl triflate, ethyl bromide, isopropyl bromide, benzyl chloride or the like, in the presence of an organic or inorganic base Alternatively, the protected aminosulfide alcohol can be alkylated with, for example, the alkylating agents above, to provide a sulfonium salts that are subsequently converted into the subject epoxides with tert-amine or mineral bases.

The desired epoxides formed, using most preferred conditions, diastereoselectively in ratio amounts of at least about an 85:15 ratio (S:R). The product can be purified by chromatography to give the diastereomerically and enantiomerically pure product but it is more conveniently used directly without purification to prepare retroviral protease inhibitors. The foregoing process is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenylalaninol and the like, or resolution can occur at intermediate or final steps. Chiral auxiliaries such as one or two equivilants of camphor sulfonic acid, citric acid, camphoric acid, 2-methoxyphenylacetic acid and the like can be used to form salts, esters or amides of the compounds of this invention. These compounds or derivatives can be crystallized or separated chromatographically using either a chiral or achiral column as is well known to those skilled in the art.

The amino epoxide is then reacted, in a suitable solvent system, with an equal amount, or preferably an excess of, a desired amine of the formula $R^3NH_2$, wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-(NHR$^3$)-propan-2-ol derivative (hereinafter referred to as an amino alcohol) can be represented by the formulas:

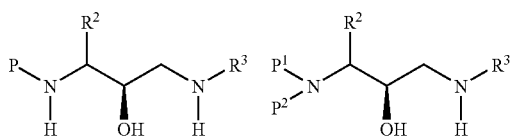

wherein P, $P^1$, $P^2$, $R^2$ and $R^3$ are as described above. Alternatively, a haloalcohol can be utilized in place of the amino epoxide.

The amino alcohol defined above is then reacted in a suitable solvent with a sulfonyl chloride ($R^4SO_2Cl$) or sulfonyl anhydride in the presence of an acid scavenger. Suitable solvents in which the reaction can be conducted include methylene chloride, tetrahydrofuran. Suitable acid scavengers include triethylamine, pyridine. Preferred sulfonyl chlorides are methanesulfonyl chloride and benzenesulfonyl chloride. The resulting sulfonamide derivative can be represented, depending on the epoxide utilized by the formulas

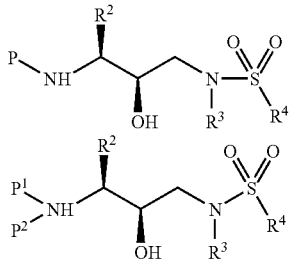

wherein P, $P^1$, $P^2$, $R^2$, $R^3$ and $R^4$ are as defined above. These intermediates are useful for preparing inhibitor compounds of the present invention and are also active inhibitors of retroviral proteases.

The sulfonyl halides of the formula $R^4SO_2X$ can be prepared by the reaction of a suitable Grignard or alkyl lithium reagent with sulfuryl chloride, or sulfur dioxide followed by oxidation with a halogen, preferably chlorine. Also, thiols may be oxidized to sulfonyl chlorides using chlorine in the presence of water under carefully controlled conditions. Additionally, sulfonic acids may be converted to sulfonyl halides using reagents such as $PCl_5$, and also to anhydrides using suitable dehydrating reagents. The sulfonic acids may in turn be prepared using procedures well known in the art. Such sulfonic acids are also commercially available. In place of the sulfonyl halides, sulfinyl halides ($R^4SOX$) or sulfenyl halides ($R^4SX$) can be utilized to prepare compounds wherein the —$SO_2$— moiety is replaced by an —SO— or —S— moiety, respectively.

Alternatively, the sulfonyl halides of the formula $R^4SO_2X$ can be prepared by well known procedures for chlorosulfonation of an aromatic compound, for example, reaction with chlorosulfonic acid or sulfur trioxide/N,N-dimethylformamide complex under suitable reaction conditions. See Wolf et al, *Z. Chem.* 7:20, 1967, 8:111, 1968; Culbertson et al, *J. Chem. Soc.*, p. 992 (1968) and EP 254577.

Following preparation of the sulfonamide derivative, the amino protecting group P or $P^1$ and $P^2$ amino protecting groups are removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Following neutralization of the salt, the amine is then reacted with an carboxylic acid, thiocarboxylic acid or corresponding derivative thereof represented by the formula

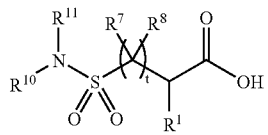

wherein t, $R^1$, $R^7$, $R^8$, $R^{10}$ and $R^{11}$ are as defined above, to produce the antiviral compounds of the present invention having the formula:

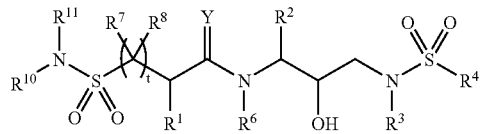

wherein t, $R^1$, $R^2$, $R^3$, $R^4$, $R^6$, $R^7$, $R^8$, $R^{10}$ and $R^{11}$ are as defined above. Preferred protecting groups in this instance are a benzyloxycarbonyl group or a t-butoxycarbonyl group.

Alternatively, the coupling order may be reversed as shown in Scheme III. The protected amino alcohol from the epoxide opening can be further protected at the newly introduced amino group with a protecting group P' which is not removed when the first protecting P is removed. One skilled in the art can choose appropriate combinations of P and P'. one suitable choice is when P is Cbz and P' is Boc. The resulting compound represented by the formulas

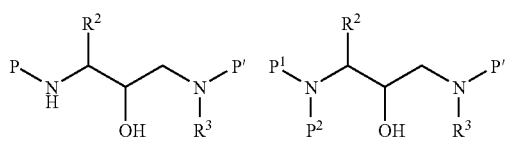

can be carried through the remainder of the synthesis to provide a compound of the formula

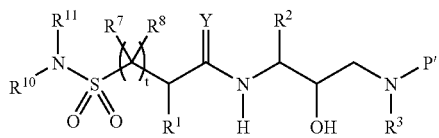

and the new protecting group P' is selectively removed, and following deprotection, the resulting amine reacted to form the sulfonamide derivative as described above. This selective deprotection and conversion to the sulfonamide can be accomplished at either the end of the synthesis or at any appropriate intermediate step if desired.

Protected S-acetylthioalkylcarboxylic acids can be utilized to prepare the sulfonamidealkylcarboxylic acids starting material of this invention. The protected S-acetylthioalkylcarboxylic acids can be oxidized in the presence of chlorine to form the corresponding sulfonyl chloride compounds. The sulfonyl chloride can then be reacted in the presence of a proton scavenger with $R^{10}R^{11}NH$ to produce the corresponding protected aminosulfonylalkylcarboxylic acids. After deprotection, the carboxylic acids can be utilized to prepare the compounds of this invention. Reactive groups, such as alcohols, thiols, primary amines, secondary amines and the like, which are present on groups $R^1$, $R^7$, $R^{10}$ and $R^{11}$ should be protected and deprotected as needed. The overall reaction sequence can be shown as follows

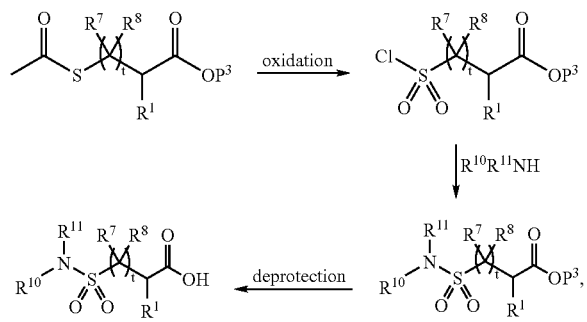

wherein $R^1$, $R^7$, $R^8$, $R^{10}$, $R^{11}$ and $P^3$ are as defined above. This process can also be used in the asymmetric synthesis of starting materials having asymmetric centers.

The protected S-acetylthioalkylcarboxylic acids can be readily prepared using standard procedures from the corresponding substituted S-acetylthioalkylcarboxylic acids

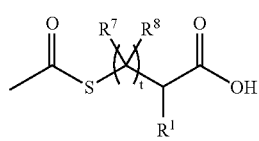

or can be readily prepared by acetylating the corresponding substituted thiols

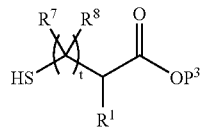

with acetic anhydride, acetyl chloride or the like using standard conditions. Such substituted thiols can be readily prepared from commercially available starting materials using standard procedures and reagents well known in the art. For example, a carbonyl can be readily converted into a thiocarbonyl which can be reduced to a thiol or reacted with a nucleophile to form a substituted thiol. Alternatively, a carboxylic acid or ester having a leaving group, such as chlorine atom, bromine atom, tosylate, mesylate and the like, can be reacted with sulfide anion, benzylthiol followed by debenzylation, thiocyanide anion followed by decyanation, and the like, to form the thiol, or with thioacetate anion to form the acetylthio derivative. In addition, Michael addition of sulfide anion on this acetate to a double bond containing carboxylic acid or protected carboxylic acid can provide the desired thioalkyl carboxylic acid. Substituted thioalkylcarboxylic acids having chiral centers can be prepared from sugars using standard synthetic methods, or by resolution of the carboxylic acids using resolving reagents or resolving chromatographic columns.

The thiocarbonyl compounds of this invention are really prepared by methods well known to those skilled in the art, for example, by treatment of a carbonyl compound with Lawesson's reagent (2,4-bis(4-methoxyphenyl)-1,3-dithia-2,4-diphosphetane-2,4-disulfide) which is an article of commerce. Phosphorus pentasulfide may also be used or one can treat an amine of this invention with a pre-formed thiocarbonyl reagent such as thiocarbonylchloride in the presence of base.

In place of the sulfonyl halides, sulfinyl halides (RSOCl) and sulfenyl halides (RSCl) can be utilized to prepare compounds wherein the $—SO_2—$ moiey is replaced by $—SO—$ or $—S—$, respectively.

It is contemplated that for preparing compounds of the Formulas having $R^6$, the compounds can be prepared following the procedures set forth above and, prior to coupling the sulfonamide-carboxylic acid derivative

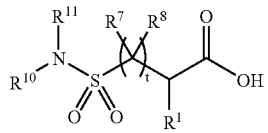

to the protected amine or sulfonamide amine

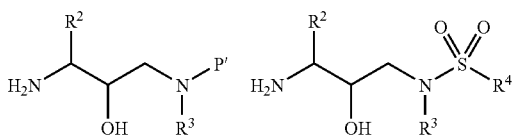

by alkylation or reductive amination. For example, the amino group can be alkylated with sodium cyanoborohydride and an appropriate aldehyde or ketone at room temperature. It is also contemplated that where $R^3$ of the amino alcohol intermediate is hydrogen, the inhibitor compounds of the present invention wherein $R^3$ is alkyl, or other substituents wherein the α-C contains at least one hydrogen, can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties, such as tautomers thereof as well as compounds, wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples illustrate the preparation of the inhibitor compounds of the present invention which inhibit, in particular, HIV protease and intermediates useful in the preparation of the inhibitor compounds. In addition, the intermediates can also inhibit retroviral proteases.

EXAMPLE 1

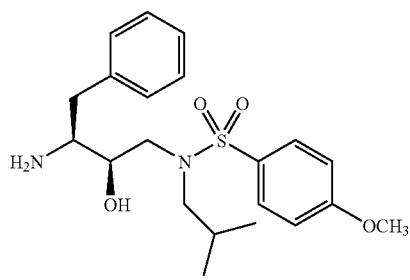

Preparation of 3S-amino-1-[N-(2-methylpropyl)-N-(4-methoxyphenylsulfonyl)amino]-4-phenyl-2R-butanol Part A: N-benzyloxycarbonyl-3(S)-amino-1-chloro-4-phenyl-2(S)-butanol To a solution of N-benzyloxycarbonyl-L-phenylalanine chloromethyl ketone (75 g, 0.2 mol) in a mixture of 800 mL of methanol and 800 mL of tetrahydrofuran was added sodium borohydride (13.17 g, 0.348 mol, 1.54 equiv.) over 100 min. The solution was stirred at room temperature for 2 hours and then concentrated in vacuo. The residue was dissolved in 1000 mL of ethyl acetate and washed with 1N $KHSO_4$, saturated aqueous $NaHCO_3$, saturated aqueous NaCl, dried over anhydrous $MgSO_4$, filtered and concentrated in vacuo to give an oil. The crude product was dissolved in 1000 mL of hexanes at 60° C. and allowed to cool to room temperature where upon crystals formed that were isolated by filtration and washed with copious amounts of hexanes. This solid was then recrystallized from hot ethyl acetate and hexanes to provide 32.3 g 43% of N-benzyloxycarbonyl-3(S)-amino-1-chloro-4-phenyl-2(S)-butanol, mp 150-151° C., FAB MS: $MLi^+$=340.

Part B: 3(S)-[N-(benzyloxycarbonyl)amino]-1,2(S)-epoxy-4-phenylbutane

A solution of potassium hydroxide (6.52 g. 0.116 mol, 1.2 equiv.) in 970 mL of absolute ethanol was treated with N-benzyloxycarbonyl-3(S)-amino-1-chloro-4-phenyl-2(S)-butanol (32.3 g, 0.097 mol). This solution was stirred at room temperature for 15 minutes and then concentrated in vacuo to give a white solid. The solid was dissovled in dichloromethane and washed with water, dried over anhyd $MgSO_4$, filetered and concentrated in vacuo to give a white solid. The solid was crystallized from hexanes and ethyl acetate to give 22.3 g, 77% of 3(S)-[N-(benzyloxycarbonyl)amino]-1,2(S)-epoxy-4-phenylbutane, mp 102-103° C., FAB MS: $MH^+$=298.

Part C: N-[3(S)-benzyloxycarbonylamino-2(R)-hydroxy-4-phenyl]N-isobutylamine

A solution of N-benzylcarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(S)-benzyloxycarbonylamino-2(R)-hydroxy-4-phenyl]-N-isobutylamine, mp 108.0-109.5° C., MH+ m/z=371.

Part D: phenylmethyl [2(R)-hydroxy-3-[N-(2-methylpropyl)-N-(4-methoxyphenylsulfonyl)amino]-1S-(phenylmethyl)propyl]carbamate The amine from Part C (936.5 mg, 2.53 mmol) and triethylamine (2.88.5 mg, 2.85 mmol) was dissolved in 20 mL of dichloromethane and treated with 4-methoxybenzenesulfonyl chloride (461 mg, 2.61 mmol). The solution was stirred at room temperature for 16 hours and then concentrated in vacuo. The residue was dissolved in ethyl acetate and this solution was washed with 1N $KHSO_4$, saturated aqueous $NaHCO_3$, brine, dried over anhyd $MgSO_4$, filtered, and concentrated to give a clear oil 1.234 g. The oil was crystallized from a mixture of ether and hexanes, 729.3 mg, 56.5% mp 95-99° C., FAB MS: $MH^+$=511.

Part E: 3S-amino-1-[N-(2-methylpropyl)-N-(4-methoxyphenylsulfonyl)amino]-4-phenyl-2R-butanol A solution of phenylmethyl [2(R)-hydroxy-3-[N-(2-methylpropyl)-N-(4-methoxyphenylsulfonyl)amino]1-S-(phenylmethyl) propyl carbamate (671.1 mg, 1.31 mmol) from Part D in 10 mL of methanol was hydrogenated over 50 mg of 10% palladium on carbon at 40 psig at room temperature for 15 hours. The catalyst was removed by filtration through diatomaceous earth and the filtrate concentrated to give a white foam, 474.5 mg, 96%, FAB MS: MH$^+$=377.

EXAMPLE 2

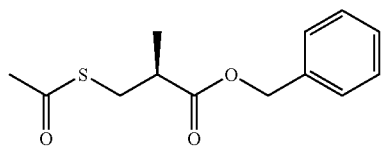

Preparation of benzyl D-(-)-S-acetyl-β-mercaptoisobutyrate

A 250 mL round bottom flask equipped with N$_2$ inlet, magnetic stir bar, and addition funnel was charged with 14 g D-(-)-S-acetyl-β-mercaptoisobutyric acid and 125 mL dry toluene and cooled to 0° C. To the stirring solution was added 13.6 g (1.0 eq) DBU dropwise over 20 minutes then 15.3 g (1.05 eq) benzyl bromide over about 5 minutes. The reaction was allowed to warm to room temperature overnight. The reaction was concentrated in vacuo and partition between ethyl acetate/saturated aqueous bicarbonate. The organic phase was washed with brine, dried, and concentrated in vacuo to 20.6 g (95%) benzyl D-(-)-S-acetyl-β-mercaptoisobutyrate suitable for use in the next step.

EXAMPLE 3

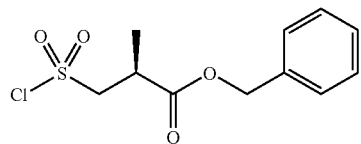

Preparation of benzyl 3-chlorosulfonyl-2(R)-methylpropionate

A 500 mL round bottom flask was charged with 20.6 g crude product from Example 2, in 200 mL 10% ethanolic carbon tetrachloride. The solution was cooled to 0° C. and chlorine gas was bubbled through for 90 minutes. The reaction was concentrated in vacuo to yield 22.5 g pale yellow benzyl 3-chlorosulfonyl-2(R)-methylpropionate that is suitable for use without further purification.

EXAMPLE 4

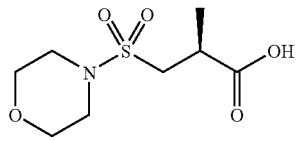

Preparation of 3-(1-morpholinosulfonyl)-2(R)-methylpropionic acid

Part A: benzyl 3-(1-morpholinosulfonyl)-2(R)-methylpropionate

A 100 mL round bottom flask equipped with magnetic stir bar and N$_2$ inlet was charged with 1.1 g benzyl 3-chlorosulfonyl-2(R)-methylpropionate from Example 3, in 10 mL CH$_2$Cl$_2$. The solution was cooled to 0° C. and mixed with 0.67 mL (1.2 eq) NEt$_3$ and 0.36 mL (1.05 eq) morpholine in 15 mL CH$_2$Cl$_2$. The reaction was stirred at 0° C. for 3 hours. The reaction was concentrated in vacuo and the residue was partioned between ethyl acetate/H$_2$O. The organic phase was washed with brine, dried and concentrated in vacuo to yield 10 g (77%) of a white crystalline solid of benzyl 3-(1-morpholinosulfonyl)-2(R)-methylpropionate.

Part B: 3-(1-morpholinosulfonyl)-2(R)-methylpropionic acid

A 100 mL Fisher/Porter vessel was charged with 1.0 g benzyl 3-(1-morpholinosulfonyl)-2(R)-methylpropionate in 15 mL MeOH and a catalytic amount of 10% Pd—C and hydrogenated overnight at 40 psi. The next day the reaction was filtered through Celite and concentrated in vacuo to yield 750 mg of 3-(1-morpholinosulfonyl)-2(R)-methylpropionic acid. HRMS calcd. for C$_8$H$_{15}$NO$_5$S calcd. 238.0748, obs 238.0760.

EXAMPLE 5

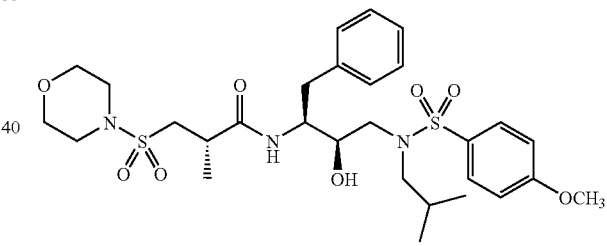

Preparation of N$^1$-[1-[N-(2-methyloropyl)-N-(4-methoxyphenylsulfonyl)amino]-2R-hydroxy-3(S)-(phenylmethyl)prop-3-yl]-3-(1-morpholinosulfonyl)-2(R)-methylpropionamide A 50 mL round bottom flask equipped with magnetic stir bar was charged with 125 mg of 3-(1-morpholinosulfonyl)-2(R)-methylpropionic acid from Example 4 in 5 mL DMF. The solution was cooled to 0° C. and 107 mg (1.5 eq) HOBT was added followed by 112 mg (1.1 eq) EDC. After 30 minutes, 200 mg of amine from Example 1 (0.93 eq) in 2 mL DMF was added and the reaction was stirred at room temperature overnight. The reaction was concentrated in vacuo and the residue was taken up in ethyl acetate and washed with saturated aqueous bicarbonate, 5% aquious citric acid, brine, dried over MgSO$_4$ and concentrated to yield 207 mg (67%) of N$^1$-[1-[N-(2-methylpropyl)-N-(4-methoxyphenylsulfonyl)amino]-2R-hydroxy-3(S)-(phenylmethyl)prop-3-yl]-3-(1-morpholinosulfonyl)-2(R)-methylpropionamide. The product was further purified by flash

EXAMPLE 6

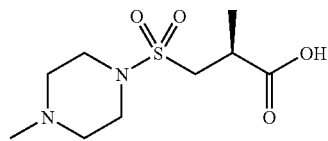

Preparation of 3-(4-methylpiperizin-1-ylsulfonyl)-2(R)-methylpropionic acid

Part A: benzyl 3-[(4-methylpiperizin-1-yl)sulfonyl]-2(R)-methylpropionate

A 100 mL round bottom flask equipped with magnetic stir bar was charged with 0.42 mL (1.05 eq) N-methyl-piperazine, 1 mL NEt$_3$ and 20 mL CH$_2$Cl$_2$. The solution was cooled to 0° C. and 1.0 g of benzyl 3-chlorosulfonyl-2(R)-methylpropionate from Example 3 in 5 mL CH$_2$Cl$_2$ was added. After 1 hour reaction was concentrated in vacuo. The residue was partioned between EA/H$_2$O and the organic phase was washed with saturated aqueous bicarb., brine, dried, and concentrated in vacuo to yield benzyl 3-[(4-methylpiperizin-1-yl)sulfonyl]-2(R)-methylpropionate which was used without further purification.

Part B: 3-[(4-methylpiperizin-1-yl)sulfonyl]-2(R)-methylpropionic acid

A 100 mL Fisher/Porter vessel was charged with benzyl 3-[(4-methylpiperizin-1-yl)sulfonyl]-2(R)-methylpropionate in 15 mL MeOH with a catalytic amount of 10% Pd—C. Hydrogenation at 50 psi for 48 hours afforded, after filtration through Celite and concentration in vacuo to yield 3-[(4-methylpiperizin-1-yl)sulfonyl]-2(R)-methylpropionic acid as a hygroscopic foam suitable for use without further purification.

EXAMPLE 7

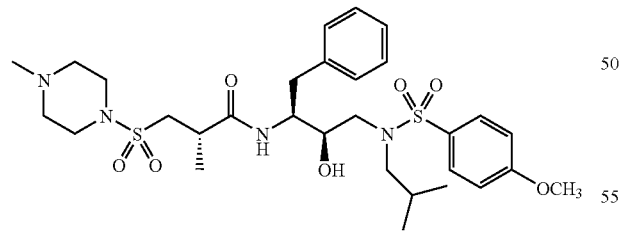

Preparation of N$^1$-[1-[N-(2-methylpropyl)-N-(4-methoxyphenylsulfonyl)amino]-2R-hydroxy-3(S)-(phenylmethyl)prop-3-yl]-3-[(4-methylpiperizin-1-yl)sulfonyl]-2(R)-methylpropionamide A 100 mL round bottom flask equipped with magnetic stir bar and N$_2$ inlet was charged with 79 mg of 3-[(4-methylpiperizin-1-yl)sulfonyl]-2(R)-methylpropionic acid from Example 6 (1.15 eq) in 5 mL DMF. The solution was cooled to 0° C. and 55 mg (1.5 eq) HOBt was added followed by 61 mg (1.15 eq) EDC. After 30 minutes a solution of 110 mg amine from Example 1 in 1 mL DMF was added and the reaction was stirred at room temperature. The reaction was poured into H$_2$O and the product extracted with ethyl acetate. The organic phase was washed with saturated aqeous bicarbonate, brine, dried and concentrated in vacuo to yield crude product. Purification by flash chromatography (CH$_2$Cl$_2$/MeOH) yielded 100 mg (57%) of N$^1$-[1-[N-(2-methylpropyl)-N-(4-methoxyphenylsulfonyl)amino]-2R-hydroxy-3(S)-(phenylmethyl)prop-3-yl]-3-[(4-methylpiperizin-1-yl)sulfonyl]-2(R)-methylpropionamide.

EXAMPLE 8

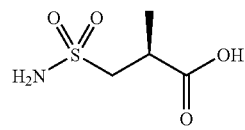

Preparation of 3-aminosulfonyl-2(R)-methylpropionic acid

Part A: benzyl 3-aminosulfonyl-2(R)-methylpropionate

A 100 mL round bottom flask equipped with magnetic stir bar was charged with 1.22 g of benzyl 3-chlorosulfonyl-2(R)-methylpropionate in 15 mL CH$_2$Cl$_2$ and cooled to −78° C. To this solution was added to 10 mL of liquid ammonia at −78° C. After 20 minutes the reaction was warmed to room temperature, concentrated in vacuo to afford a white solid. The solid was slurried in ethyl acetate, filtered to remove inorganic salts and concentrated in vacuo to afford 1.08 g of benzyl 3-aminosulfonyl-2(R)-methylpropionate as a clear yellow oil. The crude product was used without further purification.

Part B: 3-aminosulfonyl-2(R)-methylpropionic acid

A 100 mL Fisher/Porter vessel was charged with 1.1 g of crude benzyl 3-aminosulfonyl-2(R)-methylpropionate in 35 mL MeOH and a catalytic amount of 10% Pd—C. The mixture was hydrogenated at 50 psi for 24 hours, filtered through Celite and concentrated in vacuo to yield 700 mg of 3-aminosulfonyl-2(R)-methylpropionic acid as a clear oil. The crude acid was used without further purification.

EXAMPLE 9

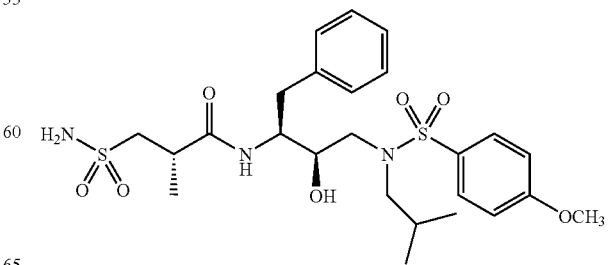

chromatography (ethyl acetate/hexanes). HRMS calcd. for C$_{29}$H$_{43}$N$_3$O$_8$S$_2$; calcd. 626.2570, obs. 626.2584.

Preparation of $N^1$-[1-[N-(2-methylpropyl)-N-(4-methoxyphenylsulfonyl)amino]-2R-hydroxy-3(S)-(phenylmethyl)prop-3-yl]-3-aminosulfonyl-2(R)-methylpropionamide A 25 mL round bottom flask equipped with magnetic stir bar and $N_2$ inlet was charged with 70 mg of 3-aminosulfonyl-2(R)-methylpropionic acid from Example 8 in 2 mL DMF. The solution was cooled to 0° C. and charged with 74 mg (1.5 eq) HOBt, and 80 mg (1.15 eq) EDC. After 15 minutes a solution of 147 mg of amine from Example 1 in 2 mL DMF was added. The reaction was stirred 20 hours at room temperature and partitioned between ethyl acetate and saturated aqueous bicarbonate. The organic phase was washed with brine, dried and concentrated in vacuo to yield 160 mg of crude oil. The crude material was dissolved in ethyl acetate, washed with 10% aq $KHSO_4$ and concentrated in vacuo to yield 80 mg crude product. Purification by flash chromatography (MeOH/ethyl acetate) on silica gel afforded 35 mg of $N^1$-[1-[N-(2-methylpropyl)-N-(4-methoxyphenylsulfonyl)amino]-2R-hydroxy-3(S)-(phenylmethyl)prop-3-yl]-3-aminosulfonyl-2(R)-methylpropionamide. HRMS calcd. for $C_{24}H_{36}N_3O_7S_2$; calcd. 556.2151, obs. 556.2198.

EXAMPLE 10

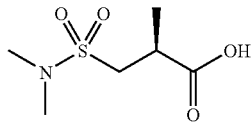

Preparation of
3-[(dimethylamino)sulfonyl]-2(R)-methylpropionic acid

Part A: benzyl 3-[(dimethylamino)sulfonyl]-2(R)-methylpropionate

A 100 mL round bottomed flask equipped with magnetic stir bar was charged with 1.7 g benzyl 3-chlorosulfonyl-2(R)-methylpropionate from Example 3 in 25 mL $CH_2Cl_2$. The solution was cooled to −78° C. and 15 mL of anhydrous dimethylamine was slowly added. After 30 minutes the reaction was concentrated in vacuo and the residue was partioned between $EA/H_2O$. The organic phase was dried, concentrated in vacuo to yield 1.4 g of benzyl 3-[(dimethylamino)sulfonyl]-2(R)-methylpropionate as a clear amber oil which was used directly in the next step.

Part B: 3-[(dimethylamino)sulfonyl]-2(R)-methylpropionic acid

A 100 mL Fisher/Porter vessel was charged with 1.4 g of benzyl 3-[(dimethylamino)sulfonyl]-2(R)-methylpropionate in 30 mL acetic acid with a catalytic amount of 10% Pd—C. The reaction was hydrogenated at 50 psi for 24 hours, filtered through Celite and concentrated in vacuo. The residue was azeotroped with toluene then concentrated in vacuo to afford 900 mg of 3-[(dimethylamino)sulfonyl]-2(R)-methylpropionic acid which was used without further purification.

EXAMPLE 11

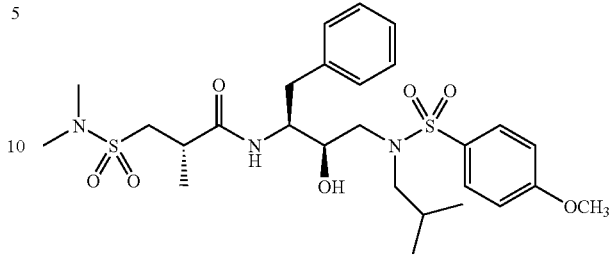

Preparation of $N^1$-[1-[N-(2-methylpropyl)-N-(4-methoxyphenylsulfonyl)amino]-2R-hydroxy-3(S)-(phenylmethyl)prop-3-yl]-3-[(dimethylamino)sulfonyl]-2(R)-methylpropionamide A 50 mL round bottom flask equipped with magnetic stir bar was charged with 126 mg of 3-[(dimethylamino)sulfonyl]-2(R)-methylpropionic acid from Example 10 in 2 ML DMF. The solution was cooled to 0° C. and 110 mg (1.5 eq) HOBt was added followed by 124 mg (1.15 eq) EDC. After 30 minutes, 236 mg of amine from Example 1 in 3 mL DMF was added. The reaction was stirred at room temperature overnight. The reaction was partitioned between ethyl acetate and saturated aqueous bicarbonate. The organic phase was washed with brine, dried and concentrated in vacuo to yield 220 mg crude product. Flash chromatography (3% $MeOH/CH_2Cl_2$) on silica gel gave 84 mg (25%) of $N^1$-[1-[N-(2-methylpropyl)-N-(4-methoxyphenylsulfonyl) amino]-2R-hydroxy-3(S)-(phenylmethyl)prop-3-yl]-3-[(dimethylamino)sulfonyl]-2(R)-methylpropionamide. HPLC indicators 99.2% pure. HRMS calcd. for (M+Li) $C_{27}H_{41}N_3O_7S_2$: calcd. (M+Li) 590.2546, obs (m+Li) 590.2599.

EXAMPLE 12

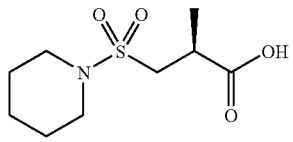

Preparation of
3-(1-piperidinyl)sulfonyl-2(R)-methylpropionic acid

Part A: benzyl 3-(1-piperidinyl)sulfonyl-2(R)-methylpropionate

A 100 mL round bottom flask equipped with magnetic stir bar was charged with 1 g benzyl 3-chlorosulfonyl-2(R)-methylpropionate from Example 3 in 25 mL $CH_2Cl_2$. The solution was cooled to 0° C. and 4 mL of piperdine was slowly added. The reaction was stirred 1 hour then concentrated in vacuo. The residue was partioned between ethyl acetate and water. The organic phase was washed with brine, dried, and concentrated in vacuo to give 1 g of benzyl 3-(1-piperidinyl)sulfonyl-2(R)-methylpropionate suitable for use without further purification.

Part B: 3-(1-piperidinyl)sulfonyl-2(R)-methylpropionic acid

A 100 mL Fisher/Porter vessel was charged with 1 g of benzyl 3-(1-piperidinyl)sulfonyl-2(R)-methylpropionate 30 mL MeOH and a catalytic amount of 10% Pd—C. The reaction was hydrogenated at 50 psi for 3 hours. After filtration through Celite and concentration in vacuo of 3-(1-piperidinyl)sulfonyl-2(R)-methylpropionic acid was isolated in quantitive yield.

EXAMPLE 13

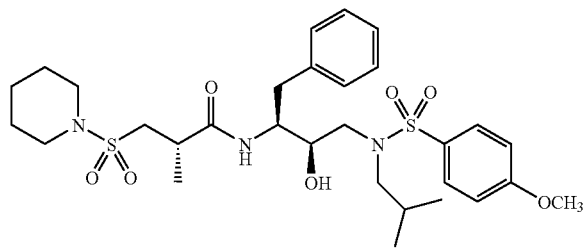

Preparation of $N^1$-[1-[N-(2-methypropyl)-N-(4-methoxyphenylsulfonyl)amino]-2R-hydroxy-3(S)-(phenylmethyl)prop-3-yl]-3-(1-piperidinyl)sulfonyl-2(R)-methylpropionamide A 50 mL round bottom flask equipped with magnetic stir bar was charged with 100 mg of 3-(1-piperidinyl)sulfonyl-2(R)-methylpropionic acid in 3 mL DMF. The solution was cooled to 0° C. and 75 mg (1.5 eq) HOBt added followed by 82 mg (1.15 g) EDC. After 30 minutes, 172 mg of amine from Example 1 in mL DMF was added. The reaction was stirred 20 hours at room temperature then partitioned between ethyl acetate and saturated aqueous bicarbonate. The organic phase was washed with brine, dried, and concentrated in vacuo to yield 180 mg of crude product. Flash chromatography yielded 60 mg of $N^1$-[1-[N-(2-methylpropyl)-N-(4-methoxyphenylsulfonyl)amino]-2R-hydroxy-3(S)-(phenylmethyl)prop-3-yl]-3-(1-piperidinyl)sulfonyl-2(R)-methylpropionamide. HRMS calcd. for $C_{30}H_{45}N_3O_7S_2O$: calcd. 624.2777, obs. 624.2753.

EXAMPLE 14

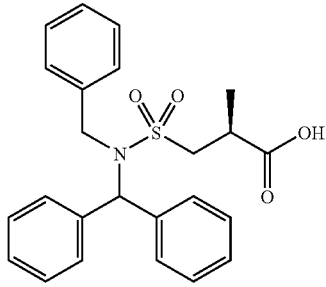

Preparation of 3-[N-(benzyl)-N-(diphenylmethyl)aminosulfonyl]-2(R)-methylpropionic acid Part A: methyl 3-[N-(diphenylmethyl)aminosulfonyl]-2(R)-methylpropionate A 100 mL round bottom flask equipped with magnetic stir bar was charged with 1 g aminodiphenylmethane, 2 mL triethylamine in 20 mL $CH_2Cl_2$. The reaction was cooled to 0° C. and 1 g of methyl 3-chlorosulfonyl-2(R)-methylpropionate was slowly added. The reaction was stirred 1 hour then concentrated in vacuo. The residue was partioned between ethyl acetate and water. The organic phase was washed with brine, dried, and concentrated in vacuo. Trituration from $Et_2O$/hexanes gave 1.15 g of methyl 3-[N-(diphenylmethyl)aminosulfonyl]-2(R)-methylpropionate as a white solid. HRMS (M+Li): calcd. 354.1351, obs 354.1569.

Part B: methyl 3-[N-(benzyl)-N-(diphenylmethyl)aminosulfonyl]-2(R)-methylpropionate A 100 mL round bottom flask equipped with magnetic stir bar and $N_2$ inlet was charged with 1.11 g of methyl 3-[N-(diphenylmethyl)aminosulfonyl]-2(R)-methylpropionate, 447 mg $K_2CO_3$, 347 mL benzyl bromide in 20 mL DMF. The reaction was stirred overnight, concentrated in vacuo and partioned between ethyl acetate and water. The organic phase was washed with brine, dried and concentrated in vacuo to 1.2 g of a clear oil. Flash chromatography on silica gel (30% ethyl acetate/hexanes) afforded 730 mg of methyl 3-[N-(benzyl)-N-(diphenylmethyl)aminosulfonyl]-2(R)-methylpropionate. HRMS (M+Li): calcd. 444.1821, obs 444.1865.

Part C: 3-[N-(benzyl)-N-(diphenylmethyl)aminosulfonyl]-2(R)-methylpropionic acid A 50 mL round bottom flask equipped with magnetic stir bar was charged with 320 mg of methyl 3-[N-(benzyl)-N-(diphenylmethyl)aminosulfonyl]-2(R)-methylpropionate and 120 mg LiOH (4 eq) in 4 mL 50% aq THF. After 5 minutes 2 mL MeOH added to get homogeneous solution, after 1 hour the reaction was partioned between ethyl acetate and 5% aq $KHSO_4$. The organic phase was washed with brine, dried, and concentrated in vacuo to yield 250 mg of 3-[N-(benzyl)-N-(diphenylmethyl)aminosulfonyl]-2(R)-methylpropionic acid as a clear semi-solid. HRMS (M+Li): calcd. 430.1664, obs. 430.1698.

EXAMPLE 15

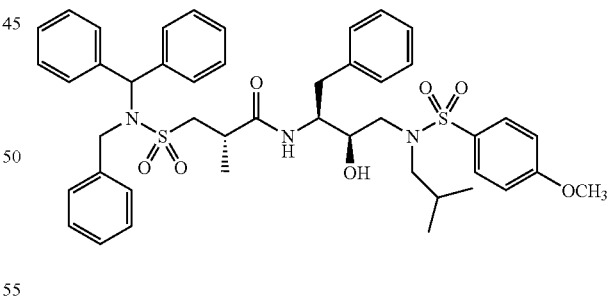

Preparation of $N^1$-[1-[N-(2-methylpropyl)-N-(4-methoxyphenylsulfonyl)amino]-2R-hydroxy-3(S)-(phenylmethyl)prop-3-yl]-3-[N-(benzyl)-N-(diphenylmethyl)aminosulfonyl]-2(R)-methylpropionamide A 50 mL round bottom flask equipped with magnetic stir bar was charged with 240 mg of 3-[N-(benzyl)-N-(diphenylmethyl)aminosulfonyl]-2(R)-methylpropionic acid in 4 mL DMF. The solution was cooled to 0° C. and 100 mg HOBt followed by 110 mg EDC. After 30 minutes a solution of 205 mg amine from Example 1 in 3 mL DMF was added. After 20 hours at room temperature this reaction mixture was partioned between ethyl acetate and saturated aqueous bicarbonate. The organic phase was washed with 5% aq. citric acid, brine, dried and concentrated in vacuo to yield 430 mg of a foam. Flash chromatography on silica gel (40% ethyl acetate/hexanes) gave 350 mg of $N^1$-[1-[N-(2-methylpropyl)-N-(4-methoxyphenylsulfonyl)amino]-2R-hydroxy-3(S)-(phenylmethyl)prop-3-yl]-3-[N-(benzyl)-N-(diphenylmethyl)aminosulfonyl]-2(R)-methylpropionamide. HRMS (M+Li): calcd. 818.3485, obs. 818.3550.

EXAMPLE 16

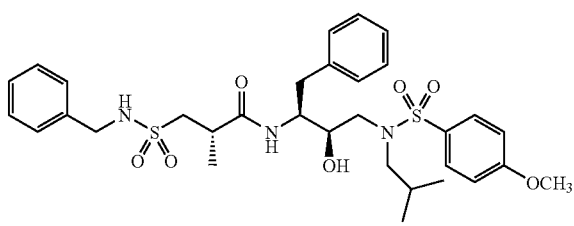

Preparation of $N^1$-[1-[N-(2-methylpropyl)-N-(4-methoxyphenylsulfonyl)amino]-2R-hydroxy-3(S)-(phenylmethyl)prop-3-yl]-3-[N-(benzyl)aminosulfonyl]-2(R)-methylpropionamide A 100 mL Fisher/Porter vessel was charged with 340 mg of $N^1$-[1-[N-(2-methylpropyl)-N-(4-methoxyphenylsulfonyl)amino]-2R-hydroxy-3(S)-(phenylmethyl)prop-3-yl]-3-[N-(benzyl)-N-(diphenylmethyl)aminosulfonyl]-2(R)-methylpropionamide in 25 mL MeOH, and a catalytic amount of 10% Pd—C. The reaction was hydrogenated at 50 psi for 2 hours. After filtration through Celite the residue was flash chromatographed on silica gel (100% H->100% EA) to afford 170 mg of $N^1$-[1-[N-(2-methylpropyl)-N-(4-methoxyphenylsulfonyl)amino]-2R-hydroxy-3(S)-(phenylmethyl)prop-3-yl]-3-[N-(benzyl)aminosulfonyl]-2(R)-methylpropionamide. HRMS (M+Li): calcd. 652.2703, obs. 652.2747.

EXAMPLE 17

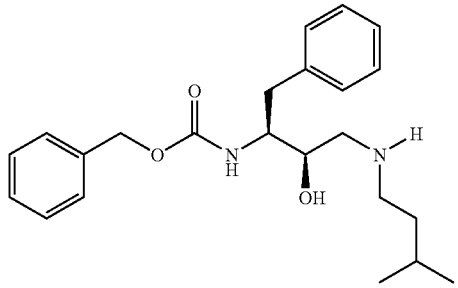

Preparation of N[3(S)-benzyloxycarbonylamino-2(R)-hydroxy-4-phenylbutyl]-N-isoamylamine Part A:
To a solution of 75.0 g (0.226 mol) of N-benzyloxycarbonyl-L-phenylalanine chloromethyl ketone in a mixture of 807 mL of methanol and 807 mL of tetrahydrofuran at -2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150-151° C. and M+Li$^+$=340.

Part B:
To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate; filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102-103° C. and MH$^+$ 298.

Part C:
A solution of N-benzyloxycarbonyl 3(S)-amino-1,2-(S)-epoxy-4-phenylbutane (1.00 g, 3.36 mmol) and isoamylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(3-methylbutyl)]amine mp 108.0-109.5° C., MH$^+$ m/z=371.

EXAMPLE 18

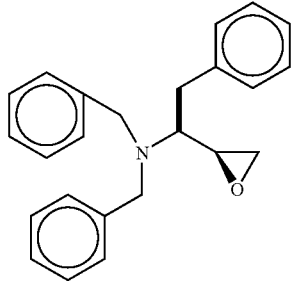

Preparation of N,N-dibenzyl-3(S)-amino-1,2(S)-epoxy-4-phenylbutane

Step A:
A solution of L-pherylalanine (50.0 g, 0.302 mol), sodium hydroxide (24.2 g, 0.605 mol) and potassium carbonate (83.6 g, 0.605 mol) in water (500 ml) was heated to 97° C. Benzyl bromide (108.5 ml, 0.912 mol) was then slowly added (addition time ~25 min). The mixture was then stirred at 97° C. for 30 minutes. The solution was cooled to room temperature and extracted with toluene (2×250 ml). The combined organic layers were then washed with water, brine, dried over magnesium sulfate, filtered and concentrated to give an oil product. The crude product was then used in the next step without purification.

Step B:

The crude benzylated product of the above step was dissolved in toluene (750 ml) and cooled to −55° C. A 1.5 M solution of DIBAL-H in toluene (443.9 ml, 0.666 mol) was then added at a rate to maintain the temperature between −55° to −50° C. (addition time—1 hour). The mixture was stirred for 20 minutes at −55° C. The reaction was quenched at −55° C. by the slow addition of methanol (37 ml). The cold solution was then poured into cold (5° C.) 1.5 N HCl solution (1.8 L). The precipitated solid (approx. 138 g) was filtered off and washed with toluene. The solid material was suspended in a mixture of toluene (400 ml) and water (100 ml). The mixture was cooled to 5° C., treated with 2.5 N NaOH (186 ml) and then stirred at room temperature until the solid was dissolved. The toluene layer was separated from the aqueous phase and washed with water and brine, dried over magnesium sulfate, filtered and concentrated to a volume of 75 ml (89 g). Ethyl acetate (25 ml) and hexane (25 ml) were then added to the residue upon which the alcohol product began to crystallize. After 30 min., an additional 50 ml hexane was added to promote further crystallization. The solid was filtered off and washed with 50 ml hexane to give approximately 35 g of material. A second crop of material could be isolated by refiltering the mother liquor. The solids were combined and recrystallized from ethyl acetate (20 ml) and hexane (30 ml) to give, in 2 crops, approximately 40 g (40% from L-phenylalanine) of analytically pure alcohol product. The mother liquors were combined and concentrated (34 g). The residue was treated with ethyl acetate and hexane which provided an additional 7 g (~7% yield) of slightly impure solid product. Further optimization in the recovery from the mother liquor is probable.

Alternatively, the alcohol was prepared from L-phenylalaninol. L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60-68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnite to give a semi-dry solid (407 g) which was recrystallized from 1.1 L of ethyl acetate/heptane (1:10 by volume). The product was isolated by filtration (at −8° C. ), washed with 1.6 L of cold (−10° C.) ethyl acetate/heptane (1:10 by volume) and air-dried to give 339 g (88% yield) of βS-2-[Bis(phenylmethyl)amino]benzene-propanol, mp 71.5-73.0° C. More product can be obtained from the mother liquor if necessary. The other analytical characterization was identical to compound prepared as described above.

Step C:

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time −1.25 hr). The mixture was stirred for 5 min. followed by addition of a solution of the alcohol (0.074 mol) in 100 ml of dichloromethane (addition time −20 min., temp. −75° C. to −68° C.). The solution was stirred at −78° C. for 35 minutes. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give the desired aldehyde product. The aldehyde was carried on to the next step without purification.

Temperatures higher than −70° C. have been reported in the literature for the Swern oxidation. Other Swern modifications and alternatives to the Swern oxidations are also possible.

Alternatively, the aldehyde was prepared as follows. (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8-17° C. (addition time—1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenced with 1.6 L of cold water (10-15° C.) over 45 minutes. The resultant solution was extracted with ethyl acetate (2.0 L), washed with 5% citric acid (2.0 L), and brine (2.2 L), dried over $MgSO_4$ (280 g) and filtered. The solvent was removed on a rotary evaporator at 35-40° C. and then dried under vaccuum to give 198.8 g of αS-[Bis-(phenylmethyl)amino]-benzenepropanaldehyde as a pale yellow oil (99.9%). The crude product obtained was pure enough to be used directly in the next step without purification. The analytical data of the compound were consistent with the published literature. $[\alpha]_D 25 = -92.9°$ (c 1.87, $CH_2Cl_2$);

$^1$H NMR (400 MHz, $CDCl_3$) ∂, 2.94 and 3.15 (ABX-System, 2H, $J_{AB}$=13.9 Hz, $J_{AX}$=7.3 Hz and $J_{BX}$=6.2 Hz), 3.56 (t, 1H, 7.1 Hz), 3.69 and 3.82 (AB-System, 4H, $J_{AB}$=13.7 Hz), 7.25 (m, 15 H) and 9.72 (S, 1H); HRMS calcd for (M+1) $C_{23}H_{24}NO$ 330.450, found: 330.1836. Anal. Calcd. for $C_{23}H_{23}ON$: C, 83.86; H, 7.04; N, 4.25. Found: C, 83.64; H, 7.42; N, 4.19. HPLC on chiral stationary phase: (S,S) Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enantiomer 10.62 min.

Step D:

A solution of αS-[Bis(phenylmethyl)amino]benzene-propanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6 M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyllithium (110 mL) at <−25° C. After addition the mixture was stirred at −30 to −35° C. for 10 minutes. This was repeated once. (2) Additional chloroiodomethane (8.5 mL, 0.11 mol) was added, followed by n-butyllithium (55 mL, 0.088 mol) at <−25° C. After addition, the mixture was stirred at −30 to −35° C. for 10 minutes. This was repeated 5 times. (3) Additional chloroiodomethane (8.5 mL, 0.11 mol) was added, followed by n-butyllithium (37 mL, 0.059 mol) at <−25° C. After addition, the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N,αS-Tris(phenylmethyl)-2S-oxiranemethanamine $^1$H NMR (400 MHz, CDCl$_3$) ∂ 2.49 and 2.51 (AB-System, 1H, J$_{AB}$=2.82), 2.76 and 2.77 (AB-System, 1H, J$_{AB}$=4.03), 2.83 (m, 2H), 2.99 & 3.03 (AB-System, 1H, J$_{AB}$=10.1 Hz), 3.15 (m, 1H), 3.73 & 3.84 (AB-System, 4H, J$_{AB}$=14.00), 7.21 (m, 15H); $^{13}$C NMR (400 MHz, CDCl$_3$) ∂ 139.55, 129.45, 128.42, 128.14, 128.09, 126.84, 125.97, 60.32, 54.23, 52.13, 45.99, 33.76; HRMS calcd for C$_{24}$H$_{26}$NO (M+1) 344.477, found 344.2003.

N,N,αS-Tris(phenylmethyl)-2R-oxiranemethanamine $^1$H NMR (300 MHz, CDCl$_3$) ∂ 2.20 (m, 1H), 2.59 (m, 1H), 2.75 (m, 2H), 2.97 (m, 1H), 3.14 (m, 1H), 3.85 (AB-System, 4H), 7.25 (m, 15H) HPLC on chiral stationary phase: Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of (8): 9.38 min., retention time of enanatiomer of (4): 13.75 min.

Alternatively, a solution of the crude aldehyde 0.074 mol and chloroiodomethane (7.0 ml, 0.096 mol) in tetrahydrofuran (285 ml) was cooled to −78° C., under a nitrogen atmosphere. A 1.6 M solution of n-butyllithium in hexane (25 ml, 0.040 mol) was then added at a rate to maintain the temperature at −75° C. (addition time—15 min.). After the first addition, additional chloroiodomethane (1.6 ml, 0.022 mol) was added again, followed by n-butyllithium (23 ml, 0.037 mol), keeping the temperature at −75° C. The mixture was stirred for 15 min. Each of the reagents, chloroiodomethane (0.70 ml, 0.010 mol) and n-butyllithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

Alternatively, a solution of αS-[Bis(phenylmethyl)amino] benzene-propanaldehyde (178.84 g, 0.54 mol) and bromochloromethane (46 mL, 0.71 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6 M, 340 mL, 0.54 mol) was then added at a rate that maintained the temperature below −25° C. After addition the mixture was stirred at −30 to −35° C. for 10 minutes. More additions of reagents were carried out in the following manner: (1) additional bromochloromethane (14 mL) was added, followed by n-butyllithium (102 mL) at <−25° C. After addition the mixture was stirred at −30 to −35° C. for 10 minutes. This was repeated once. (2) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated 5 times. (3) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material.

EXAMPLE 19

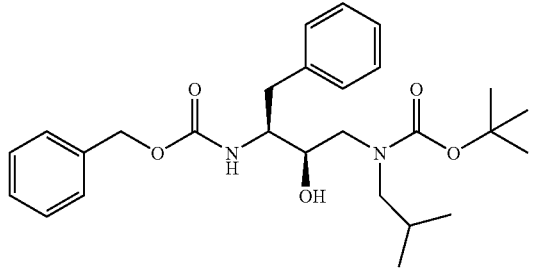

Preparation of N-[[3S-(phenylmethylcarbamoyl) amino]-2R-hydroxy-4-phenyl]-1-[(2-methylpropyl) amino-2-(1,1-dimethylethoxyl)carbonyl]butane To a solution of 7.51 g (20.3 mmol) of N-[[3S-(phenylmethylcarbamoyl)amino]-2R-hydroxy-4-phenylbutyl]-N-(2-methylpropyl)]amine in 67 mL of anhydrous tetrahydrofuran was added 2.25 g (22.3 mmol) of triethylamine. After cooling to 0° C., 4.4 g (20.3 mmol) of di-tert-butyldicarbonate was added and stirring continued at room temperature for 21 hours. The volatiles were removed in vacuo, ethyl acetate added, then washed with 5% citric acid, saturated sodium bicarbonate, brine, dried over magnesium sulfate, filtered and concentrated to afford 9.6 g of crude product. Chromatography on silica gel using 30% ethyl acetate/hexane afforded 8.2 g of pure N-[[(3S-(phenylmethylcarbamoyl)amino]-2R-hydroxy-4-phenyl]-1-[(2-methylpropyl)amino-2-(1,1-dimethylethoxy)carbonyl]butane, mass spectum m/e=477 (M+Li).

EXAMPLE 20

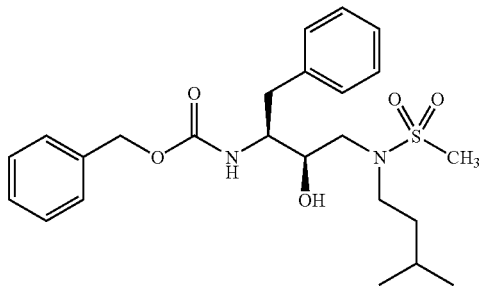

Preparation of phenylmethyl [2R-hydroxy-3-[(3-methylbutyl) (methylsulfonyl)amino]-1S-(phenylmethyl)propyl]carbamate To a solution of N[3(S)-benzyloxycarbonylamino-2(R)-hydroxy-4-phenylbutyl]N-isoamylamine (2.0 gm, 5.2 mmol) and triethylamine (723 uL, 5.5 mmol) in dichloromethane (20 mL) was added dropwise methanesulfonyl chloride (400 uL, 5.2 mmol). The reaction mixture was stirred for 2 hours at room temperature, then the dichloromethane solution was concentrated to ca. 5 mL and applied to a silica gel column (100 gm). The column was eluted with chloroform containing 1% ethanol and 1% methanol. The phenylmethyl [2R-hydroxy-3-[(3-methylbutyl)(methylsulfonyl)amino]-1S-(phenylmethyl)propyl]carbamate was obtained as a white solid Anal. Calcd for $C_{24}H_{34}N_2O_5S$: C, 62.31; H, 7.41; N, 6.06. Found: C, 62.17; H, 7.55; N, 5.97.

EXAMPLE 21

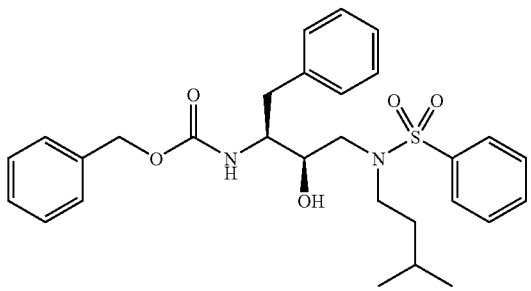

Preparation of phenylmethyl[2R-hydroxy-3-[(3-methylbutyl) (phenylsulfonyl)amino]-1S-(phenylmethyl)propyl]carbamate From the reaction of N[3(S)-benzyloxycarbonylamino-2(R)-hydroxy-4-phenylbutyl]N-isoamylamine (1.47 gm, 3.8 mmol), triethylamine (528 uL, 3.8 mmol) and benzenesulfonyl chloride (483 uL, 3.8 mmol) one obtains phenylmethyl [2R-hydroxy-3-[(3-methylbutyl) (phenylsulfonyl)amino]-1S-(phenylmethyl)propyl]-carbamate. Column chromatography on silica gel eluting with chloroform containing 1% ethanol afforded the pure product. Anal. Calcd for $C_{29}H_{36}N_2O_5S$: C, 66.39; H, 6.92; N, 5.34. Found: C, 66.37; H, 6.93; N, 5.26.

EXAMPLE 22

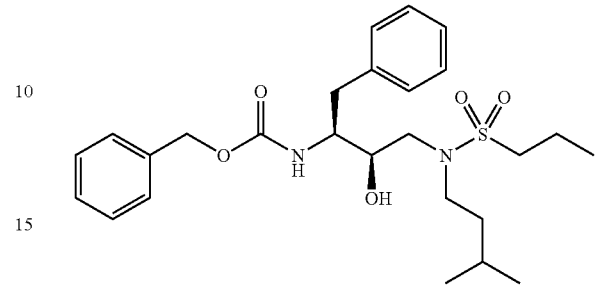

Preparation of Phenylmethyl [2R-hydroxy-3-[(3-methylbutyl) (n-propanesulfonyl)amino]-1S-(phenylmethyl)propyl]carbamate To a solution of N[3(S)-benzyloxycarbonylamino-2(R)-hydroxy-4-phenylbutyl]N-isoamylamine (192 mg, 0.5 mmol) and triethylamine (139 uL, 1.0 mmol) in dichloromethane (10 mL) was added dropwise trimethylsilyl chloride (63 uL, 0.5 mmol). The reaction was allowed to stir for 1 hour at room temperature, cooled to 0° C. with an ice bath and then n-propanesulfonyl chloride (56 uL, 0.5 mmol) was added dropwise. The reaction mixture was stirred for 1.5 hours at room temperature, then diluted with ethyl acetate (50 mL) and washed sequentially with 1N HCl, water, saturated sodium bicarbonate solution, and saturated sodium chloride solution (25 mL each). The organic solution was dried over magnesium sulfate, filtered and concentrated to an oil. The oil was stirred with methanol (10 mL) for 16 hours, concentrated and the residue chromatographed on silica gel (50 gm) eluting with 10% ethyl acetate in hexane (450 mL), then with 1:1 ethyl acetate/hexane. The phenylmethyl [2R-hydroxy-3-[(3-methylbutyl) (n-propanesulfonyl)amino]-1S-(phenylmethyl)propyl]carbamate was recrystallized from ethyl ether/hexane to afford a white solid Anal. Calcd. for $C_{26}H_{38}N_2O_5S$: C, 63.64; H, 7.81; N, 5.71. Found: C, 63.09; H, 7.74; N, 5.64.

EXAMPLE 23

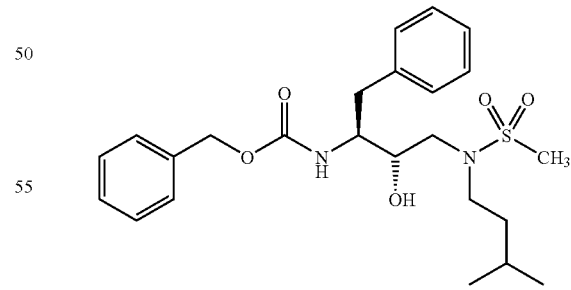

Preparation of phenylmethyl[2S-hydroxy-3-[(3-methylbutyl)(methylsulfonyl)amino]-1S-(phenylmethyl)propyl]carbamate To a solution of N-[3(S)-benzyloxycarbonylamino-2(S)-hydroxy-4-phenylbutyl]-N-isoamylamine (192 mg, 0.5 mmol) and triethylamine (139 uL, 0.55 mmol) in dichloromethane (8 mL) was added dropwise methanesulfonyl chloride (39 uL, 0.55 mmol). The reaction mixture was stirred for 16 hours at room temperature, then the dichloromethane solution was applied to a silica gel column (50 gm). The column was eluted with dichloromethane containing 2.5% methanol. The phenylmethyl [2S-hydroxy-3-[(3-methylbutyl) (methylsulfonyl)amino]-1S-(phenylmethyl) propyl]carbamate was obtained as a white solid Anal. Calcd. for $C_{24}H_{34}N_2O_5S \diamond 0.2\ H_2O$: C, 61.83; H, 7.44; N, 6.01. Found: C, 61.62; H, 7.40; N, 5.99.

EXAMPLE 24

Following the procedures of the previous Examples 1-23, the compounds set forth in Table 1A were prepared.

TABLE 1A

| Entry | $R^3$ | $R^4$ |
|---|---|---|
| 1 | isoamyl | p-fluorophenyl |
| 2 | isoamyl | p-nitrophenyl |
| 3 | isoamyl | o-nitrophenyl |
| 4 | isoamyl | β-naphthyl |
| 5 | isoamyl | 2-thienyl |
| 6 | isoamyl | benzyl |
| 7 | isobutyl | p-fluorophenyl |
| 8 | p-fluorobenzyl | phenyl |
| 9 | 4-pyridylmethyl | phenyl |
| 10 | cyclohexylmethyl | phenyl |
| 11 | allyl | phenyl |
| 12 | propyl | phenyl |
| 13 | cyclopropylmethyl | phenyl |
| 14 | methyl | phenyl |
| 15 | propargyl | phenyl |
| 16 | isoamyl | p-chlorophenyl |
| 17 | isoamyl | p-methoxyphenyl |
| 18 | isoamyl | m-nitrophenyl |
| 19 | isoamyl | m-trifluoromethylphenyl |
| 20 | isoamyl | o-methoxycarbonylphenyl |
| 21 | isoamyl | p-acetamidophenyl |
| 22 | isobutyl | phenyl |
| 23 | —$CH_2Ph$ | —Ph |
| 24 | —$CH_2$—(p-F-phenyl) | —Ph |
| 25 | —$CH_2$—cyclohexyl | —Ph |
| 26 | —$CH_2$—(p-OCH$_3$-phenyl) | —Ph |
| 27 | —$CH_2$—(3-pyridyl) | —Ph |
| 28 | —$CH_2$—cyclopropyl | —Ph |
| 29 | —$CH_2CH=CH_2$ | —Ph |
| 30 | phenyl | —Ph |
| 31 | cyclohexyl | —Ph |
| 32 | —$CH_2CH_2Ph$ | —Ph |
| 33 | —$CH_2CH_2CH_2OH$ | —Ph |
| 34 | —$CH_2CH_2N(CH_3)_2$ | —Ph |
| 35 | —$CH_2CH_2$-morpholino | —Ph |
| 36 | —$CH_3$ | —Ph |
| 37 | —$CH_2CH_2CH_2SCH_3$ | —Ph |
| 38 | —$CH_2CH_2CH_2S(O)_2CH_3$ | —Ph |
| 39 | —$CH_2CH_2CH(CH_3)_2$ | p-methylphenyl |
| 40 | —$CH_2CH_2CH(CH_3)_2$ | —$CH_2CH_2CH_3$ |
| 41 | —$CH_2CH_2CH(CH_3)_2$ | —$CH_3$ |
| 42 | —$CH_2CH_2CH(CH_3)_2$ | p-F-phenyl |
| 43 | —$CH_2CH_2CH(CH_3)_2$ | p-CH$_3$-phenyl |
| 44 | —$CH_2CH_2CH(CH_3)_2$ | o-CO$_2$CH$_3$-phenyl |
| 45 | —$CH_2CH(CH_3)_2$ | p-NO$_2$-phenyl |
| 46 | —$CH_2CH(CH_3)_2$ | p-NHAc-phenyl |
| 47 | —$CH_2CH(CH_3)_2$ | p-CH$_3$-phenyl |

TABLE 1A-continued

Structure:

| Entry | R³ | R⁴ |
|---|---|---|
| 48 | —CH₂CH₂CH₃ | 4-methoxyphenyl |
| 49 | —CH₂CH₂CH₂CH₃ | 4-methoxyphenyl |
| 50 | —CH₂CH₂CH(CH₃)₂ | —CF₃ |
| 51 | —CH₂CH(CH₃)₂ | —CH₃ |
| 52 | —CH₂CH₂CH(CH₃)₂ | —CH₂Cl |
| 53 | —CH₂CH(CH₃)₂ | —CH=CH—phenyl |
| 54 | —CH₂CH(CH₃)₂ | 4-methoxyphenyl |
| 55 | —CH₂CH(CH₃)₂ | —CH=CH₂ |
| 56 | —CH₂CH(CH₃)(CH₂CH₃) | 4-methoxyphenyl |
| 57 | —CH₂CH(CH₃)₂ | 4-ethoxyphenyl |
| 58 | —CH₂CH(CH₃)₂ | 4-CF₃-phenyl |
| 59 | —CH₂CH(CH₃)₂ | 4-Cl-phenyl |
| 60 | —CH₂CH(CH₃)₂ | 4-SCH₃-phenyl |
| 61 | —CH₂CH(CH₃)₂ | 4-SOCH₃-phenyl |
| 62 | —CH₂CH(CH₃)₂ | 4-SO₂CH₃-phenyl |
| 63 | —CH₂-(3-pyridyl) | p-methylphenyl |

EXAMPLE 25

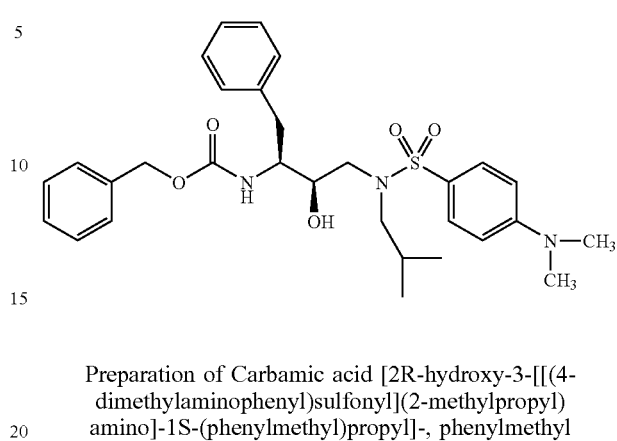

Preparation of Carbamic acid [2R-hydroxy-3-[[(4-dimethylaminophenyl)sulfonyl](2-methylpropyl)amino]-1S-(phenylmethyl)propyl]-, phenylmethyl ester To a solution of 100 mg (0.19 mmol) of carbamic acid, [2R-hydroxy-3-[[(4-fluorophenyl)sulfonyl](2-methylpropyl)amino]-1S-(phenylmethyl)propyl]-, phenylmethyl ester in 1 mL of pyridine was added 53 µL of triethylamine and 120 µL (p.95 mmol) of 40% aqueous dimethylamine. After heating for 24 hours at 100° C., the solution was cooled, ethyl acetate added, then washed with 5% citric acid, saturated sodium bicarbonate, dried over magnesium sulfate, filtered and concentrated. The resulting solid was recrystallized from ethyl acetate/hexane to afford 10 mg of the desired product; mass spectrum m/e=540 (M+H).

EXAMPLE 26

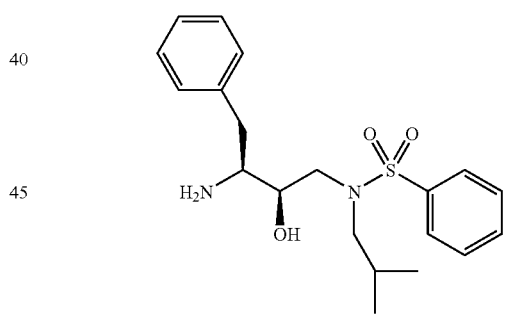

Preparation of 1-amino-2R-hydroxy-3-[(phenylsulfonyl)(2-methylpropyl)amino]-1S-(phenylmethyl)propane Part A:

A solution of N-benzyloxycarbonyl-3S-amino-1,2-S-epoxy-4-phenylbutane (50 g, 0.168 mol) and isobutylamine (246 g, 3.24 mol) in 650 mL of isopropyl alcohol was refluxed for 1.25 hours. The solution was cooled to room temperature, concentrated in vacuo and then poured into 1 L of stirring hexane whereupon the product crystallized from solution, was collected and air dried to give 57.6 g of N-[3S-benzyloxycarbonylamino-2R-hydroxy-4-phenyl]-N-isobutylamine, mp 108-109.5 C, mass spectrum m/e=371 (M+H).

Part B:

The amine from part A (0.94 g, 2.5 mmol) and triethylamine (288 mg, 2.85 mmol) in 20 mL of methylene chloride was treated with 461 mg (2.61 mmol) of benzenesulfonyl chloride. The solution was stirred at room temperature for 16 hours, concentrated, dissolved in ethyl acetate, then washed with 1N potassium hydrogen sulfate, saturated sodium bicarbonate, brine, dried over magnesium sulfate, filtered and concentrated to afford a clear oil. This was recrystallized from diethyl ether and hexane to afford 0.73 g of carbamic acid, [2R-hydroxy-3-[(phenylsulfonyl)(2-methylpropyl)amino]-1S-(phenylmethyl)propyl]-, phenylmethyl ester, mp 95-99 C, mass spectrum m/e=511 (M+H).

Part C:

A solution of 500 mg of carbamic acid, [2R-hydroxy-3-[(phenylsulfonyl)(2-methylpropyl)amino]-1S-(phenylmethyl)propyl]-, phenylmethyl ester in 20 mL of methanol was hydrogenated in the presence of 250 mg of a 10% palladium on carbon catalyst under 40 psig for 3 hours, the catalyst was removed by filtration, and the solution concentrated to afford 352 mg of [2R-hydroxy-3-[(phenylsulfonyl])2-methylpropyl)amino]-1S-(phenylmethyl) propylamine, mass spectrum m/e=377 (M+H), which was used directly in the next step without purification.

EXAMPLE 27

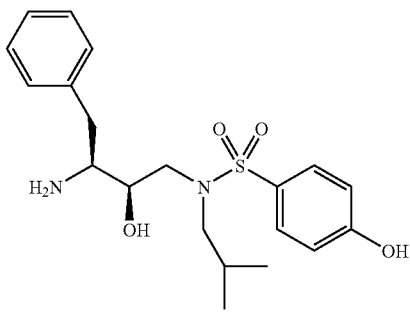

Preparation of 1-amino-2R-hydroxy-3-[[(4-hydroxyphenyl)sulfonyl](2-methylpropyl)amino]-1S-(phenylmethyl)propane Part A:

A solution of 0.98 g (1.85 mmol) of carbamic acid, [2R-hydroxy-3-[[(4-fluorophenyl)sulfonyl](2-methylpropyl)amino]-1S-(phenylmethyl)propyl]-phenylmethyl ester in 3.8 mL of anhydrous DMF was added to 22 mg (7.4 mmol) of 80% sodium hydride in 2 mL of DMF. To this mixture was added 0.40 g (3.7 mmol) of benzyl alcohol. After 2 hours; the solution was cooled to O C, water added, and then ethyl acetate. The organic layer was washed with 5% cirtic acid, saturated sodium bicarbonate and brine, dried over magnesium sulfate, filtered and concentrated to afford 0.90 g of crude material. This was chromatographed on basic alumina using 3% methanol/methylene chloride to afford 0.70 g of 2R-hydroxy-3-[(2-methylpropyl)(4-hydroxyphenyl)sulfonyl]amino-1S-(phenylmethyl)propylamine, cyclic carbamate; mass spectrum m/e=509 (M+H).

Part B:

To a solution of 0.65 g (1.28 mmol) of the cyclic carbamate from part A in 15 mL of ethanol, was added 2.6 mL (6.4 mmol) of 2.5N sodium hydroxide solution. After 1 hour at reflux, 4 mL of water was added and the solution refluxed for an additional eight hours. The volatiles were removed, ethyl acetate added, and washed with water, brine, dried over magnesium sulfate, filtered and concentrated to afford 550 mg of crude 2R-hydroxy-3-[(2-methylpropyl)(4-hydroxyphenyl)sulfonyl]amino-1S-(phenylmethyl)propylamine.

Part C:

A solution of crude 2R-hydroxy-3-[(2-methylpropyl)(4-benzyloxyphenyl)sulfonyl]amino-1S-(phenylmethyl)propylamine in 10 mL of ethanol was hydrogenated in the presence of 500 mg of a 10% palldium on carbon catalyst under 50 psig of hydrogen for 2 hours. The catalyst was removed by filtration and the solvent removed in vacuo to afford 330 mg of 2R-hydroxy-3-[(2-methylpropyl)(4-hydroxyphenyl)sulfonyl]amino-1S-(phenylmethyl)propylamine, mass spectrum m/e=393 (M+H).

EXAMPLE 28

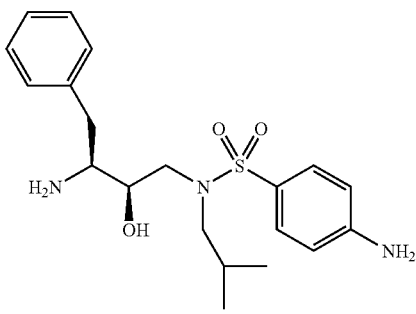

Preparation of 2R-hydroxy-3-[[(4-aminophenyl)sulfonyl](2-methylpropyl)amino]-1S-(phenylmethyl)propylamine Part A: Preparation of Carbamic acid, 2R-hydroxy-3-[[(4-nitrophenyl)sulfonyl](2-methylpropyl)amino]-1S-(phenylmethyl)propyl-, phenylmethyl ester To a solution of 4.0 g (10.8 mmol) of N-[3S-benzyloxycarbonylamino-2R-hydroxy-4-phenyl]-N-isobutylamine in 50 mL of anhydrous methylene chloride, was added 4.5 mL (3.27 g, 32.4 mmol) of triethylamine. The solution was cooled to 0° C. and 2.63 g (11.9 mmol) of 4-nitrobenzene sulfonyl chloride was added, stirred for 30 minutes at 0° C., then for 1 hour at room temperature. Ethyl acetate was added, washed with 5% citric acid, saturated sodium bicarbonate, brine, dried and concentrated to yield 5.9 g of crude material. This was recrystallized from ethyl acetate/hexane to afford 4.7 g of pure carbamic acid, [2R-hydroxy-3-[[(4-nitrophenyl)sulfonyl](2-methylpropyl)amino]-1S-(phenylmethyl)propyl-, phenylmethyl ester, m/e=556(M+H).

Part B: Preparation of 2R-hydroxy-3-[[(4-aminophenyl)sulfonyl](2-methylpropyl)amino]-1S-(phenylmethyl)propylamine A solution of 3.0 g (5.4 mmol) of carbamic acid, 2R-hydroxy-3-[[(4-nitrophenyl)sulfonyl](2-methylpropyl)amino]-1S-(phenylmethyl)propyl-, phenylmethyl ester in 20 mL of ethyl acetate was hydrogenated over 1.5 g of 10% palladium-on-carbon catalyst under 35 psig of hydrogen for 3.5 hours. The catalyst was removed by filtration and the solution concentrated to afford 2.05 g of the desired 2R-hydroxy-3-[[(4-aminophenyl)sulfonyl](2-methylpropyl)amino]-1S-(phenylmethyl)propylamine, m/e=392(M+H).

EXAMPLE 29

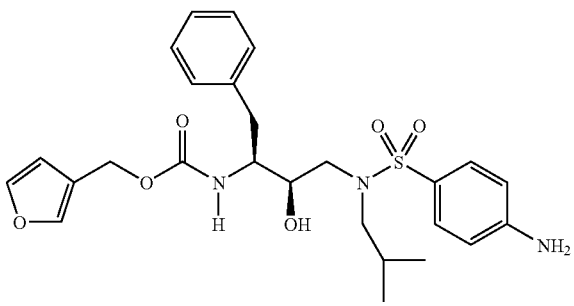

Preparation of Carbamic acid, 2R-hydroxy-3-[[(4-aminophenyl)sulfonyl](2-methylpropyl)amino]-1S-(phenylmethyl)propyl-, 3-furanylmethyl ester To a solution of 104 mg (1.06 mmol) of 3-(hydroxymethyl) furan in 2 mL of anhydrous acetonitrile, was added 0.26 mL (0.25 g, 3.18 mmol) of pyridine and then 277 mg (1.06 mmol) of N,N'-disuccinimidyl carbonate at room temperature under nitrogen. After 45 minutes, 415 mg (1.06 mmol) of 2R-hydroxy-3-[(2-methylpropyl)(4-aminophenyl)sulfonyl]amino-1S-(phenylmethyl)propylamine was added. After stirring at room temperature for 72 hours, ethyl acetate was added, washed with 5% citric acid, saturated sodium bicarbonate and brine, dried over magnesium sulfate, filtered and concentrated to afford 550 mg of crude product. This was chromatographed on silica gel using 50% ethyl acetate/hexane as eluent to afford 230 mg of a white foam, which was identified as the desired 2R-hydroxy-3-[[(4-aminophenyl)sulfonyl](2-methylpropyl)amino]-1S-(phenylmethyl) propylcarbamic acid 3-furanylmethyl ester, m/e=522 (M+Li).

EXAMPLE 30

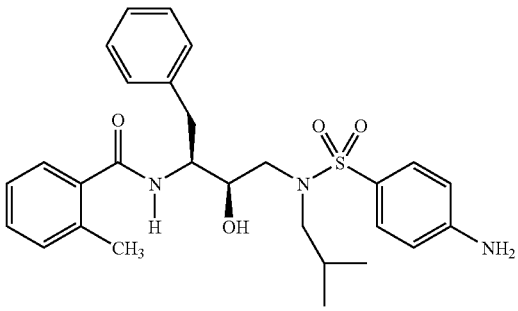

Preparation of Benzamide, N-[2R-hydroxy-3-[[(4-aminophenyl)sulfonyl](2-methylpropyl)amino]-1S-(phenylmethyl)propyl]-2-methyl To a solution of 391 mg (1 mmol) of 2R-hydroxy-3-[(2-methylpropyl)(4-aminophenyl)sulfonyl]amino-1S-(phenylmethyl)propylamine in 3 mL of anhydrous methylene chloride, was added 0.42 mL (3 mmol) of triethylamine, then at room temperature, 0.12 mL (0.9 mmol) of ortho-toluoyl chloride was added. After 15 hours at room temp ethyl acetate was added, washed with 5% citric acid, saturated sodium bicarbonate, brine, dried, filtered and concentrated to afford 420 mg of crude material. This was chromatographed on 40 g of silica gel using 50% ethyl acetate/hexane to afford 368 mg of pure benzamide, N-[(2R-hydroxy-3-[[(4-aminophenyl)sulfonyl](2-methylpropyl)amino]-1S-(phenylmethyl)propyl]-2-methyl, m/e=516 (M+Li).

EXAMPLE 31

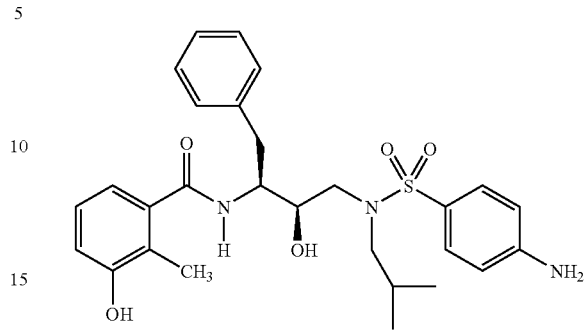

Preparation of Benzamide, N-[2R-hydroxy-3-[[(4-aminophenyl)sulfonyl](2-methylpropyl)amino]-1S-(phenylmethyl)propyl]-3-hydroxy-2-methyl Part A: Preparation of 3-Hydroxy-2-methylbenzoic Acid A one-necked 100 mL round-bottomed flask (magnetic stirring) was charged with 1.0 gram (6.6 mm) 3-amino-2-methylbenzoic acid. A warm mixture of 2.3 mL conc. sulfuric acid in 4.3 mL water was added to the flask, the resulting slurry was cooled below 15° C. in an ice bath, and 6.6 grams of ice was added. The reaction mixture was treated via subsurface addition with a solution of 0.6 gram (8.6 mM) sodium nitrite in 6.6 mL ice water with the reaction temperature maintained at 0-5° C. during the addition. After stirring at 0-5° C. for 30 min., a few crystals of urea were added to decompose the excess nitrite. The reaction mixture was then poured into a room temperature solution of 23.8 grams (102.3 mM) copper (II) nitrate hemipentahydrate in 200 mL water. With vigorous stirring, the reaction mixture was treated with 0.9 gram (6.0 mM) copper (I) oxide. The reaction mixture foamed and changed from turquoise blue to dark green in color. Reaction was left stirring for 30 min. The reaction mixture was extracted with diethyl ether (3×), and the organic extracts were combined. The organic extracts were concentrated to approximately one-fourth the original volume, then extracted with 25 mL 1N sodium hydroxide solution. The layers were separated, and the dark-red aqueous layer was acidified to pH=2 using 1N hydrochloric acid solution. The acidified aqueous layer was then extracted with diethyl ether (3×), and the ether extracts were combined, dried (MgSO4), and concentrated to yield a reddish-colored oil. Purification by flash chromatography on silica gel using a gradient of 0-7% methanol/methylene chloride afforded 0.39 grams (36%) of a yellow solid.

Part B: Preparation of Benzamide, N-[2R-hydroxy-3-[[(4-aminophenyl)sulfonyl](2-methylpropyl)amino]-1S-(phenylmethyl)propyl]-3-hydroxy-2-methyl To a solution of 175 mg (1.15 mmol) of 3-hydroxy-2-methylbenzoic acid and 203 mg (1.5 mmol) of N-hydroxybenzotriazole in 6 mL of anhydrous N,N-dimethylformamide at 0° C., was added 220 mg (1.15 mmol) of EDC. After 20 minutes of activation at 0° C. and 1 hour at room temperature, 392 mg (1.0 mmol) of 2R-hydroxy-3-[(2-methylpropyl)(4-aminophenyl)sulfonyl]amino-1S-(phenylmethyl)propylamine was added. After 15 hours at room temperature, ethyl acetate was added, washed with 5% citric acid, saturated sodium bicarbonate, brine, dried, filtered and concentrated to afford 590 mg of crude material. This was chromatographed on silica gel using 50-80% ethyl acetate/methylene chloride as eluent to afford 255 mg of pure benzamide, N-[2R-hydroxy-3-[[(4-aminophenyl)sulfonyl](2-methylpropyl)amino]-1S-(phenylmethyl)propyl]-3-hydroxy-2-methyl, m/e=526(M+H).

EXAMPLE 32

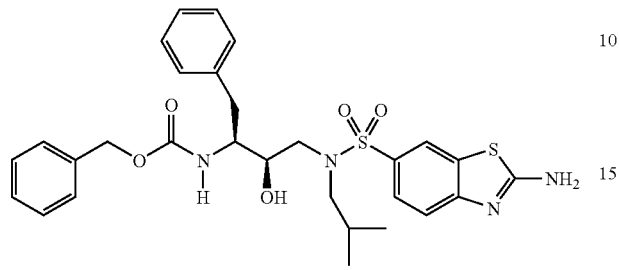

Preparation of Carbamic acid, 2R-hydroxy-3-[[(2-aminobenzothiazol-6-yl)sulfonyl](2-methylpropyl)amino]-1S-(phenylmethyl)propyl-, phenylmethyl ester Carbamic acid, 2R-hydroxy-3-[[(4-aminophenyl)sulfonyl](2-methylpropyl)amino]-1S-(phenylmethyl)propyl-, phenylmethyl ester 0.30 g (0.571 mmol) was added to a well mixed powder of anhydrous copper sulfate (1.20 g) and potassium thiocyanate (1.50 g) followed by dry methanol (6 mL) and the resulting black-brown suspension was heated at reflux for 2 hrs. The reaction mixture was filtered and the filtrate was diluted with water (5 mL) and heated at reflux. Ethanol was added to the reaction mixture, cooled and filtered. The filtrate upon concentration afforded a residue which was chromatographed (ethyl acetate:hexane 80:20) to afford 0.26 g (78%) of the desired compound as a solid.

EXAMPLE 33

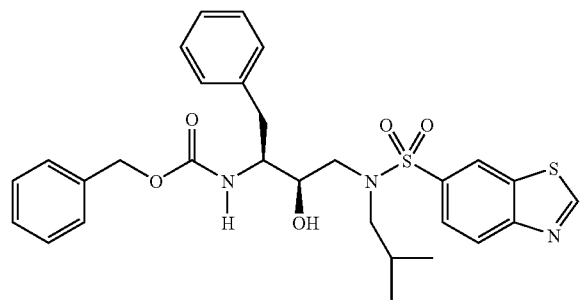

Preparation of Carbamic acid, 2R-hydroxy-3-[[(benzothiazol-6-yl)sulfonyl](2-methylpropyl)amino]-1S-(phenylmethyl)propyl-, phenylmethyl ester Carbamic acid, 2R-hydroxy-3-[[(2-aminobenzothiazol-6-yl)sulfonyl](2-methylpropyl)amino]-1S-(phenylmethyl)propyl-, phenylmethyl ester (0.25 g, 0.429 mmol) was added to a solution of isoamylnitrite (0.116 mL, 0.858 mmol) in dioxane (5 mL) and the mixture was heated at 85° C. After the cessation of evolution of nitrogen, the reaction mixture was concentrated and the residue was purified by chromatography (hexane:ethyl acetate 5:3) to afford 0.130 g (53%) of the desired product as a solid.

EXAMPLE 34

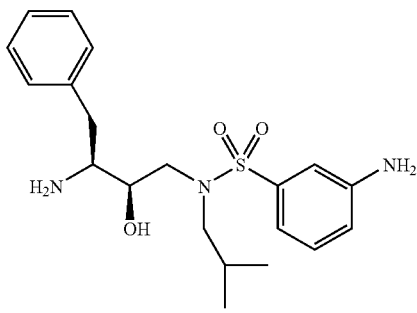

Preparation of 2R-hydroxy-3-[[(3-aminophenyl)sulfonyl](2-methylpropyl)amino]-1S-(phenylmethyl)propylamine Part A: Preparation of Carbamic acid, [2R-hydroxy-3-[(3-nitrophenylsulfonyl)(2-methylpropyl)amino]-1S-(phenylmethyl)propyl-, phenylmethyl ester To a solution of 1.1 g (3.0 mmol) of N-[3S-benzyloxy carbonylamino-2-hydroxy-4-phenyl]-N-isobutylamine in 15 mL of anhydrous methylene chloride, was added 1.3 mL (0.94 g, 9.3 mmol) of triethylamine. The solution was cooled to 0° C. and 0.67 g (3.0 mmol) of 3-nitrobenzene sulfonyl chloride was added, stirred for 30 minutes at 0° C., then for 1 hour at room temperature. Ethyl acetate was added, washed with 5% citric acid, saturated sodium bicarbonate, brine, dried and concentrated to yield 1.74 g of crude material. This was recrystallized from ethyl acetate/hexane to afford 1.40 g of pure carbamic acid, [2R-hydroxy-3-[(3-nitrophenylsulfonyl)(2-methylpropyl)amino]-1S-(phenylmethyl)propyl-, phenylmethyl ester, m/e=562(M+Li).

Part B: Preparation of [2R-hydroxy-3-[[(3-aminophenyl)sulfonyl](2-methylpropyl)amino]-1S-(phenylmethyl)propylamine A solution of 1.33 g (2.5 mmol) of carbamic acid, [2R-hydroxy-3-[(3-nitrophenylsulfonyl)(2-methylpropyl)amino]-1S-(phenylmethyl)propyl-, phenylmethyl ester in 40 mL of 1:1 methanol/tetrahydrofuran was hydrogenated over 0.70 g of 10% palladium-on-carbon catalyst under 40 psig of hydrogen for 1.5 hours. The catalyst was removed by filtration and the solution concentrated to afford 0.87 g of the desired [2R-hydroxy-3-[[(3-aminophenyl)sulfonyl](2-methylpropyl)amino]-1S-(phenylmethyl)propylamine.

EXAMPLE 35

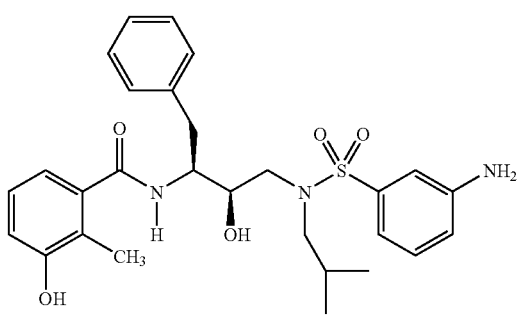

Preparation of Benzamidem, N-[2R-hydroxy-3-[[(3-aminophenyl)sulfonyl](2-methylpropyl)amino]-1S-(phenylmethyl)propyl]-3-hydroxy-2-methyl To a solution of 134 mg (0.88 mmol) of 3-hydroxy-2-methylbenzoic acid and 155 mg (1.15 mmol) of N-hydroxybenzotriazole in 5 mL of anhydrous N,N-dimethylformamide at 0° C., was added 167 mg (0.88 mmol) of EDC. After 20 minutes of activation at 0° C. and 1 hour at room temperature, 300 mg (1.0 mmol) of 2R-hydroxy-3-[(2-methylpropyl)(3-aminophenyl)sulfonyl]amino-1S-(phenylmethyl)propylamine was added. After 15 hours at room temperature, ethyl acetate was added, washed with 5% citric acid, saturated sodium bicarbonate, brine, dried, filtered and concentrated to afford 330 mg of crude material. This was chromatographed on silica gel using 30-70% ethyl acetate/methylene chloride as eluent to afford 230 mg of pure benzamide, N-(2R-hydroxy-3-[[(3-aminophenyl)sulfonyl](2-methylpropyl)amino]-1S-(phenylmethyl)propyl]-3-hydroxy-2-methyl.

EXAMPLE 36

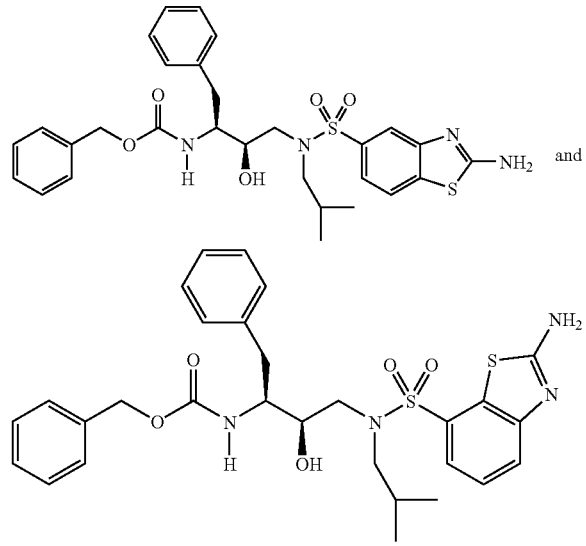

Preparation of Carbamic acid, 2R-hydroxy-3-[[(2-aminobenzothiazol-5-yl)sulfonyl](2-methylpropyl)amino]-1S-(phenylmethyl)propyl-, phenylmethyl ester: and Carbamic acid, 2R-hydroxy-3-[[(2-aminobenzothiazol-7-yl)sulfonyl](2-methylpropyl)amino]-1S-(phenylmethyl)propyl-, phenylmethyl ester The 2R-hydroxy-3-[(3-aminophenylsulfonyl)(2-methylpropyl)amino]-1S-(phenylmethyl)propylcarbamic acid phenylmethyl ester 0.36 g (0.685 mmol) was added to a well mixed powder of anhydrous copper sulfate (1.44 g) and potassium thiocyanate (1.80 g) followed by dry methanol (10 mL) and the resulting black-brown suspension was heated at reflux for 2 hrs. The reaction mixture was filtered and the filtrate was diluted with water (5 mL) and heated at reflux. Ethanol was added to the reaction mixture, cooled and filtered. The filtrate upon concentration afforded a residue which was chromatographed (ethyl acetate:hexane 1:1) to afford 0.18 g (45%) of the 7-isomer as a solid. Further elution of the column with (ethyl acetate:hexane 3:2) afforded 0.80 g (20%) afforded the 5-isomer as a solid.

EXAMPLE 37

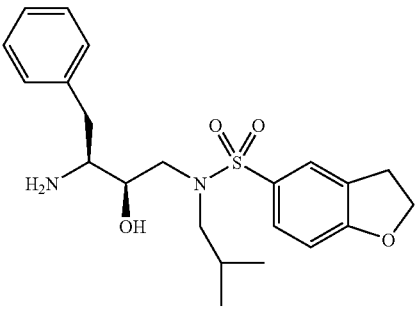

Preparation of 2R-hydroxy-3-[[(2,3-dihydrobenzofuran-5-yl)sulfonyl](2-methylpropyl)amino]-1S-(phenylmethyl)propylamine Part A: Preparation of 5-(2,3-dihydrobenzofuranyl)sulfonyl chloride To a solution of 3.35 g of anhydrous N,N-dimethylformamide at 0° C. under nitrogen was added 6.18 g of sulfuryl chloride, whereupon a solid formed. After stirring for 15 minutes, 4.69 g of 2,3-dihydrobenzofuran was added, and the mixture heated at 100° C. for 2 hours. The reaction was cooled, poured into ice water, extracted with methylene chloride, dried over magnesium sulfate, filtered and concentrated the crude material. This was recrystallized from ethyl acetate to afford 2.45 g of 5-(2,3-dihydrobenzofuranyl) sulfonyl chloride.

Part B: Preparation of Carbamic acid, 2R-hydroxy-3-[[(2,3-dihydrobenzofuran-5-yl)sulfonyl](2-methylpropyl)amino]-1S-(phenylmethyl)propyl-, phenylmethyl ester To a solution of 1.11 g (3.0 mmol) of N-[3S-benzyloxy carbonylamino-2R-hydroxy-4-phenyl]-N-isobutylamine in 20 mL of anhydrous methylene chloride, was added 1.3 mL (0.94 g, 9.3 mmol) of triethylamine. The solution was cooled to 0° C. and 0.66 g of 5-(2,3-dihydrobenzofuranyl) sulfonyl chloride was added, stirred for 15 minutes at 0° C., then for 2 hour at room temperature. Ethyl acetate was added, washed with 5% citric acid, saturated sodium bicarbonate, brine, dried and concentrated to yield 1.62 g of crude material. This was recrystallized from diethyl ether to afford 1.17 g of pure carbamic acid, [2R-hydroxy-3-[[(2,3-dihydrobenzofuran-5-yl)sulfonyl](2-methylpropyl)amino]-1S-(phenylmethyl)propyl-, phenylmethyl ester.

Part C: Preparation of [2R-hydroxy-3-[[(2,3-dihydrobenzofuran-5-yl)sulfonyl](2-methylpropyl)amino]-1S-(phenylmethyl)propylamine A solution of 2.86 g of carbamic acid, [2R-hydroxy-3-[[(2, 3-dihydrobenzofuran-5-yl)sulfonyl](2-methylpropyl)amino]-1S-(phenylmethyl)propyl-, phenylmethyl ester in 30 mL of tetrahydrofuran was hydrogenated 0.99 g of 10% palladium-on-carbon under 50 psig of hydrogen for 16 hours. The catalyst was removed by filtration and the filtrate concentrated to afford 1.99 g of the desired [2R-hydroxy-3-[[(2,3-dihydrobenzofuran-5-yl)sulfonyl](2-methylpropyl)amino]-1S-(phenylmethyl)propylamine.

EXAMPLE 38

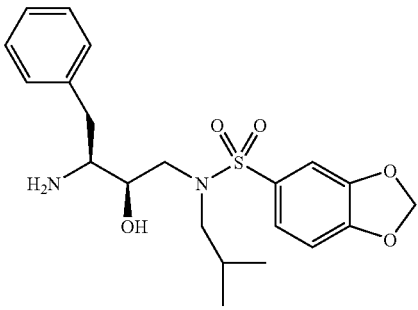

Preparation of 2R-hydroxy-3-[[(1,3-benzodioxol-5-yl)sulfonyl](2-methylpropyl)amino]-1S-(phenylmethyl)propylamine Part A: Preparation of 5-Chlorosulfonyl-1,3-Benzodioxole Method 1:

To a solution of 4.25 g of anhydrous N,N-dimethylformamide at 0° C. under nitrogen was added 7.84 g of sulfuryl chloride, whereupon a solid formed. After stirring for 15 minutes, 6.45 g of 1,3-benzodioxole was added, and the mixture heated at 100° C. for 2 hours. The reaction was cooled, poured into ice water, extracted with methylene chloride, dried over magnesium sulfate, filtered and concentrated to give 7.32 g of crude material as a black oil. This was chromatographed on silica gel using 20% methylene chloride/hexane to afford 1.9 g of (1,3-benzodioxol-5-yl)sulfonyl chloride.

Method 2:

To a 22 liter round bottom flask fitted with a mechanical stirrer, a cooling condenser, a heating mantle and a pressure equalizing dropping funnel was added sulfur trioxide DMF complex (2778 g, 18.1 moles). Dichloroethane (4 liters) was then added and stirring initiated. 1,3-Benzodioxole (1905 g, 15.6 moles) as then added through the dropping funnel over a five minute period. The temperature was then raised to 75° C. and held for 22 hours (NMR indicated that the reaction was done after 9 hours.) The reaction was cooled to 26° and oxalyl chloride (2290 g, 18.1 moles) was added at a rate so as to maintain the temperature below 40° C. (1.5 hours). The mixture was heated to 67° C. for 5 hours followed by cooling to 16° C. with an ice bath. The reaction was quenched with water (5 l) at a rate which kept the temperature below 20° C. After the addition of water was complete, the mixture was stirred for 10 minutes. The layers were separated and the organic layer was washed again twice with water (5 l). The organic layer was dried with magnesium sulfate (500 g) and filtered to remove the drying agent. The solvent was removed under vacuum at 50° C. The resulting warm liquid was allowed to cool at which time a solid began to form. After one hour, the solid was washed with hexane (400 mL), filtered and dried to provide the desired sulfonyl chloride (2823 g). The hexane wash was concentrated and the resulting solid washed with 400 mL hexane to provide additional sulfonyl chloride (464 g). The total yield was 3287 g (95.5% based upon 1,3-benzodioxole).

Method 3:

1,4-benzodioxan-6-sulfonyl chloride was prepared according to the procedure disclosed in EP 583960, incorporated herein by reference.

Part B: Preparation of Carbamic acid, 2R-hydroxy-3-[[(1,3-benzodioxol-5-yl)sulfonyl](2-methylpropyl)amino]-1S-(phenylmethyl)propyl-, phenylmethyl ester To a solution of 3.19 g (8.6 mmol) of N-[3S-benzyloxycarbonylamino-2R-hydroxy-4-phenyl]-N-isobutylamine in 40 mL of anhydrous methylene chloride, was added 0.87 g of triethylamine. The solution was cooled to 0° C. and 1.90 g of (1,3-benzodioxol-5-yl)sulfonyl chloride was added, stirred for 15 minutes at 0° C., then for 17 hours at room temperature. Ethyl acetate was added, washed with 5% citric acid, saturated sodium bicarbonate, brine, dried and concentrated to yield crude material. This was recrystallized from diethyl ether/hexane to afford 4.77 g of pure carbamic acid, 2R-hydroxy-3-[[(1,3-benzodioxol-5-yl)sulfonyl](2-methylpropyl)amino]-1S-(phenylmethyl)propyl-, phenylmethyl ester.

Part C: Preparation of 2R-hydroxy-3-[[(1,3-benzodioxol-5-yl)sulfonyl](2-methylpropyl)amino]-1S-(phenylmethyl)propylamine A solution of 4.11 g of carbamic acid, 2R-hydroxy-3-[[(1,3-benzodioxol-5-yl)sulfonyl](2-methylpropyl)amino]-1S-(phenylmethyl)propyl-, phenylmethyl ester in 45 mL of tetrahydrofuran and 25 mL of methanol was hydrogenated over 1.1 g of 10% palladium-on-carbon under 50 psig of hydrogen for 16 hours. The catalyst was removed by filtration and the filtrate concentrated to afford 1.82 g of the desired 2R-hydroxy-3-[[(1,3-benzodioxol-5-yl)sulfonyl](2-methylpropyl)amino]-1S-(phenylmethyl)propylamine.

EXAMPLE 39

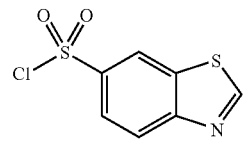

Preparation of Benzothiazole-6-sulfonyl Chloride

Part A: Preparation of N-(4-Sulfonamidophenyl)thiourea

A mixture of sulfanilamide (86 g, 0.5 mole), ammonium thiocyanate (76.0 g, 0.5 mole) and dilute hydrochloric acid (1.5 N, 1 L) was mechanically stirred and heated at reflux for 2 hr. About 200 mL of water was distilled off and concentration of the reaction mixture afforded a solid. The solid was filtered and was washed with cold water and air dried to afford 67.5 g (59%) of the desired product as a white powder.

Part B: Preparation of 2-Amino-6-sulfonamidobenzothiazole

Bromine (43.20 g, 0.27 mol) in chloroform (200 mL) was added over 1 hr. to a suspension of N-(4-sulfonamidophenyl)-thiourea (27.72, 0.120 mol) in chloroform (800 mL). After the addition, the reaction mixture was heated at reflux for 4.5 hr. The chloroform was removed in vacuo and the residue was repeatedly distilled with additional amounts of chloroform. The solid obtained was treated with water (600 mL) followed by ammonium hydroxide (to make it basic), then was heated at reflux for 1 hr. The cooled reaction mixture was filtered, washed with water and air dried to afford 22.0 g (80%) of the desired product as a white powder.

Part C: Preparation of Benzothiazole-6-sulfonic acid

A suspension of 2-amino-6-sulfonamido-benzothiazole (10.0 g, 43.67 mmol) in dioxane (300 mL) was heated at reflux. Isoamylnitrite (24 mL) was added in two portions to the reaction mixture. Vigorous evolution of gas was observed (the reaction was conducted behind a shield as a precaution) and after 2 hr., a red precipitate was deposited in the reaction vessel. The reaction mixture was filtered hot, and the solid was washed with dioxane and was dried. The solid was recrystallized from methanol-water. A small amount of a precipitate was formed after 2 days. The precipitate was filtered off and the mother liquor was concentrated in vacuo to afford a pale red-orange solid (8.0 g, 85%) of pure product.

Part D: Preparation of 6-Chlorosulfonylbenzothiazole

Thionyl chloride (4 mL) was added to a suspension of the benzothiazole-6-sulfonic acid (0.60 g, 2.79 mmol) in dichloroethane (15 mL) and the reaction mixture was heated at reflux and dimethylformamide (5 mL) was added to the reaction mixture to yield a clear solution. After 1.5 hr. at reflux, the solvent was removed in vacuo and excess HCl and thionyl chloride was chased by evaporation with dichloroethane.

EXAMPLE 40

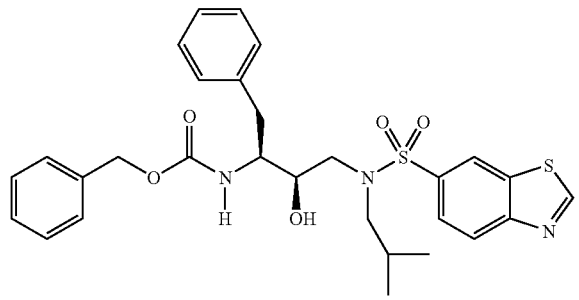

Preparation of Carbamic acid, 2R-hydroxy-3-[[(benzothiazol-6-yl)sulfonyl](2-methylpropyl)amino]-1S-(phenylmethyl)propyl-, phenylmethyl ester Crude benzothiazole-6-sulfonyl chloride in ethyl acetate (100 mL) was added to N-[3S-benzyloxycarbonylamino-2R-hydroxy-4-phenyl]-N-isobutylamine (1.03 g, 2.78 mmol) followed by N-methylmorpholine (4 mL). After stirring at room temperature for 18 hr., the reaction mixture was diluted with ethyl acetate (100 mL), washed with citric acid (5%, 100 mL), sodium bicarbonate (saturated, 100 mL) and brine (100 mL), dried (MgSO4) and concentrated in vacuo. The residue was chromatographed (silica gel, ethyl acetate: hexane 1:1) to afford 0.340 g (23%) of desired product.

EXAMPLE 41

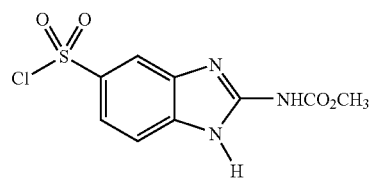

Preparation of 5-Chlorosulfonyl-2-carbomethoxyamino-benzimidazole

A solution of 2-carbomethoxyamino-benzimidazole (5.0 g, 0.026 mole) in chlorosulfonic acid (35.00 mL) was stirred at 0° C. for 30 min. and at room temperature for 3 hr. The resulting dark colored reaction mixture was carefully poured into an ice-water mixture (200 mL) and stirred at room temperature for 30 min. The resulting precipitate was filtered and washed throughly with cold water (500 ml). The solid was dried overnight under high vacuum in a desiccator over NaOH pallets to yield the desired compound (5.9 g. 78%) as a grey powder. $^1$H NMR (DMSO-d6) 3.89 (s, 3H), 7.55 (d, 1H, J=8.4 Hz.) 7.65 (d, 1H, J=8.4 Hz), 7.88 (s, 1H).

EXAMPLE 42

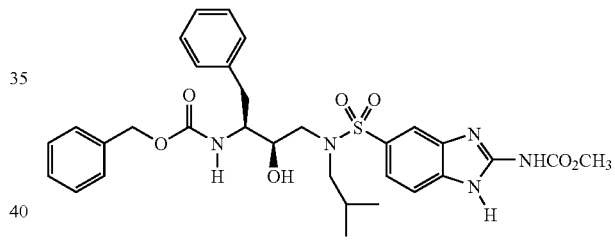

Preparation of Carbamic acid, 2R-hydroxy-3-[[(2-carbomethoxyamino-benzimidazol-5-yl)sulfonyl](2-methylpropyl)amino]-1S-(phenylmethyl)propyl-, phenylmethyl ester To a cold solution of N-[3S-benzyloxycarbonylamino-2R-hydroxy-4-phenylbutyl]-N-isobutylamine (5.0 g, 13.5 mmole) in dichloromethane (70 mL) was added triethylamine (5.95 g, 54.0 mmole) followed by 5-chlorosulfonyl-2-carbomethoxyaminobenzimidazole (4.29 g, 14.85 mmole) in small portions. The reaction mixture was stirred at 0° C. for 30 min. and at room temperature for 2.5 hr. When TLC (EtOAc) indicated complete reaction of the amino alcohol, the mixture was cooled and filtered. The filtrate was concentrated. The residue was dissolved in EtOAc (200 mL), washed successively with cold 5% citric acid (3×50 mL), saturated sodium bicarbonate (3×50 mL), water (3×100 mL) and dried (Na2SO4). The EtOAc was removed in vacuo and the residue was dried under vacuum. The residue thus obtained was triturated with methanol, cooled, filtered, washed with MeOH-EtOAc (1:1, v/v) and dried in a desiccator to give the desired sulfonamide (6.02 g, 72%) as a light brown powder. FABMS: m/z 630 (M+Li); HRMS: calcd. for $C_{31}H_{38}N_5O_7S$ (M+H) 624.2492, found 624.2488.

EXAMPLE 43

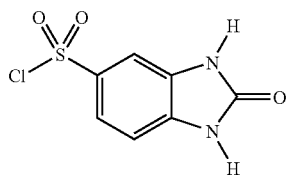

Preparation of 5-Chlorosulfonylbenzimidazolone

Sulfur trioxide/N,N-dimethylformamide complex (13.7 g, 89.5 mmoles) and 1,2-dichloroethane (40 mL) were added to a 250 mL, 3-necked flask under nitrogen. The slurry was stirred at room temperature and 2-hydroxybenzimidazole (10 g, 74.6 mmloes) was added as a solid in portions at room temperature. The slurry was slowly heated to 85° C. and was then maintained at 85° C. for 16 hours. A thick gummy paste formed at the bottom of the flask during the heating period. The reaction mixture was cooled to room temperature, and thionyl chloride (10.65 g, 89.5 mmoles) was added dropwise. The reaction mixture was slowly heated to 85° C. and maintained at 85° C. for 5 hours. As a result, the gummy paste slowly turned into a fine powder. The heterogeneous reaction mixture was then cooled to room temperature and diluted with 200 mL of dichloromethane. Water (100 mL) was added to the organic solution and a solid formed in the aqueous layer which was collected by filtration and washed with excess water and acetonitrile to give 3.9 g of a solid. The solid contained both the desired sulfonyl chloride product along with some of the corresponding sulfonic acid. The crude material was used without further purification.

EXAMPLE 44

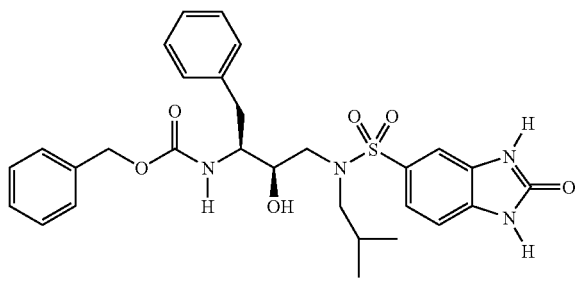

Preparation of Carbamic acid, 2R-hydroxy-3-[[(benzimidazolon-5-yl)sulfonyl](2-methylpropyl)amino]-1S-(phenylmethyl)propyl-, phenylmethyl ester To N-[3S-benzyloxycarbonylamino-2R-hydroxy-4-phenylbutyl]-N-isobutylamine (1 g, 2.7 mmoles) was dissolved in 10 mL dichloromethane and then cooled to 5° C. Triethylamine (1.04 g, 10.8 mmoles) was added to the mixture. Crude 5-chlorosulfonyl-benzimidazolone (0.6 g, 2.7 mmoles) from Example 43 was added as a solid in portions to the cooled mixture. The resulting heterogeneous reaction mixture was stirred at 5° C. for 1 hour, then warmed to room temperature and stirred at room temperature for 16 hours. Dichloromethane was removed and the residue was dissolved in 100 mL of ethylacetate. The organic solution was washed with 5% citric acid (2×50 mL), 5% sodium bicarbonate (2×50 mL) and brine (2×50 mL) and dried over magnesium sulfate. The magnesium sulfate was filtered off and washed with dichloromethane. The solvents were removed in vacuo and the concentrated residue was purified by flash column chromatography on silica gel eluting with 3% methanol in dichloromethane to yield 0.49 g (33.5% yield) of white solid of pure product.

EXAMPLE 45

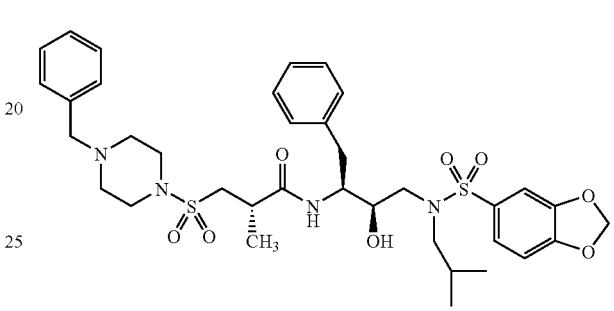

Preparation of $N^1$-[1-[N-(2-methylpropyl)-N-(3,4-methylenedioxyphenylsulfonyl)amino]-2(R)-hydroxy-3(S)-(phenylmethyl)prop-3-yl]-3-[(4-benzylpiperizin-1-yl)sulfonyl]-2(R)-methylpropionamide

Part A: Preparation of benzyl 3-(4-benzylpiperizin-1-yl sulfonyl)-2(R)-methylpropionate A 100 mL round bottom flask equipped with magnetic stirring bar and $N_2$ inlet was charged with 2.5 g benzyl 3-chlorosulfonyl-2(R)-methylpropionate in 25 mL $CH_2Cl_2$. The solution was cooled to 0° C. and charged with 1.57 mL (1.0 eq.) 4-benzylpiperazine and 1.26 mL $NEt_3$. The reaction was stirred for 1 hour then concentrated in vacuo and partitioned between ethyl acetate and saturated sodium bicarbonate. The combined organics were washed with brine, dried over $Na_2SO_4$, and concentrated in vacuo to yield 3.4 g crude product. Flash chromatography (80:20 ethyl acetate/hexane) yielded 3.0 g pure product.

Part B: Preparation of benzyl 3-(4-benzylpiperizin-1-yl sulfonyl)-2(R)-methylpropionic acid A 100 mL round bottom flask equipped with magnetic stirring bar and $N_2$ inlet was charged with 3.0 g benzyl 3-(4-benzylpiperizin-1-ylsulfonyl)-2(R)-methylpropionate, 1.2 g LiOH (4 eq.) in 20 mL 50% aqueous methanol. After 2 hours HPLC analysis showed no starting material. The reaction was concentrated to half volume and partitioned between $Et_2O$ and $H_2O$. The aqueous layer was acidified to pH 5 and extracted with 2×75 mL ethyl acetate. The combined organics were dried, and concentrated in vacuo to yield 550 mg (25%) white solid.

Part C: Preparation of N¹-[1-[N-(2-methylpropyl)-N-(3,4-methylenedioxyphenylsulfonyl)amino]-2(R)-hydroxy-3(S)-(phenylmethyl)prop-3-yl]-3-[(4-benzylpiperizin-1-yl)sulfonyl]-2(R)-methylproprionamide-HCl A 100 mL round bottom flask equipped with magnetic stirring bar and $N_2$ inlet was charged with 375 mg (1.15 eq.) 3-(4-benzylpiperizin-1-ylsulfonyl)-2(R)-methylpropionic acid in 3 mL DMF. The solution was cooled to 0° C. and charged with 200 mg (1.5 eq.) of HoBt followed by 220 mg (1.15 eq.) EDC. After 20 minutes at 0° C. a solution of 512 mg 2R-hydroxy-3-[[(1,3-benzodioxol-5-yl)sulfonyl](2-methylpropyl)amino]-1S-(phenylmethyl)propylamine in 5 mL DMF was added and the reaction was stirred at room temperature for 20 hours. The reaction was concentrated in vacuo and partionned between ethyl acetate and aqueous saturated sodium bicarbonate. The combined organics were dried and concentrated to crude product. Flash Chromatography (100% ethyl acetate) yielded 360 mg pure product. m/e=735(M+Li). The free amine was taken up in 10 mL acetonitrile and treated with 2 eq. concentrated HCl. After 10 minutes the solution was concentrated in vacuo and triturated with diethyl ether to yield 325 mg pure N¹-[1-[N-(2-methylpropyl)-N-(3,4-methylenedioxyphenylsulfonyl)amino]-2(R)-hydroxy-3(S)-(phenylmethyl)prop-3-yl]-3-[(4-benzylpiperizin-1-yl)sulfonyl]-2(R)-methylproprionamide-HCl.

EXAMPLE 46

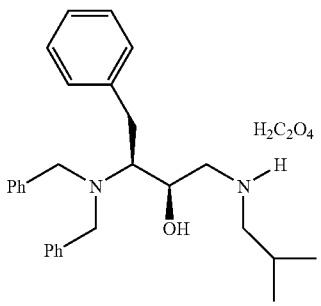

Preparation of N-[3(S)-[N,N-bis(phenylmethyl)amino]-2(R)-hydroxy-4-phenylbutyl]-N-isobutylamine.oxalic acid salt Part A: Preparation of N-[3(S)-(N,N-bis(phenylmethyl)amino]-2(R)-hydroxy-4-phenylbutyl]-N-isobutylamine To a solution of crude N,N-dibenzyl-3(S)-amino-1,2(S)-epoxy-4-phenylbutane (388.5 g, 1.13 mol) in isopropanol (2.7 L) (or ethyl acetate) was added isobutylamine (1.7 kgm, 23.1 mol) over 2 min. The temperature increased from 25° C. and to 30° C. The solution was heated to 82° C. and stirred at this temperature for 1.5 h. The warm solution was concentrated under reduced pressure at 65° C., The brown oil resdiue was transferred to a 3-L flask and dried in vacuo (0.8 mm Hg) for 16 h to give 450 g of 3S-[N,N-bis(phenylmethyl)amino-4-phenylbutan-2R-ol as a crude oil. The product was used directly in the next step without purification. An analytical sample of the desired major diastereomeric product was obtained by purifying a small sample of crude product by silica gel chromatography (40% ethyl acetate/hexane). Tlc analysis: silica gel, 40% ethyl acetate/hexane; Rf=0.28; HPLC analysis: ultrasphere ODS column, 25% triethylamino-/phosphate buffer pH 3-acetonitrile, flow rate 1 mL/min, UV detector; retention time 7.49 min.; HRMS calcd for $C_{28}H_{27}N_2O$ (M+1) 417.616, found 417.2887.

An analytical sample of the minor diastereomeric product, 3S-[N,N-bis(phenylmethyl)amino]1-(2-methylpropyl) amino-4-phenylbutan-2S-ol was also obtained by purifying a small sample of crude product by silica gel chromatography (40% ethyl acetate/hexane).

Part B: Preparation of N-[3(S)-[N,N-bis(phenylmethyl)amino]-2(R)-hydroxy-4-phenylbutyl]-N-isobutylamine.oxalic acid salt Oxalic acid dihydrate (119 g, 0.94 mole) was added to a 5000 mL round bottom flask fitted with a mechanical stirrer and a dropping funnel. Methanol (1000 ml) was added and the mixture stirred until dissolution was complete. A solution of crude 3(S)-[N,N-bis(phenylmethyl)amino]-1-(2-methylpropyl)amino-4-phenylbutano-2(R)-ol in ethyl acetate (1800 ml, 0.212 g amino alcohol isomers/mL , 0.9428 moles) was added over a twenty minute period. The mixture was stirred for 18 hours and the solid product was isolated by centrifugation in six portions at 400 G. Each portion was washed with 125 mL of ethyl acetate. The salt was then collected and dried overnight at 1 torr to yield 336.3 g of product (71% based upon total amino alcohol). HPLC/MS (electrospray) was consistent with the desired product (m/z 417 [M+H]⁺).

EXAMPLE 47

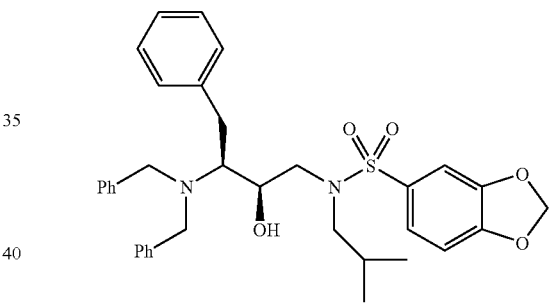

Preparation of 1-[N-[(1,3-benzodioxol-5-yl)sulfonyl]-N-(2-methylpropyl)amino]-3(S)-[bis(phenylmethyl)amino]-4-phenyl-2(R)-butanol To a 5000 mL, 3-necked flask fitted with a mechanical stirrer was added N-[3(S)-[N,N-bis(phenylmethyl)amino]-2(R)-hydroxy-4-phenylbutyl]-N-isobutylamine.oxalic acid salt (354.7 g, 0.7 mole) and 1,4-dioxane (2000 mL). A solution of potassium carbonate (241.9 g, 1.75 moles) in water (250 mL) was then added. The resultant heterogeneous mixture was stirred for 2 hours at room temperature followed by the addition of 1,3-benzodioxole-5-sulfonyl chloride (162.2 g, 0.735 mole) dissolved in 1,4-dioxane (250 mL) over 15 minutes. The reaction mixture was stirred at room temperature for 18 hours. Ethyl acetate (1000 mL) and water (500 mL) were charged to the reactor and stirring continued for another 1 hour. The aqueous layer was separated and further extracted with ethyl acetate (200 mL). The combined ethyl acetate layers were washed with 25% brine solution (500 mL) and dried over anhydrous magnesium sulfate. After filtering and washing the magnesium sulfate with ethyl acetate (200 mL), the solvent in the filtrate was removed under reduced pressure yielding the desired sulfonamide as an viscous yellow foamy oil (440.2 g 105% yield). HPLC/MS (electrospray) (m/z 601 [M+H]⁺].

EXAMPLE 48

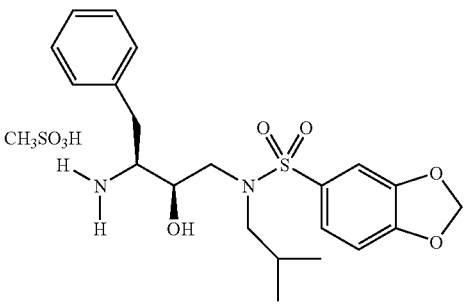

Preparation of 1-[N-[(1,3-benzodioxol-5-yl)sulfonyl]-N-(2-methylpropyl)amino]-3(S)-amino-4-phenyl-2(R)-butanol.methanesulfonic acid salt Crude 1-[N-[(1,3-benzodioxol-5-yl)sulfonyl]-N-(2-methylpropyl)amino]-3(S)-[bis(phenylmethyl)amino]-4-phenyl-2(R)-butanol (6.2 g, 0.010 moles) was dissolved in methanol (40 mL). Methanesulfonic acid (0.969 g, 0.010 moles) and water (5 mL) were then added to the solution. The mixture was placed in a 500 mL Parr hydrogenation bottle containing 20% Pd(OH)$_2$ on carbon (255 mg, 50% water content). The bottle was placed in the hydrogenator and purged 5 times with nitrogen and 5 times with hydrogen. The reaction was allowed to proceed at 35° C. with 63 PSI hydrogen pressure for 18 hours. Additional catalyst (125 mg) was added and, after purging, the hydrogenation continued for and additional 20 hours. The mixture was filtered through celite which was washed with methanol (2×10 mL). Approximately one third of the methanol was removed under reduced pressure. The remaining methanol was removed by aziotropic distillation with toluene at 80 torr. Toluene was added in 15, 10, 10 and 10 mL portions. The product crystallized from the mixture and was filtered and washed twice with 10 mL portions of toluene. The solid was dried at room temperature at 1 torr for 6 hours to yield the amine salt (4.5 g, 84%). HPLC/MS (electrospray) was consistent with the desired product (m/z 421 [M+H]$^+$).

EXAMPLE 49

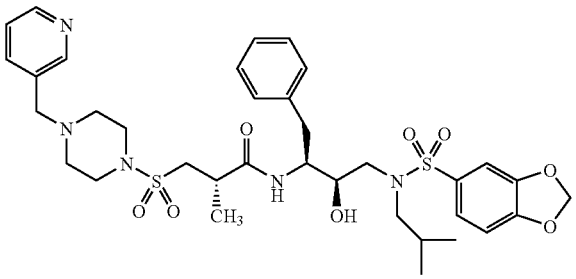

Preparation of N$^1$-[1-[N-(2-methylpropyl)-N-(3,4-methylenedioxyphenylsulfonyl)amino]-2(R)-hydroxy-3(S)-(phenylmethyl)prop-3-yl]-3-[(4-(3-pyridylmethyl)piperizin-1-yl)sulfonyl]-2(R)-methylproprionamide.

Part A: Preparation of benzyl 3-(4-tert-butoxycarbonylpiperizin-1-ylsulfonyl)-2(R)-methylpropionate A 100 mL round bottom flask equipped with magnetic stirring bar and N$_2$ inlet was charged with 5.2 g benzyl 3-chlorosulfonyl-2(R)-methylpropionate in 50 mL CH$_2$Cl$_2$. The flask was cooled to 0° C. and charged with 3.5 g N-Boc-piperazine and 2.9 mL (1.1 eq.) NEt$_3$. The reaction was stirred 30 minutes at 0° C., concentrated in vacuo and partitionned between ethyl acetate/water. The combined organics were washed with 5% aqueous. citric acid, saturated aqueous sodium bicarbonate, brine, and concentrated in vacuo to yield a yellow liquid. Purification via flash chromatography on silica gel (30% ethyl acetate/hexane) yielded 7.2 g (90%) product as a clear oil.

Part B: Preparation of 3-(4-tert-butoxycarbonyl piperizin-1-ylsulfonyl)-2(R)-methylpropionic acid A 300 mL Fisher Porter vessel equipped with magnetic stirring bar was charged with 7.2 g benzyl 3-(4-tert-butoxycarbonylpiperizin-1-ylsulfonyl)-2(R)-methylpropionate, 600 mg 10% Pd—C, and 100 mL MeOH. The reaction vessel was charged with 50 psi H$_2$ and stirred for 2 hours at room temperature. The reaction mixture was filtered thru Celite and concentrated in vacuo to yield 5.25 g (93%) white solid. The free acid was used without further purification.

Part C: Preparation of N$^1$-[1-[N-(2-methylpropyl)-N-(3,4-methylenedioxyphenylsulfonyl)amino]-2(R)-hydroxy-2(S)-(phenylmethyl)prop-3-yl]-3-[4-tert-butoxycarbonylpiperizin-1-yl)sulfonyl]-2(R)-methyl proprionamide A 250 mL round bottom flask equipped with magnetic stirring bar and N$_2$ inlet was charged with 4.9 g (1.0 eq.) 3-(4-tert-butoxycarbonylpiperizin-1-ylsulfonyl)-2(R)-methylpropionic acid in 100 mL DMF. The solution was cooled to 0° C. and charged with 2.4 g (1.2 eq.) of HoBt followed by 2.8 g (1.0 eq.) EDC. After 20 minutes at 0° C. a solution of 6.9 g (1.1 eq.) 2R-hydroxy-3-[[(1,3-benzodioxol-5-yl)sulfonyl](2-methylpropyl)amino]-1S-(phenylmethyl)propylamine in 50 mL DMF was added and the reaction was stirred at room temperature for 20 hrs. The reaction was concentrated in vacuo and partitioned between ethyl acetate and aqueous saturated bicarbonate. The combined organics were washed with 5% aqueous citric acid, brine, dried over Na$_2$SO$_4$ and concentrated to 12.8 g crude product. Flash Chromatography on silica gel (50-100% ethyl acetate/hexane) yielded 10.6 g (98%) pure product.

Part D: Preparation of N$^1$-[1-(N-(2-methylpropyl)-N-(3,4-methylenedioxyphenylsulfonyl)amino]-2(R)-hydroxy-2(S)-(phenylmethyl)prop-3-yl]-3-[1-piperizin-1-ylsulfonyl]-2(R)-methylpropionamide A 100 mL round bottom flask equipped with magnetic stirring bar and N$_2$ inlet was charged with 1.0 g N$^1$-[1-[N-(2-methylpropyl)-N-(3,4-methylenedioxyphenylsulfonyl)amino]-2(R)-hydroxy-3(S)-(phenylmethyl)prop-3-yl]-3-[(4-tert-butoxycarbonylpiperizin-1-yl)sulfonyl]-2(R)-methylproprionamide in 10 mL 4N HCl-Dioxane. After stirring 1 hour the reaction mixture was concentrated in vacuo and partitioned between ethyl acetate and 10% aqueous potassium carbonate. The combined organics were dried and concentrated to a crude white foam that was triturated from diethyl ether and used without further purification.

Part E: Preparation of N$^1$-[1-[N-(2-methylpropyl)-N-(3,4-methylenedioxyphenylsulfonyl)amino]-2(R-hydroxy-3(S)-(phenylmethyl)prop-3-yl]-3-[(4-(3-pyridylmethyl)piperizin-1-yl)sulfonyl]-2(R)-methylproprionamide A 100 mL round bottom flask equipped with magnetic stirring bar and N$_2$ inlet was charged with 450 mg crude amine from Part D, 100 mg potassium carbonate (~3 eq.) and 115 mg 3-Picoyl Chloride HCl (~1 eq.) in 10 mL DMF.

The reaction was stirred overnight at room temperature then partionned between ethyl acetate and saturated aqueous sodium bicarbonate. The combined organics were dried and concentrated to 480 mg crude material. Flash Chromatography with 3% MeOH/EA then 100% THF yielded 200 mg pure N$^1$-[1-[N-(2-methylpropyl)-N-(3,4-methylenedioxyphenylsulfonyl)amino]-2(R-hydroxy-3(S)-(phenylmethyl)prop-3-yl]-3-[(4-(3-pyridylmethyl)piperizin-1-yl)sulfonyl]-2(R)-methylproprionamide, m/e=729(M+H).

EXAMPLE 50

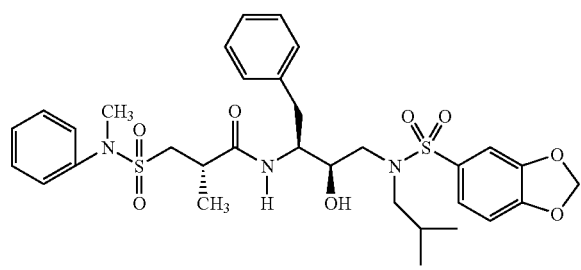

Preparation of N-[2R-hydroxy-3-[N$^1$-(2-methylpropyl)-N$^1$-[(1,3-benzodioxol-5-yl)sulfonyl]amino]-1S-(phenylmethyl)propyl]-2S-methyl-3-[(N$^2$-methyl-N$^2$-phenylamino)sulfonyl]propanamide Part A: Preparation of Benzyl 3-(S-acetyl)-2S-methylpropionate Benzyl bromide (16.5 g, 96.5 mmol) was added to a solution of 3-(S-acetyl)-2S-methylpropionic acid (13.6 g, 100 mmol) and DBU (15.2 g, 100 mmol) in toluene (200 mL). The reaction mixture was stirred at room temperature for 18 hours, diluted with toluene (200 mL), washed sequentially with 1N HCl (200 mL), sodium bicarbonate (200 mL) and brine (200 mL), dried, filtered and concentrated to afford 21 g of benzyl 3-(S-acetyl)-2S-methylpropionate.

Part B: Preparation of Benzyl 3-(chlorosulfonyl)-2S-methylpropionate

Chlorine gas was bubbled into a cold (ice-water) solution of benzyl 3-(S-acetyl)-2S-methylpropionate (10.0 g) in ethanol-chloroform (10:90, 100 mL) until a deep yellow color persisted. The reaction mixture was stirred for 30 minutes, then warmed to room temperature, concentrated and dried in vacuo to afford 10 g (90%) of benzyl 3-(chlorosulfonyl)-2S-methylpropionate as a colorless oil.

Part C: Preparation of Benzyl 3-[(N-methyl-N-phenylamino)sulfonyl]-2S-methylpropionate Triethylamine (1.7 mL) was added to a cooled (ice-water) solution of N-methylaniline (1.29 g, 11.98 mmol) and benzyl 3-(chlorosulfonyl)-2S-methyl-propionate (3.0 g, 10.85 mmol) in dichloromethane (30 mL). The reaction mixture was stirred for 18 hours, diluted with dichloromethane (100 mL), washed sequentially with HCl (1N, 100 mL), sodium bicarbonate (100 mL) and brine (100 mL), dried (MgSO$_4$), filtered and concentrated to afford 3.5 g (93%) of benzyl 3-[(N-methyl-N-phenylamino)sulfonyl]-2S-methylpropionate.

Part D: Preparation of 3-[(N-Methyl-N-phenylamino)sulfonyl]-2S-methylpropionic acid A mixture of benzyl (3-(N-methyl-N-phenylamino)sulfonyl]-2S-methylpropionate (3.50 g, 10.90 mmol) and palladium/carbon catalyst (300 mg) in methanol (20 mL) was subjected to hydrogenolysis for 16 hours at room temperature. The catalyst was filtered off, and the filtrate was concentrated to afford 2.5 g of 3-[(N-methyl-N-phenylamino)sulfonyl]-2S-methylpropionic acid.

Part E: Preparation of N-[2R-hydroxy-3-[N$^1$-(2-methyl propyl)-N$^1$-[(1,3-benzodioxol-5-yl)sulfonyl]amino]-1S-(phenylmethyl)propyl]-2S-methyl-3-[(N$^2$-methyl-N$^2$-phenylamino)sulfonyl]propanamide A mixture of 3-[(N-methyl-N-phenylamino)sulfonyl]-2S-methylpropionic acid (0.701 g, 2.7276 mmol), HOBT (0.41 g, 3.037 mmol) and EDC (0.58 g, 3.037 mmol) in DMF was stirred at room temperature for 1 hour, then N-[2R-hydroxy-3-[N$^1$-(2-methylpropyl)-N$^1$-[(1,3-benzodioxol-5-yl)sulfonyl]amino]-1S-(phenylmethyl)propylamine (1.50 g, 3.5714 mmol) was added to the reaction mixture and it was stirred at room temperature for 18 hours. The reaction mixture was concentrated. The resulting residue was dissolved in dichloromethane (200 mL), washed with citric acid (1N, 100 mL), sodium bicarbonate (100 mL), brine (100 mL), dried (MgSO$_4$), filtered and concentrated. The residue obtained was purified by flash column chromatography on silica gel eluting with ethyl acetate:hexane (3:1) to afford 0.90 g (50%) of pure N-(2R-hydroxy-3-[N$^1$-(2-methylpropyl)-N$^1$-[(1,3-benzodioxol-5-yl)sulfonyl]amino]-1S-(phenylmethyl)propyl]-2S-methyl-3-[(N$^2$-methyl-N$^2$-phenylamino)sulfonyl]propanamide; FAB-MS for $C_{32}H_{41}N_3O_8S_2$: found: m/z=659.

EXAMPLE 51

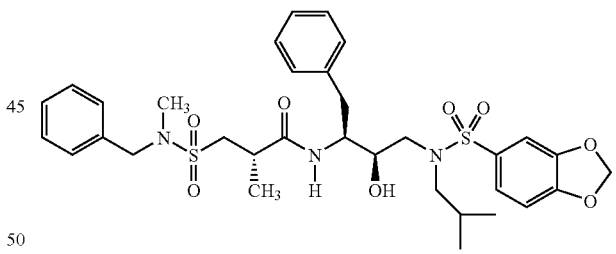

Preparation of N-[2R-hydroxy-3-[N$^1$-(2-methylpropyl)-N$^1$-[(1,3-benzodioxol-5-yl)sulfonyl]amino]-1S-(phenylmethyl)propyl]-2S-methyl-3-[(N$^2$-methyl-N$^2$-benzylamino)sulfonyl]propanamide.

Part A: Preparation of Benzyl 3-[(N-Methyl-N-benzylamino)sulfonyl]-2S-methylpropionate Triethylamine (1.7 mL) was added to a cooled (ice-water) solution of N-methyl-benzylamine (1.45 g, 11.98 mmol) and benzyl 3-(chlorosulfonyl)-2S-methyl-propionate (3.0 g, 10.85 mmol) in dichloromethane (30 mL). The reaction mixture was stirred for 18 hours, diluted with dichloromethane (100 mL), washed with HCl (1N, 100 mL), sodium bicarbonate (100 mL), brine (100 mL), dried (MgSO$_4$), filtered and concentrated to afford 3.80 g (97%) of benzyl 3-[(N-methyl-N-benzylamino)sulfonyl]-2S-methylpropionate.

Part B: Preparation of 3-[(N-Methyl-N-benzylamino)sulfonyl]-2S-methylpropionic acid A mixture of benzyl [3-(N-methyl-N-benzylamino)sulfonyl]-2S-methylpropionate (3.80 g, 10.90 mmol) and palladium/carbon (300 mg) catalyst in methanol (20 mL) was subjected to hydrogenolysis for 16 hours. The catalyst was filtered off, and the filtrate was concentrated to afford 3.2 g (quantitative) of 3-[(N-methyl-N-benzylamino)sulfonyl]-2S-methylpropionic acid.

Part C: Preparation of N-[2R-hydroxy-3-[N$^1$-(2-methylpropyl)-N$^1$-[(1,3-benzodioxol-5-yl)sulfonyl]amino]-1S-(phenylmethyl)propyl]-2S-methyl-3-[(N$^2$-methyl-N$^2$-benzylamino) sulfonyl]propanamide A mixture of 3-[(N-methyl-N-benzylamino)sulfonyl]-2S-methylpropionic acid (0.744 g, 2.7454 mmol), HOBT (0.41 g, 3.037 mmol) and EDC (0.58 g, 3.037 mmol) in DMF was stirred at room temperature for 1 hour, then N-[2R-hydroxy-3-[N$^1$-(2-methylpropyl)-N$^1$-[(1,3-benzodioxol-5-yl)sulfonyl]amino]-1S-(phenylmethyl)propylamine (1.50 g, 3.5714 mmol) was added to the reaction mixture, and it was stirred for 18 hours at room temperature. The reaction mixture was concentrated. The resulting residue was dissolved in dichloromethane (200 mL), washed with citric acid (1N, 100 mL), sodium bicarbonate (100 mL) and brine (100 mL), dried (MgSO$_4$), filtered and concentrated. The residue obtained was purified by flash column chromatography on silica gel eluting with ethyl acetate:hexane (3:1) to afford 1.1 g (59%) of pure N-[2R-hydroxy-3-[N$^1$-(2-methylpropyl)-N$^1$-[(1,3-benzodioxol-5-yl)sulfonyl]amino]-1S-(phenylmethyl)propyl]-2S-methyl-3-[(N$^2$-methyl-N$^2$-benzylamino)sulfonyl]propanamide; FAB-MS for $C_{33}H_{43}N_3O_8S_2$: m/z=673.

EXAMPLE 52

Following the procedures of the previous Examples, the compounds set forth in Tables 2-15 can be prepared.

TABLE 2

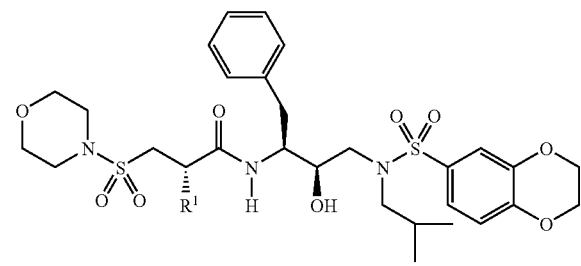

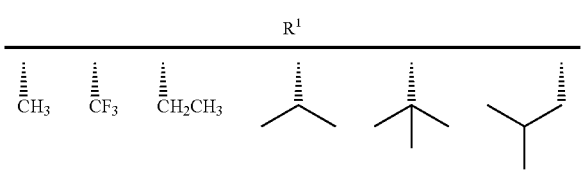

TABLE 2-continued

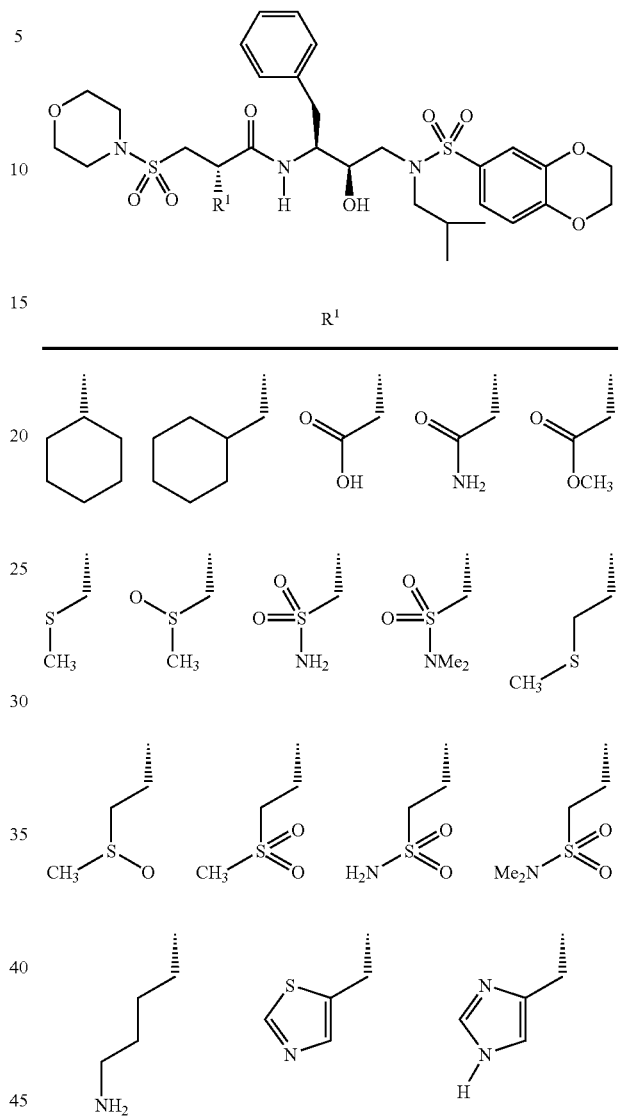

TABLE 3

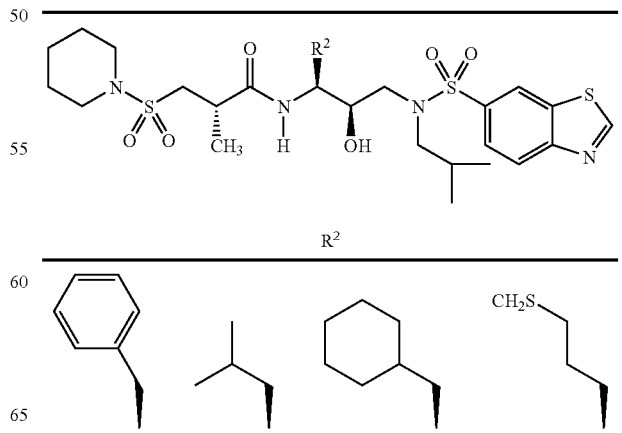

TABLE 3-continued
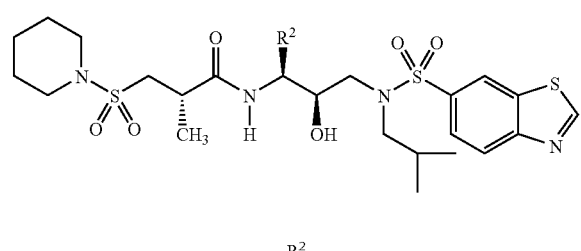
R²
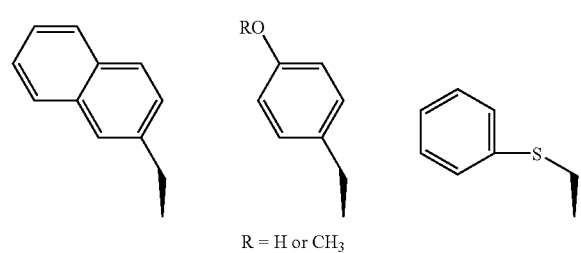
R = H or CH₃
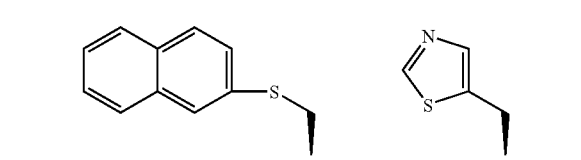
TABLE 4
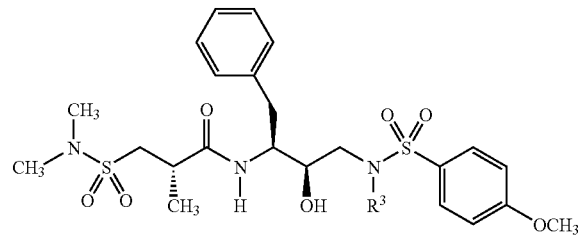
R³
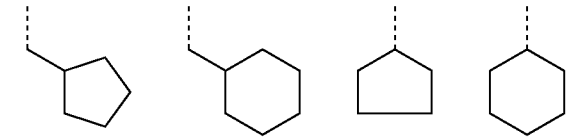
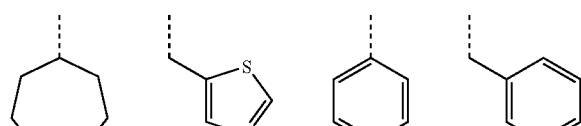
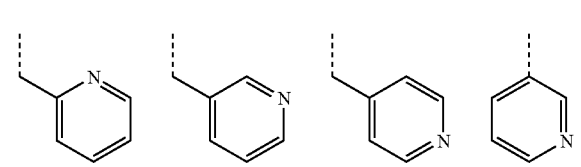
TABLE 4-continued
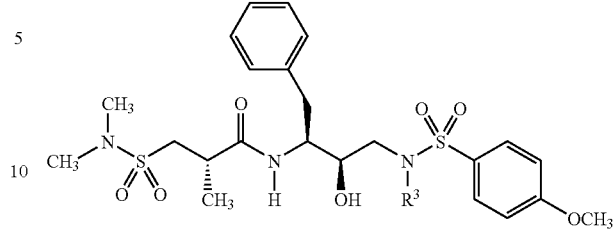
R³
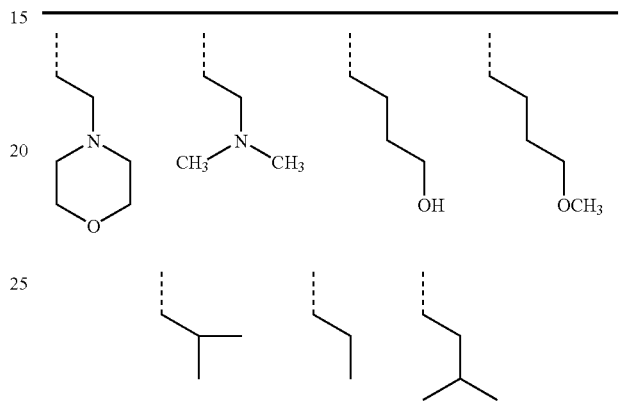
TABLE 5
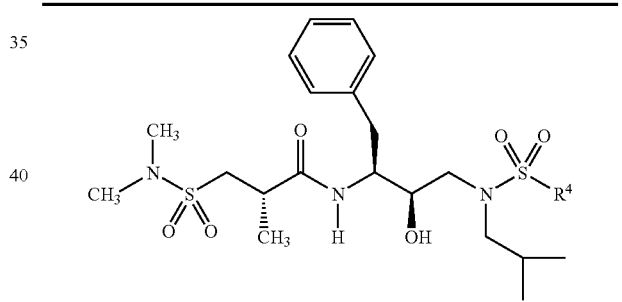
R⁴
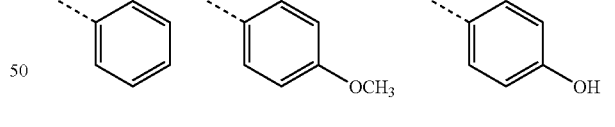
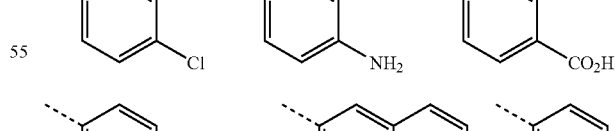
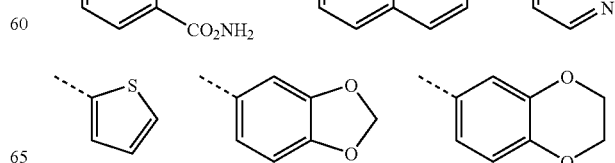

TABLE 5-continued
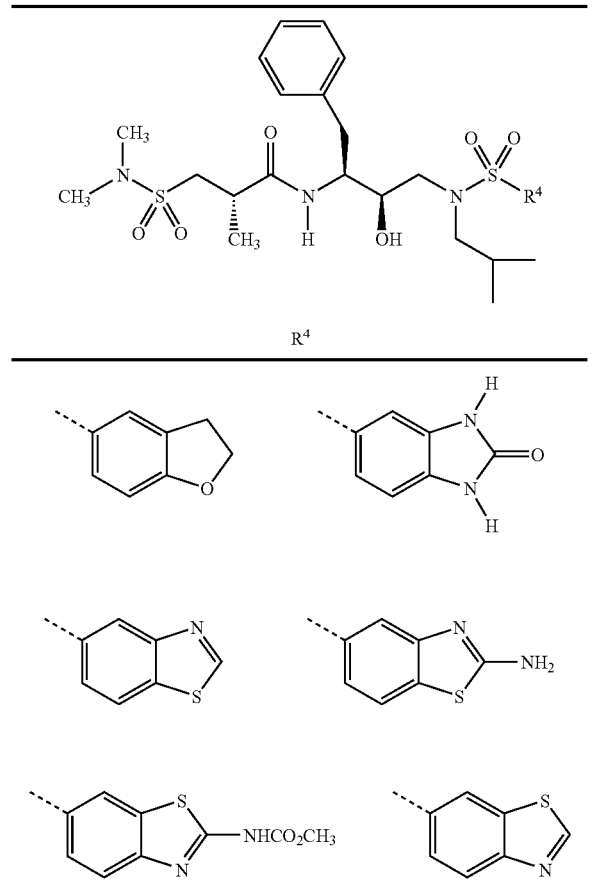
TABLE 5-continued
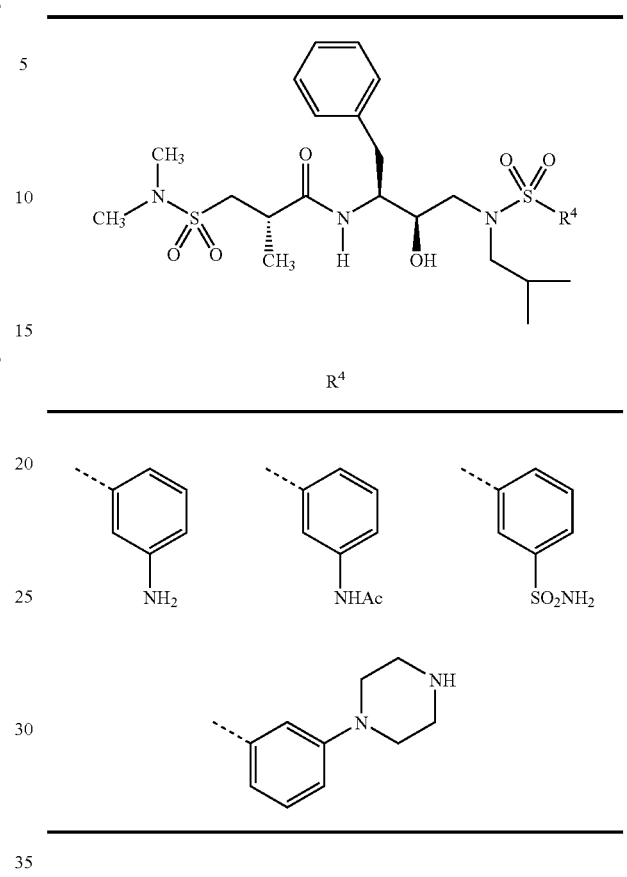
TABLE 6A
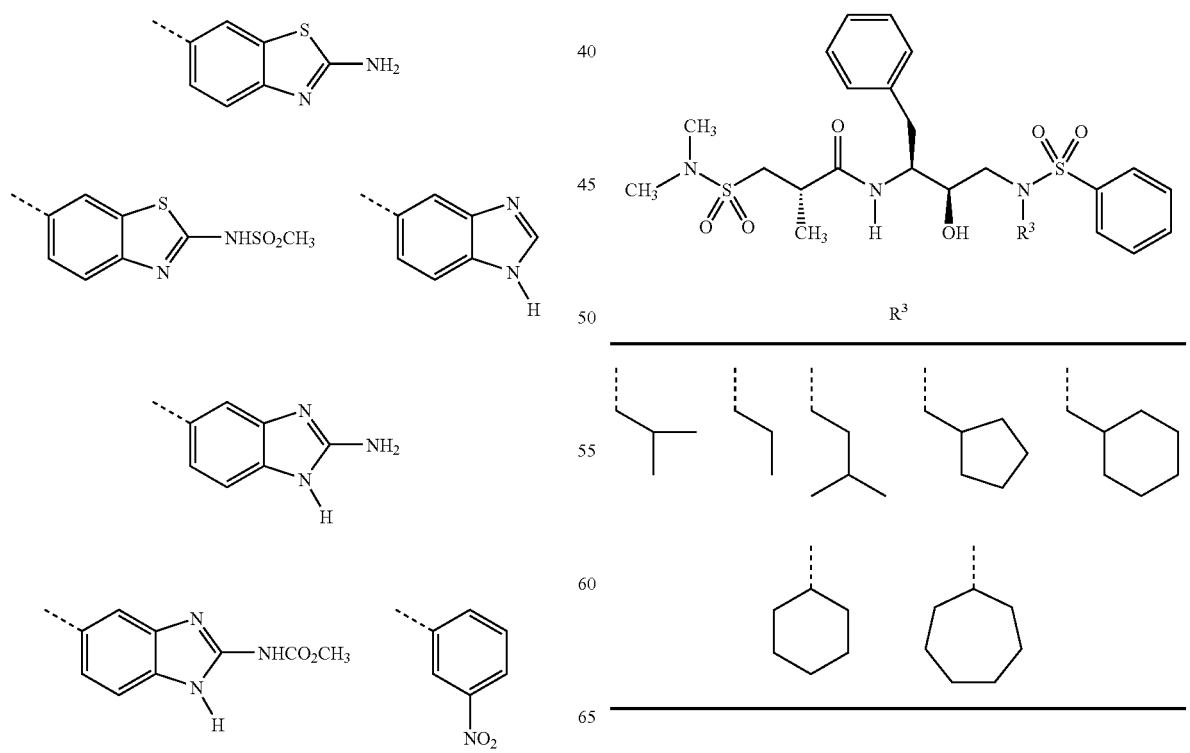

TABLE 6B
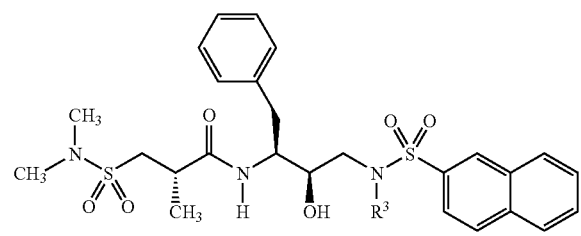
R³
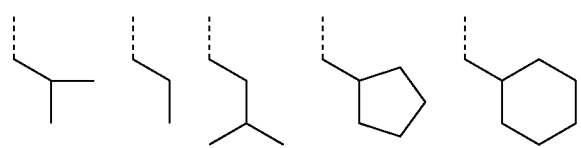
TABLE 6C
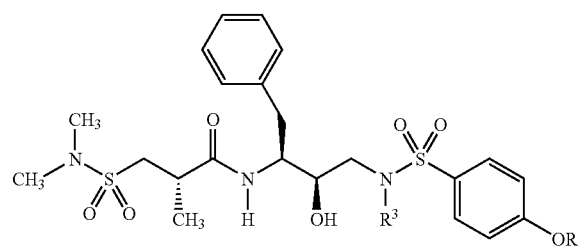
R = H or CH₃
R³
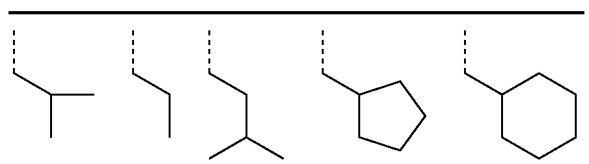
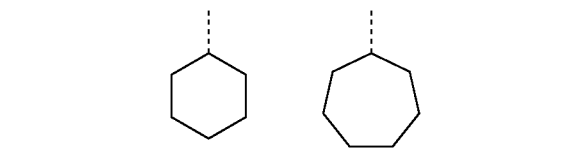
TABLE 6D
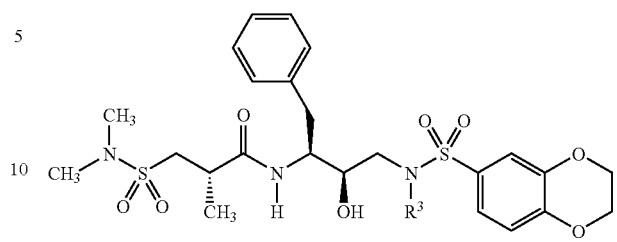
R³
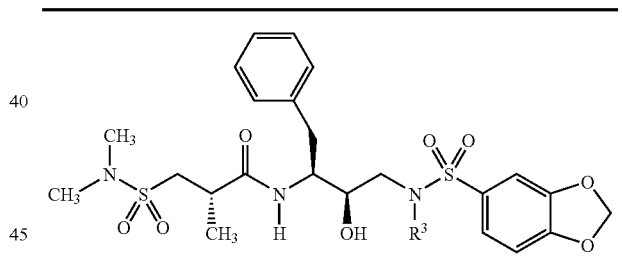
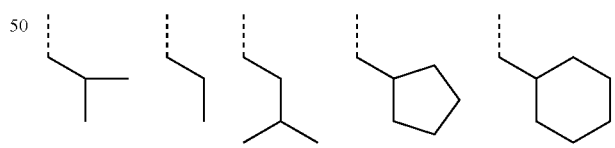
TABLE 6E
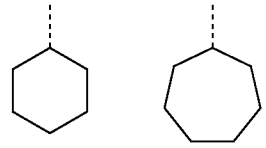

TABLE 6F
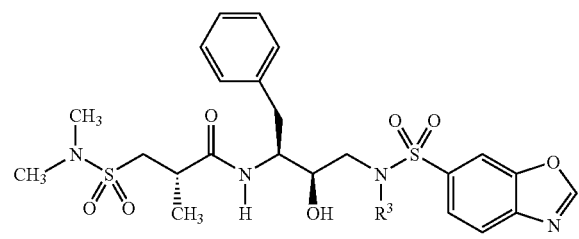
R³
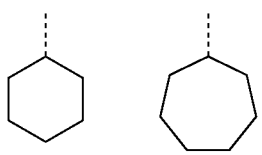
TABLE 6G
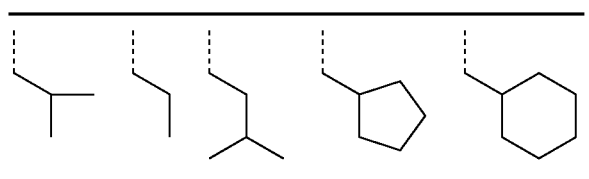
R³
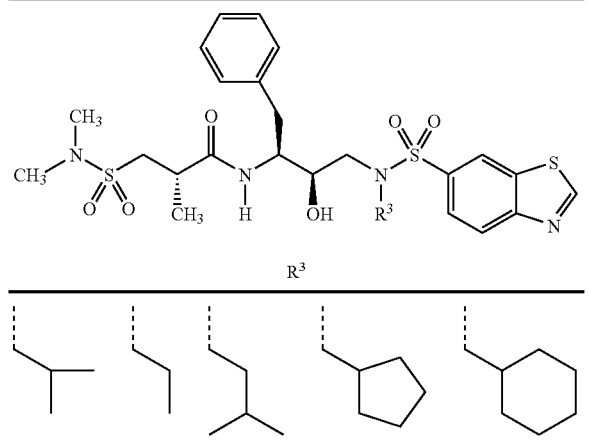
TABLE 6H
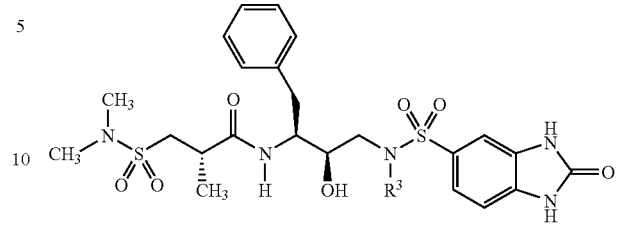
R³
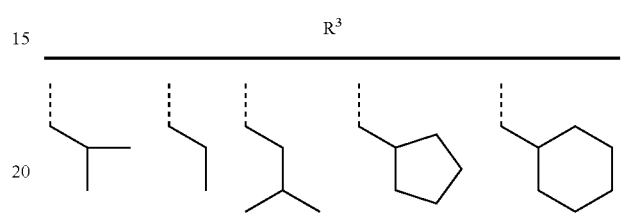
TABLE 7
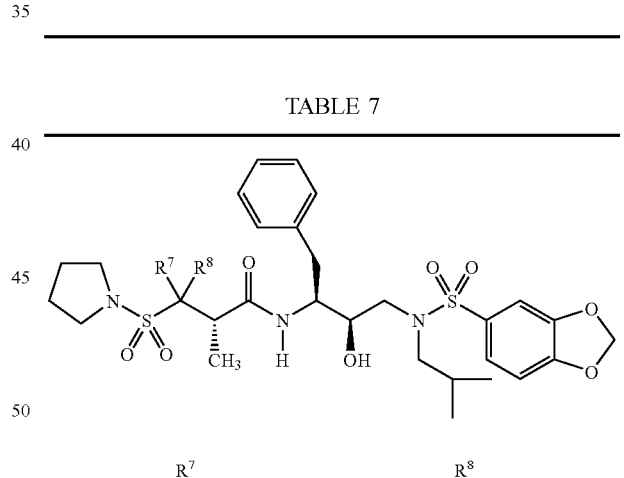
| R⁷ | R⁸ |
|---|---|
| H | H |
| CH₃ | H |
| CH₃ | H |
| CH₃ | CH₃ |
| phenyl | H |
| benzyl | H |
| —C(O)NH₂ | H |
| —C(NH)NH₂ | H |
| —CO₂H | H |
| —CO₂CH₃ | H |

TABLE 8
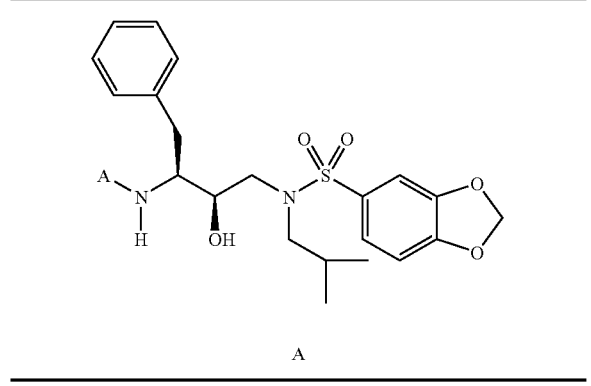
A
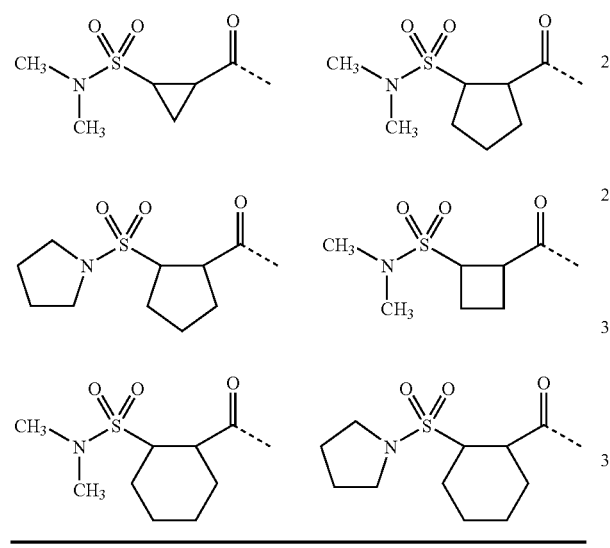
TABLE 9
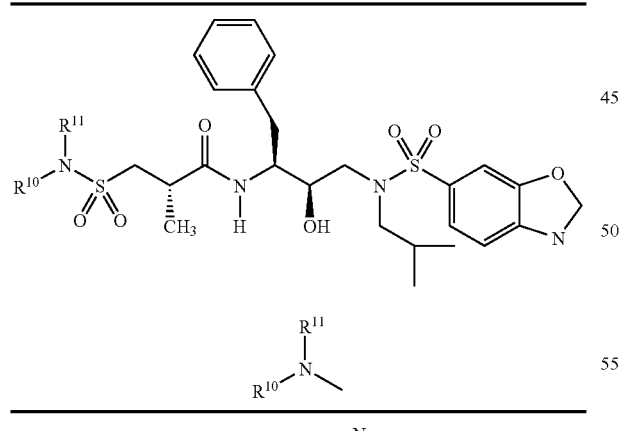
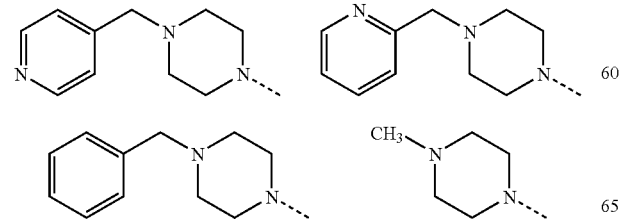
TABLE 9-continued
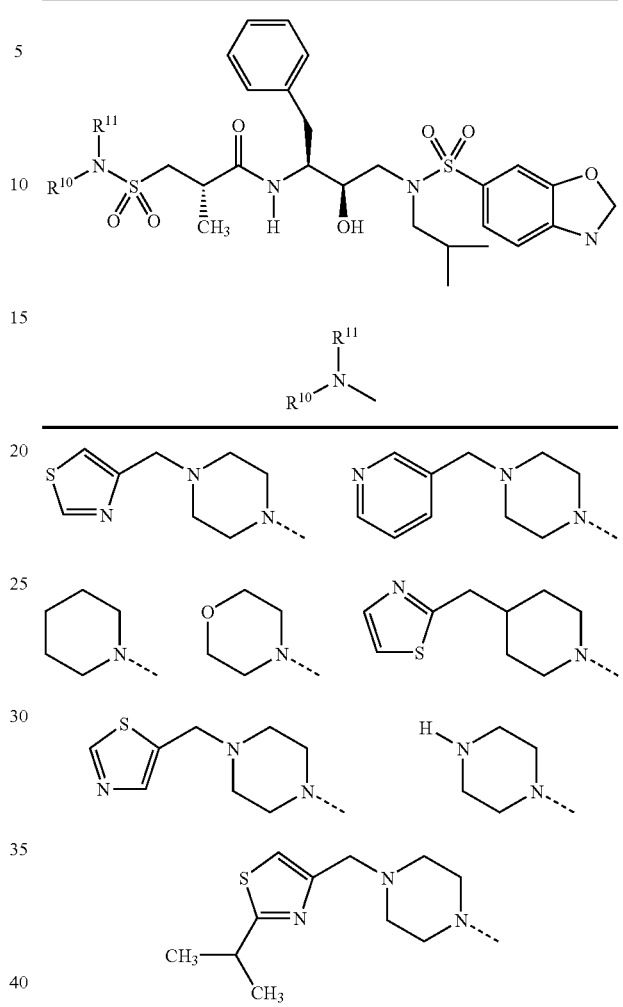

TABLE 9-continued
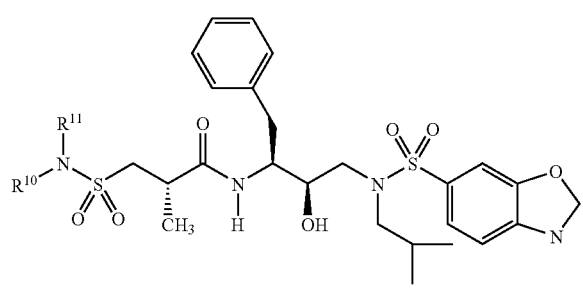
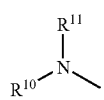
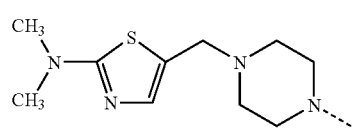
TABLE 10
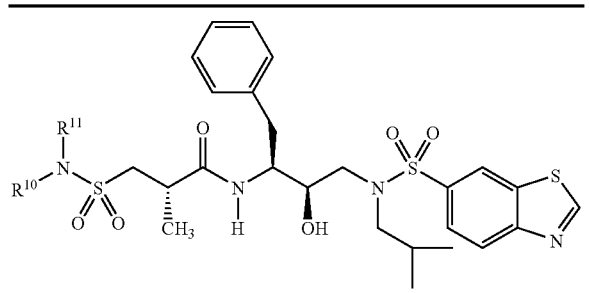
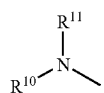
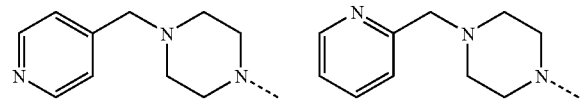
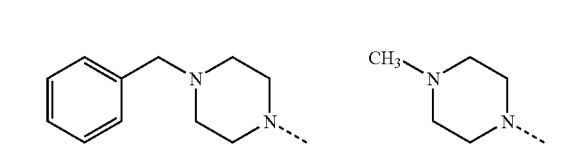
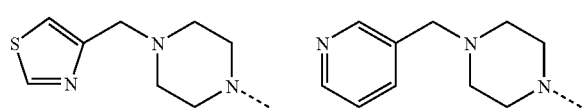
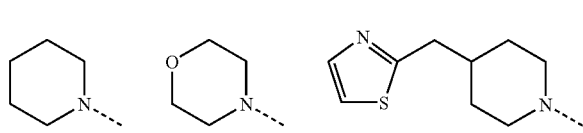
TABLE 10-continued
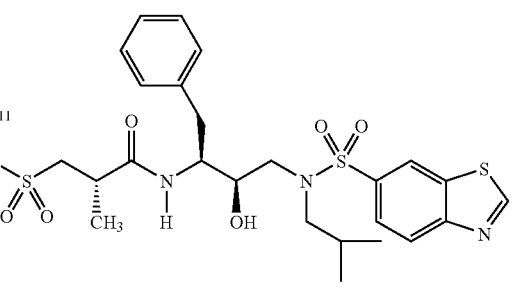
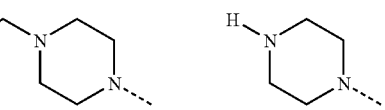
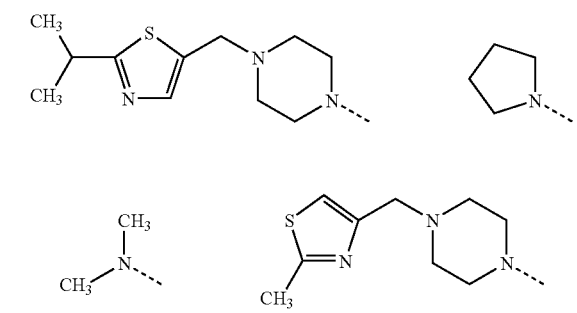
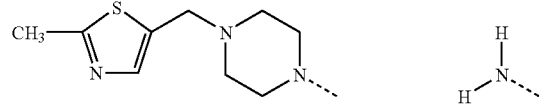
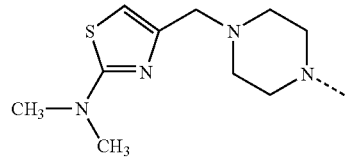
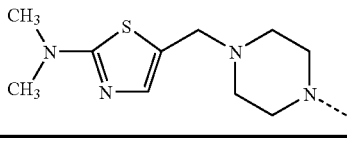

TABLE 11
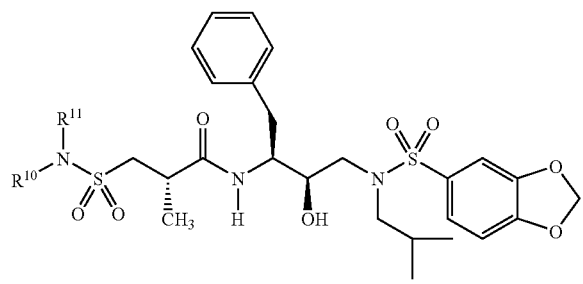
$R_{11}$ = H or CH$_3$
$R^{10}$
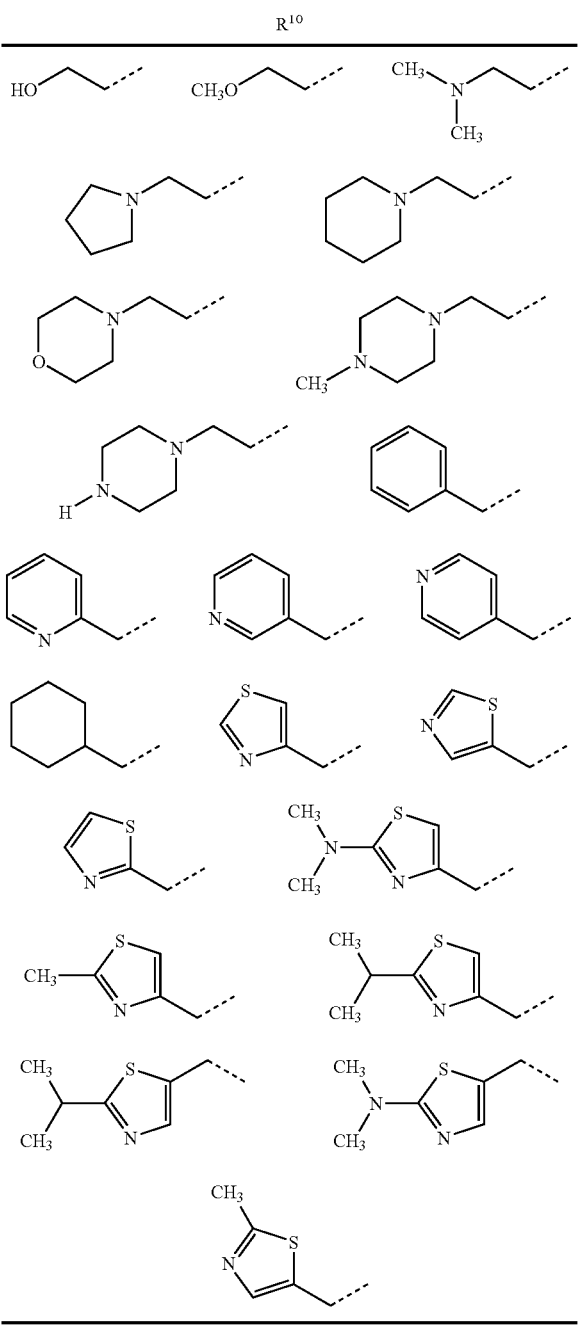
TABLE 12
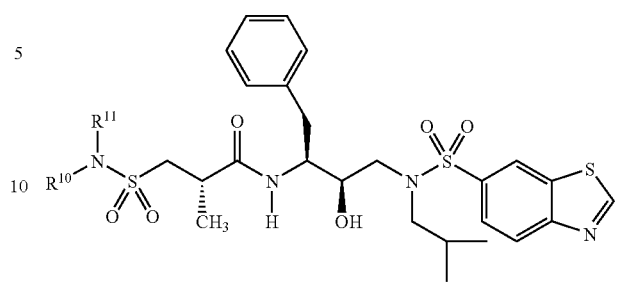
$R_{11}$ = H or CH$_3$
$R^{10}$
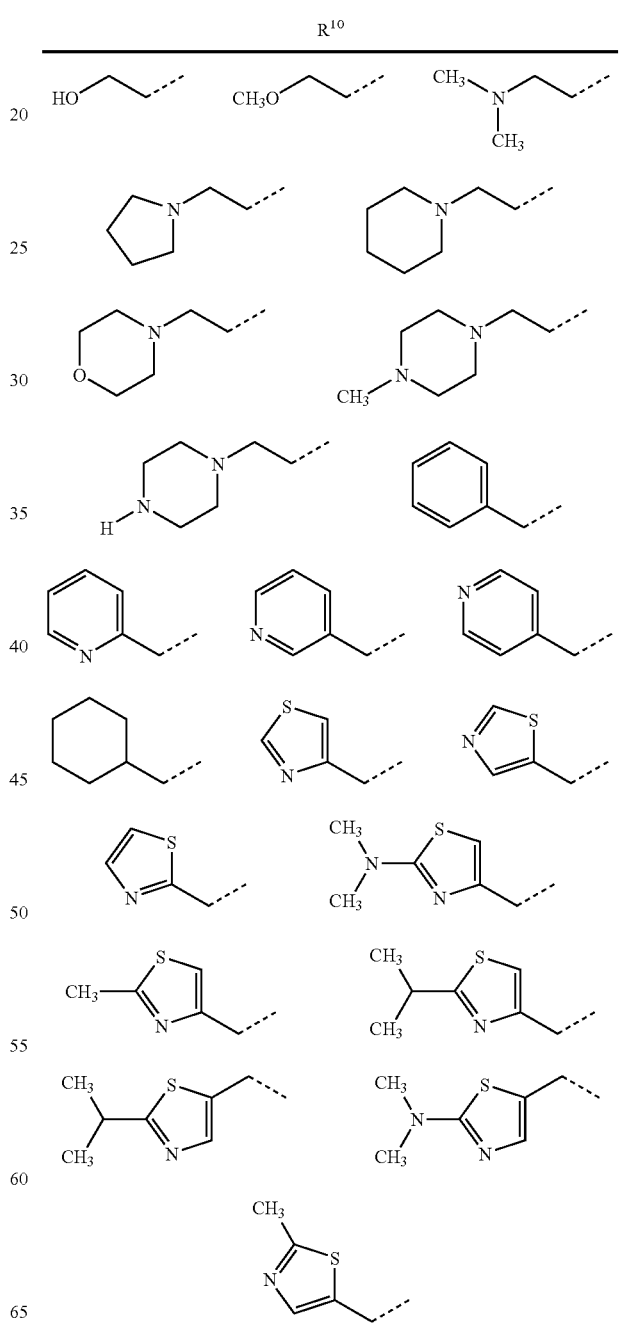

TABLE 13

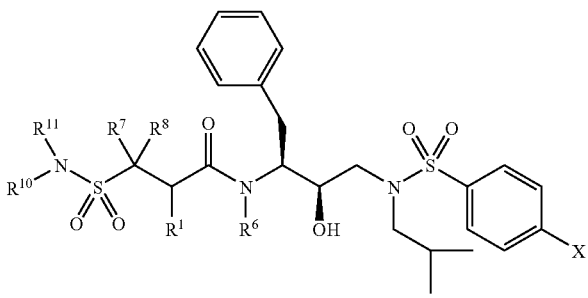

| X | R$^1$ | R$^6$ | R$^7$ | R$^8$ | R$^{10}$ | R$^{11}$ |
|---|---|---|---|---|---|---|
| —OCH$_3$ | —CH$_3$ | —H | —CH$_3$ | —CH$_3$ | —CH$_3$ | —CH$_3$ |
| —OCH$_3$ | —CH$_3$ | —H | —CH$_3$ | —CH$_3$ | —H | —H |
| —OCH$_3$ | —H | —H | —CH$_3$ | —CH$_3$ | —CH$_3$ | —H |
| —NH$_2$ | —CH$_3$ | —H | —H | —H | —CH$_3$ | -benzyl |
| —OCH$_3$ | —CH$_3$ | —H | -benzyl | —H | —H | —H |
| —NH$_2$ | —CH$_3$ | —H | —H | —H | —CH$_2$CH$_3$ | —CH$_2$CH$_3$ |
| —OH | —CH$_3$ | —H | —CH$_3$ | —CH$_3$ | —CH$_3$ | —CH$_3$ |
| —H | -benzyl | —H | —H | —H | —CH$_3$ | —H | —CH$_2$—C$_6$H$_4$—NH$_2$ |
| —OCH$_3$ | —CH$_3$ | —H | —H | —H | —H | —CH$_2$—C$_6$H$_4$—OH |
| —OCH$_3$ | —CH$_3$ | —H | —H | —H | —H | —CH$_2$—C$_6$H$_3$(OCH$_3$)$_2$ |
| —OCH$_3$ | —CH$_3$ | —H | —H | —H | —H | —CH$_2$CH$_2$-(1-imidazolyl) |
| —OCH$_3$ | —CH$_3$ | —CH$_3$ | —H | —H | —H | —CH$_2$-(benzoxazoline) |
| —OCH$_3$ | —CH$_3$ | —H | —H | —H | —CH$_3$ | —CH$_2$CH$_2$-(tetrahydrofuranyl) |
| —OCH$_3$ | —CH$_3$ | —CH$_3$ | —H | —H | —CH$_3$ | —CH$_3$ |
| —OCH$_3$ | —CH$_3$ | —H | —H | —H | —CH$_3$ | —CH$_2$CO—C$_6$H$_5$ |
| —OCH$_3$ | —CH$_3$ | —H | —H | —H | —CH$_3$ | -phenyl |
| —C(NH)NH$_2$ | —CH$_3$ | —H | —H | —H | —CH$_3$ | —CH$_3$ |
| —C(NH)NH$_2$ | —CH$_3$ | —H | —H | —H | —CH$_3$ | -phenyl |
| —C(NH)NH$_2$ | —CH$_3$ | —H | —H | —H | —CH$_3$ | -benzyl |

TABLE 14

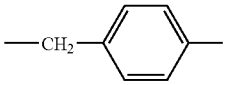

| X | —NR$^{10}$R$^{11}$ |
|---|---|
| —C(NH)NH$_2$ | pyrrolyl |
| —C(NH)NH$_2$ | pyrrolidinylyl |
| —C(NH)NH$_2$ | piperidinyl |
| —C(NH)NH$_2$ | —N(CH$_3$)$_2$ |
| —C(NCH$_3$)NH$_2$ | pyrrolyl |
| —C(NCH$_3$)NH$_2$ | pyrrolidinylyl |
| —C(NCH$_3$)NH$_2$ | piperidinyl |
| —C(NCH$_3$)NH$_2$ | —N(CH$_3$)$_2$ |

TABLE 15

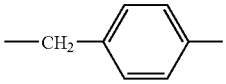

| R$^{10}$ | R$^{11}$ |
|---|---|
| —CH$_2$-C$_6$H$_4$-C(NH)NH$_2$ | —H |
| —CH$_2$-C$_6$H$_4$-C(NH)NH$_2$ | —CH$_3$ |
| —CH$_2$-C$_6$H$_4$-C(NH)NH$_2$ | -benzyl |
| -C$_6$H$_4$-C(NH)NH$_2$ | —H |
| -C$_6$H$_4$-C(NH)NH$_2$ | —CH$_3$ |
| -C$_6$H$_4$-C(NH)NH$_2$ | -benzyl |
| pyridinyl-C(NH)NH$_2$ | —H |

TABLE 15-continued

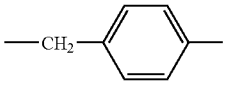

| R$^{10}$ | R$^{11}$ |
|---|---|
| pyridinyl-C(NH)NH$_2$ | —CH$_3$ |
| pyridinyl-C(NH)NH$_2$ | -benzyl |
| —NR$^{10}$R$^{11}$ = | pyrrolyl-C(NH)NH$_2$ |
| —NR$^{10}$R$^{11}$ = | pyrrolyl-C(NCH$_3$)NH$_2$ |
| —NR$^{10}$R$^{11}$ = | N-methyl-pyrrolidinyl-C(NH)NH$_2$ |
| —NR$^{10}$R$^{11}$ = | N-methyl-pyrrolidinyl-C(NCH$_3$)NH$_2$ |

EXAMPLE 53

The compounds of the present invention are effective HIV protease inhibitors. Utilizing an enzyme assay as described below, the compounds set forth in the examples herein disclosed inhibited the HIV enzyme. The preferred compounds of the present invention and their calculated IC$_{50}$ (inhibiting concentration 50%, i.e., the concentration at which the inhibitor compound reduces enzyme activity by 50%) values are shown in Table 16. The enzyme method is described below. The substrate is 2-Ile-Nle-Phe(p-NO$_2$)-Gln-ArgNH$_2$. The positive control is MVT-101 (Miller, M. et al, *Science*, 246, 1149 (1989)] The assay conditions are as follows:

Assay buffer: 20 mM sodium phosphate, pH 6.4
  20% glycerol
  1 mM EDTA
  1 mM DTT
  0.1% CHAPS The above described substrate is dissolved in DMSO, then diluted 10 fold in assay buffer. Final substrate concentration in the assay is 80 μM.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 µl of the enzyme preparation is added, the materials mixed and then the mixture is incubated at ambient temperature for 15 minutes. The enzyme reaction is initiated by the addition of 40 µof substrate. The increase in fluorescence is monitored at 4 time points (0, 8, 16 and 24 minutes) at ambient temperature. Each assay is carried out in duplicate wells.

The preceding examples can be repeated with similar success by substituting the generically or specifically described reactants and/or operating conditions of this invention for those used in the preceding examples.

EXAMPLE 54

The effectiveness of various compounds were determined in the above-described enzyme assay and in a CEM cell assay.

The HIV inhibition assay method of acutely infected cells is an automated tetrazolium based calorimetric assay essentially that reported by Pauwles et al, *J. Virol. Methods*, 20, 309-321 (1988). Assays were performed in 96-well tissue culture plates. CEM cells, a CD4$^+$ cell line, were grown in RPMI-1640 medium (Gibco) supplemented with a 10% fetal calf serum and were then treated with polybrene (2 µg/ml). An 80 µl volume of medium containing 1×10$^4$ cells was dispensed into each well of the tissue culture plate. To each well was added a 100 µl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ TCID$_{50}$ per ml (TCID$_{50}$=the dose of virus that infects 50% of cells in tissue culture), and a 20 µL volume of the virus sample (containing 1000 TCID$_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

|    | Cells | Drug | Virus |
|----|-------|------|-------|
| 1. | +     | −    | −     |
| 2. | +     | +    | −     |
| 3. | +     | −    | +     |
| 4. | +     | +    | +     |

In experiments 2 and 4 the final concentrations of test compounds were 1, 10, 100 and 500 µg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% CO$_2$ atmosphere for 7 days. Test compounds could be added on days 0, 2 and 5 if desired. On day 7, post-infection, the cells in each well were resuspended and a 100 µl sample of each cell suspension was removed for assay. A 20 µL volume of a 5 mg/ml solution of 3-(4,5-dimethylthiazol-2-yl)-2,5-diphenyltetrazolium bromide (MTT) was added to each 100 µL cell suspension, and the cells were incubated for 4 hours at 27° C. in a 5% CO$_2$ environment. During this incubation, MTT is metabolically reduced by living cells resulting in the production in the cell of a colored formazan product. To each sample was added 100 µl of 10% sodium dodecylsulfate in 0.01 N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy. The results of selected compounds are shown in Table 16.

TABLE 16

| Entry | Compound | IC$_{50}$ (nm) | EC$_{50}$ (nm) |
|-------|----------|----------------|----------------|
| 1     | 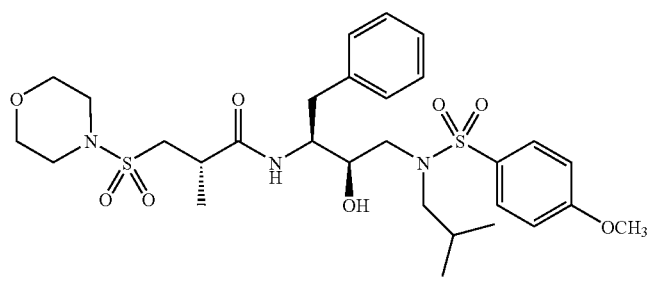 | 10 | 32 |

TABLE 16-continued

| Entry | Compound | IC$_{50}$ (nm) | EC$_{50}$ (nm) |
|---|---|---|---|
| 2 | | 8 | 77 |
| 3 | | 6 | 40 |
| 4 | | 4 | 15 |
| 5 | | 13 | 210 |
| 6 | | 4 | |

TABLE 16-continued

| Entry | Compound | IC$_{50}$ (nm) | EC$_{50}$ (nm) |
|---|---|---|---|
| 7 | *(structure)* | 3 | 32 |
| 8 | *(structure)* | 9 | 415 |
| 9 | *(structure)* | 6 | 84 |
| 10 | *(structure)* | 10 | 56 |
| 11 | *(structure)* | 9 | |

TABLE 16-continued

| Entry | Compound | IC$_{50}$ (nm) | EC$_{50}$ (nm) |
|---|---|---|---|
| 12 | | 9 | 42 |
| 13 | | 6 | 176 |
| 14 | | 4 | 85 |
| 15 | | 4 | |

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment and/or proplylaxis of retroviral infections.

The subject compounds are also effective in preventing the growth of retroviruses in a solution. Both human and animal cell cultures, such as T-lymphocyte cultures, are utilized for a variety of well known purposes, such as research and diagnostic procedures including calibrators and controls. Prior to and during the growth and storage of a cell culture, the subject compounds may be added to the cell culture medium at an effective concentration to prevent the unexpected or undesired replication of a retrovirus that may inadvertently or unknowingly be present in the cell culture. The virus may be present originally in the cell culture, for example HIV is known to be present in human T-lymphocytes long before it is detectable in blood, or through exposure to the virus. This use of the subject compounds prevents the unknowing or inadvertent exposure of a potentially lethal retrovirus to a researcher or clinician.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

The compounds of the present invention can also be used in the form of prodrugs and esters of Formula I. The term "prodrug" contemplated herein is a derivative of Formula I which upon administration to a subject is chemically converted by metabolic or chemical processes to yield a compound of Formula I or a salt thereof. See H. Bundgnard, "Drugs of the Future" 16:443-458 (1991); and H. Bundgnard, "Design of Prodrugs" Elsevier, Amsterdam, 1985, both incorporated herein by reference.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with glucosidase inhibitors, such as N-butyl-1-deoxynojirimycin or prodrugs thereof, for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

The invention claimed is:

1. A compound represented by the formula:

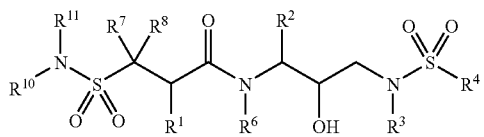

or a pharmaceutically acceptable salt thereof, wherein
$R^1$ represents a hydrogen, alkyl, or a side chain of an amino acid selected from the group consisting of leucine, norleucine, isoleucine, allo-isoleucine, alanine, tert-leucine, and valine;
$R^2$ represents cycloalkyl or aralkyl;
$R^3$ represents alkyl, cycloalkyl, or cycloalkylalkyl;
$R^4$ represents heterocyclo, heteroaryl, or aryl;
$R^6$ represents a hydrogen or alkyl;
$R^7$ and $R^8$ each independently represent a hydrogen or alkyl; and
$R^{10}$ and $R^{11}$ together with the nitrogen atom to which they are bonded represent heterocyclo, aralkylheteroaryl, aralkylheterocyclo, heteroaralkylheteroaryl or heteroaralkylheterocyclo;
wherein heteroaryl, as used alone or in combination, is optionally substituted with one or more radicals selected from the group consisting of alkyl, alkoxy, hydroxy, alkylthio, alkylsulfinyl, alkylsulfonyl, halo, amino, nitro, cyano, haloalkyl, carboxy, alkoxycarbonyl, alkanoylamino, amido, amidino, N-alkylamidino, alkylamino, dialkylamino, N-alkylamido, N,N-dialkylamido, alkoxycarbonylamino, and alkylsulfonylamino;
wherein cycloalkyl and aryl, as used alone or in combination, are optionally substituted with one or more radicals selected from the group consisting of alkyl, alkoxy, hydroxy, alkylthio, alkylsulfinyl, alkylsulfonyl, halo, amino, nitro, cyano, haloalkyl, carboxy, alkoxycarbonyl, alkanoylamino, amido, amidino, N-alkylamidino, alkylamino, dialkylamino, N-alkylamido, N,N-dialkylamido, and alkoxycarbonylamino; and
wherein heterocyclo, as used alone or in combination, is optionally substituted with one or more radicals selected from the group consisting of alkyl, alkoxy, hydroxy, amidino, N-alkylamidino, alkoxycarbonylamino, and alkylsulfonylamino.

2. The compound of claim 1 or a pharmaceutically acceptable salt thereof, wherein $R^{10}$ and $R^{11}$ together with the nitrogen atom to which they are bonded represent heterocyclo which is optionally substituted on a nitrogen ring atom with alkyl.

3. The compound of claim 1 or a pharmaceutically acceptable salt thereof, wherein $R^{10}$ and $R^{11}$ together with the nitrogen atom to which they are bonded represent piperidinyl, morpholinyl, piperazinyl, N-methylpiperazinyl, pyrrolidinyl, amidinopyrrolidinyl, (N-methylamidino)pyrrolidinyl, pyrrolyl, amidinopyrrolyl, (N-methylamidino)pyrrolyl, N-benzylpiperazinyl, N-(pyridylmethyl)piperazinyl, N-[(N-methylaminothiazolyl)methyl]piperazinyl, N-[(N,N-dimethylaminothiazolyl)methyl]piperazinyl, N-(thiazolylmethyl)piperazinyl, or N-[(isopropylthiazolyl)methyl]piperazinyl.

4. The compound of claim 3 or a pharmaceutically acceptable salt thereof, wherein $R^{10}$ and $R^{11}$ together with the nitrogen atom to which they are bonded represent piperidinyl, morpholinyl, piperazinyl, N-methylpiperazinyl, pyrrolidinyl, pyrrolyl, N-benzylpiperazinyl, N-(pyridylmethyl)piperazinyl, or N-(thiazolylmethyl)piperazinyl.

5. The compound of claim 4 or a pharmaceutically acceptable salt thereof, wherein $R^{10}$ and $R^{11}$ together with the nitrogen atom to which they are bonded represent piperidinyl, morpholinyl, piperazinyl, N-methylpiperazinyl, pyrrolidinyl, N-benzylpiperazinyl, or N-(pyridylmethyl)piperazinyl.

6. The compound of claim 1 or a pharmaceutically acceptable salt thereof wherein $R^1$ represents a hydrogen methyl, ethyl, isopropyl, propyl, or a side chain of an amino acid selected from the group consisting of alanine and valine.

7. The compound of claim 6 or a pharmaceutically acceptable salt thereof, wherein $R^1$ represents a hydrogen or methyl.

8. The compound of claim 1 or a pharmaceutically acceptable salt thereof, wherein $R^2$ represents benzyl, fluorobenzyl, or cyclohexylmethyl.

9. The compound of claim 8 or a pharmaceutically acceptable salt thereof, wherein $R^2$ represents benzyl.

10. The compound of claim 1 or a pharmaceutically acceptable salt thereof, wherein $R^3$ represents isoamyl, isobutyl, cyclohexyl, cycloheptyl, cyclohexylmethyl, or cyclopentylmethyl.

11. The compound of claim 1 or a pharmaceutically acceptable salt thereof, wherein $R^3$ represents isobutyl.

12. The compound of claim 1 or a pharmaceutically acceptable salt thereof, wherein $R^4$ represents phenyl, naphthyl, benzothiazolyl, 2,3-dihydrobenzofuranyl, 1,3-benzodioxolyl, 1,4-benzodioxanyl, benzimidazolyl, benzimidazolonyl, or benzoxazolyl, or phenyl having one or more substituents selected from the group consisting of methyl, methoxy, ethoxy, methylthio, fluoro, chloro, amino, and methoxycarbonylamino.

13. The compound of claim 12 or a pharmaceutically acceptable salt thereof, wherein $R^4$ represents phenyl, 4-methoxyphenyl, or 1,3-benzodioxolyl.

14. The compound of claim 1 or a pharmaceutically acceptable salt thereof, wherein $R^6$ represents a hydrogen.

15. The compound of claim 1 or a pharmaceutically acceptable salt thereof, wherein $R^7$ and $R^8$ each represent a hydrogen.

16. The compound of claim 1 which is
$N^1$-[1-[N-(2-methylpropyl)-N-(phenylsulfonyl)amino]-2R-hydroxy-3S-(phenylmethyl)prop-3-yl]-3-(1-morpholinosulfonyl)-2R-methylpropionamide;
$N^1$-[1-[N-(2-methylpropyl)-N-(phenylsulfonyl)amino]-2R-hydroxy-3S-(phenylmethyl)prop-3-yl]-3-[(4-methylpiperazin-1-yl)sulfonyl]-2R-methylpropionamide;
$N^1$-[1-[N-(2-methylpropyl)-N-(phenylsulfonyl)amino]-2R-hydroxy-3S-(phenylmethyl)prop-3-yl]-3-(1-piperidinyl)sulfonyl-2R-methylpropionamide;
$N^1$-[1-[N-(2-methylpropyl)-N-[[(4-methoxy)phenyl]sulfonyl]amino]-2R-hydroxy-3S-(phenylmethyl)prop-3-yl]-3-(1-piperidinyl)sulfonyl-2R-methylpropionamide;
$N^1$-[1-[N-(2-methylpropyl)-N-[(1,3-benzodioxol-5-yl)sulfonyl]amino]-2R-hydroxy-3S-(phenylmethyl)prop-3-yl]-3-[(4-methylpiperazin-1-yl)sulfonyl]-2R-methylpropionamide;
$N^1$-[1-[N-(2-methylpropyl)-N-[[(4-methoxy)phenyl]sulfonyl]amino]-2R-hydroxy-3S-(phenylmethyl)prop-3-yl]-3-[(4-methylpiperazin-1-yl)sulfonyl]-2R-methylpropionamide;
$N^1$-[1-[N-(2-methylpropyl)-N-[(1,3-benzodioxol-5-yl)sulfonyl]amino]-2R-hydroxy-3S-(phenylmethyl)prop-3-yl]-3-[(piperazin-1-yl)sulfonyl]-2R-methylpropionamide;
$N^1$-[1-[N-(2-methylpropyl)-N-[(1,3-benzodioxol-5-yl)sulfonyl]amino]-2R-hydroxy-3S-(phenylmethyl)prop-3-yl]-3-[[4-(4-pyridylmethyl)piperazin-1-yl]sulfonyl]-2R-methylpropionamide;
$N^1$-[1-[N-(2-methylpropyl)-N-[(1,3-benzodioxol-5-yl)sulfonyl]amino]-2R-hydroxy-3S-(phenylmethyl)prop-3-yl]-3-[(1-morpholinyl)sulfonyl]-2R-methylpropionamide;
$N^1$-[1-[N-(2-methylpropyl)-N-[(1,3-benzodioxol-5-yl)sulfonyl]amino]-2R-hydroxy-3S-(phenylmethyl)prop-3-yl]-3-[(1-pyrrolidinyl)sulfonyl]-2R-methylpropionamide; or
$N^1$-[1-[N-(2-methylpropyl)-N-[(1,3-benzodioxol-5-yl)sulfonyl]amino]-2R-hydroxy-3S-(phenylmethyl)prop-3-yl]-3-[(1-piperidinyl)sulfonyl]-2R-methylpropionamide;
or a pharmaceutically acceptable salt thereof.

17. The compound of claim 1 or a pharmaceutically acceptable salt thereof, wherein, in said formula, the stereochemistry of the carbon atom bonded to the substituent $R^2$ is designated as (S).

18. The compound of claim 1 or a pharmaceutically acceptable salt thereof, wherein, in said formula, the stereochemistry of the carbon atom bonded to the hydroxyl radical is designated as (R).

19. A pharmaceutically acceptable salt of the compound of claim 1, wherein said pharmaceutically acceptable salt is derived from an acid selected from the group consisting of hydrochloric acid, sulfuric acid, phosphoric acid, oxalic acid, maleic acid, succinic acid, and citric acid.

20. A pharmaceutical composition comprising the compound of claim 1 or a pharmaceutically acceptable salt thereof and a pharmaceutically acceptable carrier.

* * * * *